US008178515B2

(12) United States Patent
De La Cruz Cordero et al.

(10) Patent No.: US 8,178,515 B2
(45) Date of Patent: May 15, 2012

(54) β-HYDROXY-γ-AMINOPHOSPHONATES AND METHODS FOR THE PREPARATION AND USE THEREOF

(75) Inventors: Ricardo Abraham De La Cruz Cordero, Huixtla Chis (MX); Miguel Angel Duarte-Vazquez, Guanajuato (MX); Jorge Luis Rosado Loria, Querétaro (MX)

(73) Assignee: Nucitec S.A. de C.V., Queretaro (MX)

( * ) Notice: Subject to any disclaimer, the term of this patent is extended or adjusted under 35 U.S.C. 154(b) by 125 days.

(21) Appl. No.: 12/575,856

(22) Filed: Oct. 8, 2009

(65) Prior Publication Data

US 2010/0087400 A1 Apr. 8, 2010

Related U.S. Application Data

(60) Provisional application No. 61/136,845, filed on Oct. 8, 2008.

(51) Int. Cl.
*A61K 31/662* (2006.01)
*C07F 9/40* (2006.01)

(52) U.S. Cl. .......................................... 514/114; 564/15
(58) Field of Classification Search .................. 514/114; 558/169; 562/11
See application file for complete search history.

(56) References Cited

U.S. PATENT DOCUMENTS

| 6,444,701 B1 | 9/2002 | Giannessi et al. |
| 2003/0162754 A1 | 8/2003 | Ligon |
| 2007/0207983 A1 | 9/2007 | Nieuwenhuizen et al. |

FOREIGN PATENT DOCUMENTS

| FR | 1543469 | * 9/1968 |

OTHER PUBLICATIONS

Stahl, Handbook of Pharmaceutical Salts, 2002, Wiley-Ch, p. 1-7, 84, 161-173, 214-215, 310-311.*
Wang, Enzymatic synthesis of phosphocarnitine, phosphogabob and fosfomycin, 2003, Org. Biomol. Chem. vol. 1, p. 3564-3569.*
Wroblewski, An Efficient Synthesis of Enantiomeric (S)-Phosphocarnitine, 2002, Er. J. Org. Chem., p. 2758-2763.*
Yamagishi, Asymmetric synthesis of phosphonic acid analogues for acylcarnitine, 2006, Tetrahedron, vol. 62, p. 54-65.*
De la Cruz-Cordero, R. et al., "Preparation of phosphostatine and phosphoepistatine from L-leucine via high diastereoselective reduction of 3-amino-2-ketophosphonates," *ARKIVOC* (vi):277-286, ARKAT USA, Inc. (2005).
Mikolajczyk, M. et al., "Chemoenzymatic Synthesis of Phosphocarnitine Enantiomers," *J. Org. Chem.* 67:7872-7875, American Chemical Society (2002).
Ordonez, M. and Cativiela, C., "Stereoselective synthesis of γ-amino acids," *Tetrahedron Asymmetry 18*:3-99, Elsevier Ltd. (2007).
Young, L.W., International Search Report and Written Opinion for International Patent Application No. PCT/IB09/07234, International Search Authority, U.S. Patent and Trademark Office, Alexandria, Virginia, mailed Mar. 19, 2010.

* cited by examiner

*Primary Examiner* — Andrew D Kosar
*Assistant Examiner* — Karen Cheng
(74) *Attorney, Agent, or Firm* — Sterne, Kessler, Goldstein & Fox P.L.L.C.

(57) ABSTRACT

The present invention provides β-hydroxy-γ-aminophosphonates, β-amino-γ-aminophosphonates, and analogs thereof that inhibit carnitine acyltransferases. The invention also provides compositions comprising these β-hydroxy-γ-aminophosphonates, β-amino-γ-aminophosphonates, and analogs, and methods of the use of such compounds and compositions in the treatment, amelioration or prevention of pathological conditions, diseases or disorders that are linked with fatty acid metabolism, such as non-insulin dependent diabetes or obesity. The invention also provides processes for the preparation of such compounds and compositions.

21 Claims, 7 Drawing Sheets

β-HYDROXY-γ-AMINOPHOSPHONATES AND METHODS FOR THE PREPARATION AND USE THEREOF

CROSS-REFERENCE TO RELATED APPLICATIONS

This application claims the benefit of U.S. Provisional Application No. 61/136,845, filed Oct. 8, 2008, the disclosure of which is herein incorporated by reference in its entirety.

BACKGROUND OF THE INVENTION

1. Field of the Invention

This invention is in the field of medicinal chemistry. In particular, the invention relates to carnitine analogs such as β-hydroxy-γ-aminophosphonates and β-amino-γ-aminophosphonates that inhibit carnitine acyltransferases, and intermediates, precursors, and derivatives thereof. In another embodiment, the invention relates to the use of β-hydroxy-γ-aminophosphonates and β-amino-γ-aminophosphonates, and analogs and derivatives thereof, for the treatment, amelioration or prevention of pathological conditions, diseases or disorders that are linked with fatty acid metabolism, such as non-insulin dependent diabetes or obesity. In another embodiment, the invention relates to methods for the preparation of β-hydroxy-γ-aminophosphonates, and intermediates, precursors, derivatives, and analogs thereof.

2. Related Art

L-carnitine, also known as levocarnitine or vitamin $B_T$, is a cofactor that is present in tissues of animals, including humans, and serves several vital physiological roles. In particular, L-carnitine reacts with long chain fatty acids which cannot pass through the mitochondrial membrane. After such reaction, fatty acids are converted into membrane-permeable derivatives. In this pathway, L-carnitine plays a vital role for the utilization of fatty acids in mitochondria, via oxidation for the production of energy in eukaryotic organisms. This cofactor functions by binding activated fatty acids in the form of acyl carnitine (carnitine shuttle).

The use of L-carnitine in the treatment of hyperlipoproteinemia, hyperlipidemia, and myocardial dysfunction has been the subject of intense investigation (see, for example, Carazza, U.S. Pat. No. 4,255,449; Ramacci, U.S. Pat. No. 4,315,944; Siliprandi, *Hypolipidemic Drugs*, G. Ricci (Ed.), New York; Raven, 1982; Pauly et al., *Am. J. Kidney Dis.* 41:S35-S43 (2003); Calvani et al., *Basic Res. Cardiol.* 95:75-83 (2000)). L-carnitine has also been reported to be useful as an adjuvant therapy in the management of renal anemia (Ciancuaruso, et al., *Contrib. Nephrol.* 137:426-430 (2002)). Certain carnitine analogs or derivatives have also been shown to have potential therapeutic value. For example, propionyl carnitine (the propionic ester of carnitine) has been shown to improve cardiac function (see, for example, Wiseman et al., *Drugs Aging* 12:243-248 (1998); Ferrari et al., *Developments in Cardiovascular Medicine* 162:323 (1995)). Acetyl carnitine has been proposed as a possible therapeutic agent for Alzheimer's disease (Pettegrew et al., *Expert Review of Neurotherapeutics* 2:647-654 (2002)). Bromoacetyl-L-carnitine has been shown in vitro to have a potent effect against *T. Bruceli*, a causative agent of African trypanosomiases (Gilbert et al., *Biochem. Pharmacol.* 32:3447-3451 (1983)). However, the potential therapeutic benefit of bromoacetyl-L-carnitine is limited because of toxicity due to metabolic release of bromine and/or bromoacetoacetate.

CPS 124, a carnitine monothiophosphate derivative which is a reversible and competitive inhibitor of carnitine palmitoyl transferase I, is reportedly undergoing clinical development for the treatment of non-insulin dependent diabetes mellitus (NIDDM) (Anderson, *Curr. Pharm. Des.* 4:1-16 (1998)). Nicotinyl carnitine derivatives have been studied as anticholesteremics and hypolipemics (Chibata et al., U.S. Pat. No. 4,032,641). Acylated aminocarnitines (Griffith, U.S. Pat. No. 4,781,863 and Giannessi et al., WO 2008/15081) have been studied as anticholesteremics and hypolipemics.

Carnitine acyltransferases are a group of structurally related enzymes involved in lipid catabolism. More specifically, these enzymes participate in fatty acid oxidation, catalyzing the exchange of acyl groups between carnitine and Coenzyme A (CoA) (Bieber, *Ann. Rev. Biochem.* 57:261-283 (1988); Kerner et al., *Biochim. Biophys. Acta* 1486:1-17 (2000); McGarry at al., *Eur. J. Biochem.* 244:1-14 (1997); Ramsay et al., *Biochim. Biophys. Acta* 1546:21-43 (2001)). Among the carnitine acyltransferases are carnitine acetyltransferase (CRAT, also known as CAT), carnitine octanoyltransferase (COT) and carnitine palmitoyltransferase (CPT), with substrate preferences for short-chain, medium-chain and long-chain fatty acids, respectively. These enzymes generally contain approximately 600 amino acid residues and have molecular weights of about 70 kD. They are the products of a multi-gene family which may have evolved by duplication of a single ancestral gene (van der Leij et al., *Mol. Genet. Metab.* 71:139-153 (2000)).

The physiologic relevance of carnitine acyltransferases not only is a source of pathology when these enzymes go awry, but also provides opportunities for treatment of diseases linked with disorders in fatty acid metabolism. The hyperglycemia found in diabetes results from decreased glucose disposal concomitant with increased glucose production, which are often associated with increased and uncontrolled fatty acid oxidation (Bebernitz et al., *Curr. Pharm. Des.* 8:1199-1227 (2002)). Hence, inhibition of fatty acid oxidation has emerged as a new strategy for the treatment of diabetes (Bebernitz et al., *Curr. Pharm. Des.* 8:1199-1227 (2002); Wagman et al., *Curr. Pharm. Des.* 7:417-450 (2001)), in particular non-insulin dependent diabetes mellitus ("NIDDM"; also known as "mature onset diabetes").

Thus, there exists a need for carnitine acyltransferase inhibitors for the treatment of diabetes, obesity, and other diseases that are associated with disorders in fatty acid metabolism. There also exists a need for pharmaceutical compositions comprising carnitine acyltransferase inhibitors. There also exists a need for a method of preparing carnitine acyltransferase inhibitors.

SUMMARY OF THE INVENTION

The present invention relates to β-hydroxy-γ-aminophosphonates and β-amino-γ-aminophosphonates of Formula I and II, or stereoisomers or mixtures of stereoisomers thereof. Compounds of the invention inhibit carnitine acyltransferases. Carnitine acyltransferase inhibitors have shown promise in the treatment, amelioration or prevention of pathological conditions, diseases or disorders that are linked with fatty acid metabolism, including but not limited to, non-insulin dependent diabetes mellitus, obesity, hyperlipoproteinemia, hyperlipidemia, cardiac disorders, e.g., myocardial dysfunction, renal anemia, and Alzheimer's disease.

Thus, in one aspect present invention pertains to β-hydroxy-γ-aminophosphonates and β-amino-γ-aminophosphonates of Formula I:

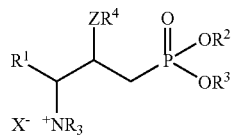

I particularly wherein:

R is selected from the group consisting of hydrogen and lower alkyl;

$R^1$ is selected from the group consisting of hydrogen, optionally substituted alkyl, aralkyl, optionally substituted cycloalkyl, optionally substituted alkenyl, optionally substituted alkynyl, optionally substituted aryl, optionally substituted heteroaryl, and optionally substituted heterocyclo;

$R^2$ and $R^3$ are independently selected from the group consisting of hydrogen, optionally substituted alkyl, aralkyl, optionally substituted aryl, and monovalent pharmaceutically acceptable cation, or taken together $R^2$ and $R^3$ represent a divalent pharmaceutically acceptable cation;

$R^4$ is selected from the group consisting of hydrogen, optionally substituted alkyl, optionally substituted cycloalkyl, optionally substituted alkenyl, optionally substituted alkynyl, and $COR^5$;

$R^5$ is selected from the group consisting of optionally substituted alkyl, aralkyl, optionally substituted cycloalkyl, optionally substituted alkenyl, optionally substituted alkynyl, optionally substituted aryl, optionally substituted heteroaryl, and optionally substituted heterocyclo;

$X^-$ is a pharmaceutically acceptable anion, or $X^-$ and $R^2$ are absent and the compound of Formula I is a zwitterion;

Z is selected from the group consisting of O and $NR^{10}$; and $R^{10}$ is selected from the group consisting of hydrogen, optionally substituted alkyl, aralkyl, optionally substituted cycloalkyl, optionally substituted alkenyl, optionally substituted alkynyl, optionally substituted aryl, optionally substituted heteroaryl, and optionally substituted heterocyclo;

or pharmaceutically acceptable hydrates, crystalline forms or amorphous forms thereof, or a stereoisomer or mixture of stereoisomers thereof.

In additional embodiments, the β-hydroxy-γ-aminophosphonates and β-amino-γ-aminophosphonates of the present invention are compounds selected from the group consisting of Formulae 3S-I; 3R-I; 2R,3S-I; 2S,3S-I; 2R,3R-I; and 2S,3R-I:

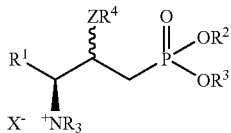

3S-I

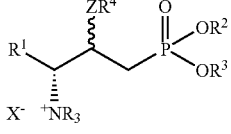

3R-I

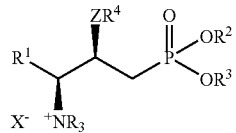

2R,3S-I

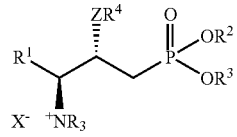

2S,3S-I

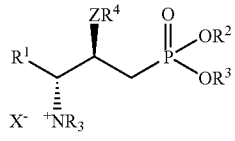

2R,3R-I

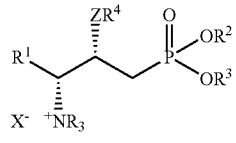

2S,3R-I or pharmaceutically acceptable hydrates, crystalline forms or amorphous forms of anyone thereof, wherein R, $R^1$, $R^2$, $R^3$, $R^4$, $X^-$ and Z have the meanings as described above for Formula I.

In additional embodiments, the β-hydroxy-γ-aminophosphonates and β-amino-γ-aminophosphonates of the present invention are zwitterionic compounds of Formula II:

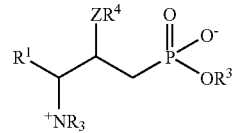

II or pharmaceutically acceptable hydrates, crystalline forms or amorphous forms thereof, wherein R, $R^1$, $R^3$, $R^4$ and Z have the meanings as described above for Formula I.

In additional embodiments, the β-hydroxy-γ-aminophosphonates and β-amino-γ-aminophosphonates of the present invention are zwitterionic compounds selected from the group consisting of Formulae 3S-II; 3R-II; 2R,3S-II; 2S,3S-II; 3R,3R-II; and 2S,3R-II:

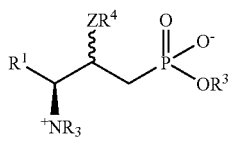

3S-II

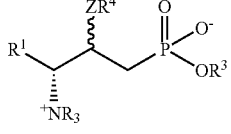

3R-II

-continued

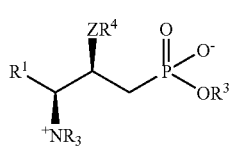
2R,3S-II

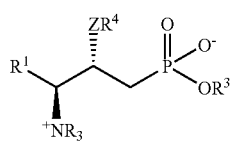
2S,3S-II

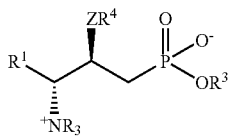
2R,3R-II

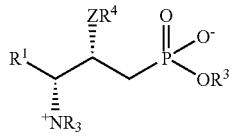
2S,3R-II or pharmaceutically acceptable hydrates, crystalline forms or amorphous forms of anyone thereof, wherein R, $R^1$, $R^3$, $R^4$, and Z have the meanings as described above for Formula I.

The present invention also provides methods for the preparation of a β-hydroxy-γ-aminophosphonate of Formula III:

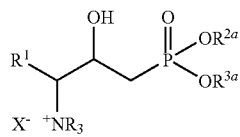
III particularly wherein:
R is selected from the group consisting of hydrogen and lower alkyl;
$R^1$ is selected from the group consisting of hydrogen, optionally substituted alkyl, aralkyl, optionally substituted cycloalkyl, optionally substituted alkenyl, optionally substituted alkynyl, optionally substituted aryl, optionally substituted heteroaryl, and optionally substituted heterocyclo;
$R^{2a}$ and $R^{3a}$ are independently selected from the group consisting of optionally substituted alkyl, aralkyl, and optionally substituted aryl; and
$X^-$ is a pharmaceutically acceptable anion;
the methods comprising:
(a) reacting a compound of Formula IV

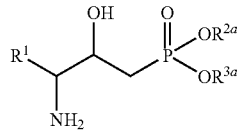
IV with RX, to give a compound of Formula III, or a stereoisomer or mixture of stereoisomers thereof; and (b) isolating said compound of Formula III.

In one such embodiment, a compound of Formula III is a diastereomeric mixture having S-stereochemistry at the 3-position, i.e., a compound of Formula 3S-III:

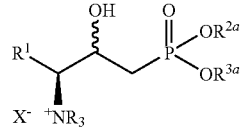
3S-III

In another such embodiment, a compound of Formula III is a diastereomeric mixture having R-stereochemistry at the 3-position, i.e., a compound of Formula 3R-III:

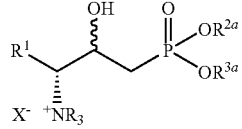
3R-III

In still another such embodiment, a compound of Formula III is in the 2R,3S-isomeric form, i.e., a compound of Formula 2R,3S-III:

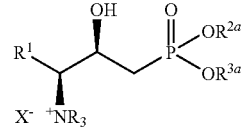
2R,3S-III

In still another such embodiment, a compound of Formula III is in the 2S, 3S-isomeric form, i.e., a compound of Formula 2S,3S-III:

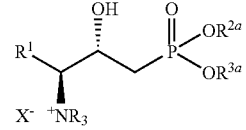
2S,3S-III

In still another such embodiment, a compound of Formula III is in the 2R,3R-isomeric form, i.e., a compound of Formula 2R,3R-III:

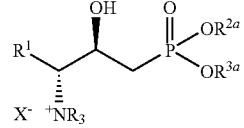
2R,3R-III

In still another such embodiment, a compound of Formula III is the 2S,3R-isomer, i.e., a compound of Formula 2R,3R-III:

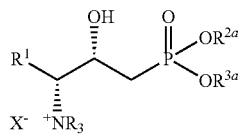

2S,3R-III

The present invention also provides methods for separating the stereoisomers, e.g., diastereomers, of a compound of Formula III. Thus, in one embodiment, the present invention provides methods for the preparation of a compound of Formula 2S,3S-III from a compound of Formula 3S-III, comprising isolating a compound of Formula 2S,3S-III, i.e., the 2S,3S-isomer, substantially free from a compound of Formula 2R,3S-III, i.e., the 2R,3S-isomer. In another embodiment, the invention provides methods for the preparation of a compound of Formula 2R,3S-III from a compound of Formula 3S-III, comprising isolating a compound of Formula 2R,3S-III substantially free from a compound of Formula 2S,3S-III. In another embodiment, the invention provides methods for the preparation of a compound of Formula 2R,3R-III from a compound of Formula 3R-III, comprising isolating a compound of Formula 2R,3R-III, i.e., the 2R,3R-isomer, substantially free from a compound of Formula 2S,3R-III, i.e., the 2S,3R-isomer. In another embodiment, the invention provides methods for the preparation of a compound of Formula 2S,3R-III from a compound of Formula 3R-III, comprising isolating a compound of Formula 2S,3R-III substantially free from a compound of Formula 2R,3R-III.

The present invention also provides methods for the preparation of a compound of Formula IV, the methods comprising:

(a) removing $R^6$, or removing $R^6$ and $R^7$, from a compound of Formula V:

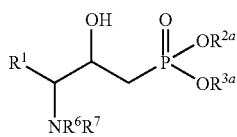

V particularly wherein:

$R^6$ is an amine protecting group; and $R^7$ is selected from the group consisting of hydrogen and an amine protecting group, or $R^6$ and $R^7$ taken together represent an amine protecting group; and $R^1$, $R^{2a}$ and $R^{3a}$ have the meanings as described above for Formula III, to give a compound of Formula IV, or a stereoisomer or mixture of stereoisomers thereof; and (b) isolating said compound of Formula IV; or (c) using said compound of Formula IV in the next reaction without isolation.

In one such embodiment, a compound of Formula V is a diastereomeric mixture having S-stereochemistry at the 3-position, i.e. a compound of Formula 3S-V:

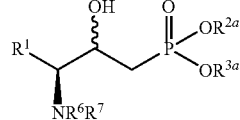

3S-V

In another such embodiment, a compound of Formula V is a diastereomeric mixture having R-stereochemistry at the 3-position, i.e. a compound of Formula 3R-V:

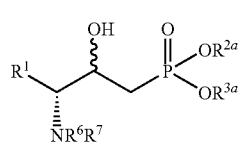

3R-V

The present invention also provides methods for the preparation of a β-hydroxy-γ-aminophosphonate of Formula V; the methods comprising:

(a) reducing a β-keto-γ-aminophosphonate of Formula VI:

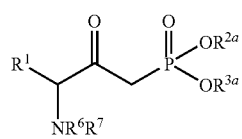

VI particularly wherein $R^1$, $R^{2a}$ and $R^{3a}$ have the meanings as described above for Formula III, and $R^6$ and $R^7$ have the meanings as described above for Formula V, to give a compound of Formula VI, or a stereoisomer or mixture of stereoisomers thereof; and (b) isolating said compound of Formula V; or (c) using said compound of Formula V in the next reaction without isolation.

In one such embodiment, a compound of Formula VI has S-stereochemistry at the 3-position, i.e. a compound of Formula 3S-VI:

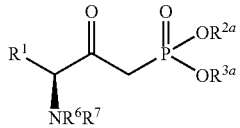

3S-VI

In another such embodiment, a compound of Formula VI has R-stereochemistry at the 3-position, i.e. a compound of Formula 3R-VI:

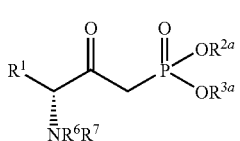

3R-VI

The present invention also provides methods for the preparation of a compound of Formula VI, the methods comprising:

(a) condensing a compound of Formula VII:

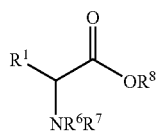
VII with a compound of Formula VIII:

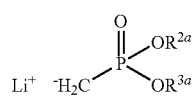
VIII particularly wherein $R^1$, $R^{2a}$ and $R^{3a}$ have the meanings as described above for Formula III, $R^6$ and $R^7$ have the meanings as described above for Formula V, and $R^8$ is selected from the group consisting of optionally substituted alkyl, aralkyl, and optionally substituted aryl, to give a compound of Formula VI, or a stereoisomer or mixture of stereoisomers thereof; and
(b) isolating said compound of Formula VI; or
(c) using said compound of Formula VI in the next reaction without isolation.

In one such embodiment, a compound of Formula VII is the S-isomer, i.e. a compound of Formula S-VII:

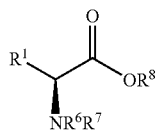
S-VII

In another such embodiment, a compound of Formula VII is the R-isomer, i.e. a compound of Formula R-VII:

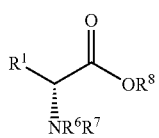
R-VII

The present invention also provides methods for the preparation of a compound of Formula VIII, the methods comprising:
(a) condensing a compound of Formula IX:

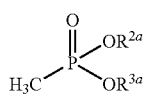
IX with $LiR^9$, particularly wherein $R^{2a}$ and $R^{3a}$ have the meanings as described above for Formula III, and $R^9$ is selected from the group consisting of lower alkyl, and aryl, to give a compound of Formula VIII; and
(b) isolating said compound of Formula VIII; or
(c) using said compound of Formula VIII in the next reaction without isolation.

The present invention also provides methods for the preparation of a compound of Formula X:

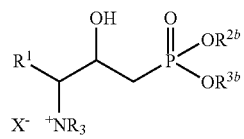
X particularly wherein R and $R^1$ have the meanings as described above for Formula III, $R^{2b}$ and $R^{3b}$ are selected from the group consisting of hydrogen and monovalent pharmaceutically acceptable cation, or taken together $R^{2b}$ and $R^{3b}$ represent a divalent pharmaceutically acceptable cation, or $X^-$ and $R^{2b}$ are absent (i.e., a compound of Formula X is a zwitterion), the methods comprising:
(a) removing $R^{2a}$ and $R^{3a}$ from a compound of Formula III, to give a compound of Formula X, or a stereoisomer or mixture of stereoisomers thereof; and
(b) isolating said compound of Formula X.

In one such embodiment, a compound of Formula X is a diastereomeric mixture having S-stereochemistry at the 3-position, i.e., a compound of Formula 3S-X:

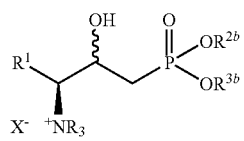
3S-X

In another such embodiment, a compound of Formula X is a diastereomeric mixture having R-stereochemistry at the 3-position, i.e., a compound of Formula 3R-X.

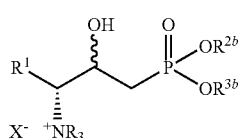
3R-X

In still another such embodiment, a compound of Formula X is in the 2R,3S-isomeric form, i.e., a compound of Formula 2R,3S-X:

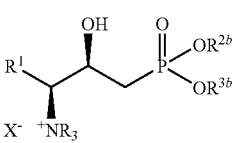
2R,3S-X

In still another such embodiment, a compound of Formula X is in the 2S,3S-isomeric form, i.e., a compound of Formula 2S,3S-X:

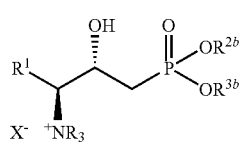

2S,3S-X

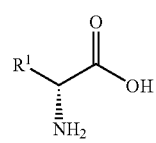

R-XI

In still another such embodiment, a compound of Formula X is in the 2R,3R-isomeric form, i.e., a compound of Formula 2R,3R-X:

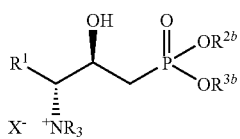

2R,3R-X

In still another such embodiment, a compound of Formula X is in the 2S,3R-isomeric form, i.e., a compound of Formula 2S,3R-X:

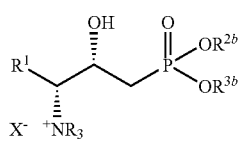

2S,3R-X

The invention also provides methods for the preparation of a compound of Formula VII, the method comprising:
(a) protecting the amine of an amino acid of Formula XI;
(b) esterifying the carboxylic acid of an amino acid of Formula XI:

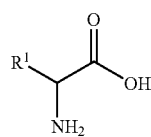

XI particularly wherein $R^1$ has the meaning as described above for Formula III, to give a compound of Formula VII; and
(c) isolating said compound of Formula VII; or
(d) using said compound of Formula VII in the next reaction without isolation.

In one such embodiment, the compound of Formula XI is the S-isomer having Formula S-XI:

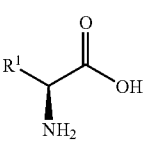

S-XI

In another such embodiment, the compound of Formula XI is the R-isomer having Formula R-XI:

The invention also provides compounds prepared in accordance with the methods of the invention.

The invention also provides pharmaceutical compositions comprising a compound of the invention and a pharmaceutically acceptable carrier.

The invention also provides methods for inhibiting carnitine acyltransferase in a cell comprising contacting said cell with a compound of the invention.

The invention also provides a method of treating, ameliorating, or preventing a disorder or condition responsive to the inhibition of carnitine acyltransferase in a patient in need thereof, comprising administering to the patient a therapeutically effective amount of a compound of the invention.

The invention also provides a method of treating, ameliorating, or preventing a disorder or condition responsive to the inhibition of carnitine acyltransferase in a patient in need thereof, comprising administering to the patient a therapeutically effective amount of a pharmaceutical composition comprising a compound of the invention and one or more additional therapeutic agents.

The invention also provides a method of treating, ameliorating, or preventing a disorder or condition responsive to the inhibition of carnitine acyltransferase in a patient in need thereof, comprising administering to the patient a therapeutically effective amount of a compound of the invention in combination with one or more additional therapeutic agents.

Other features and advantages of the invention will be apparent from the following detailed description, and from the claims. The disclosed materials, methods, and examples are for illustrative purposes only and are not intended to be limiting. Skilled artisans will appreciate that methods and materials similar or equivalent to those described herein can be used to practice the invention.

Unless otherwise defined, all technical and scientific terms used herein have the meaning commonly understood by one skilled in the art to which this invention belongs. All publications, patent applications, patents, and other references mentioned herein are incorporated by reference in their entirety. In case of conflict, the present specification, including definitions, will control.

DETAILED DESCRIPTION OF THE INVENTION

Definitions

Figure 1:
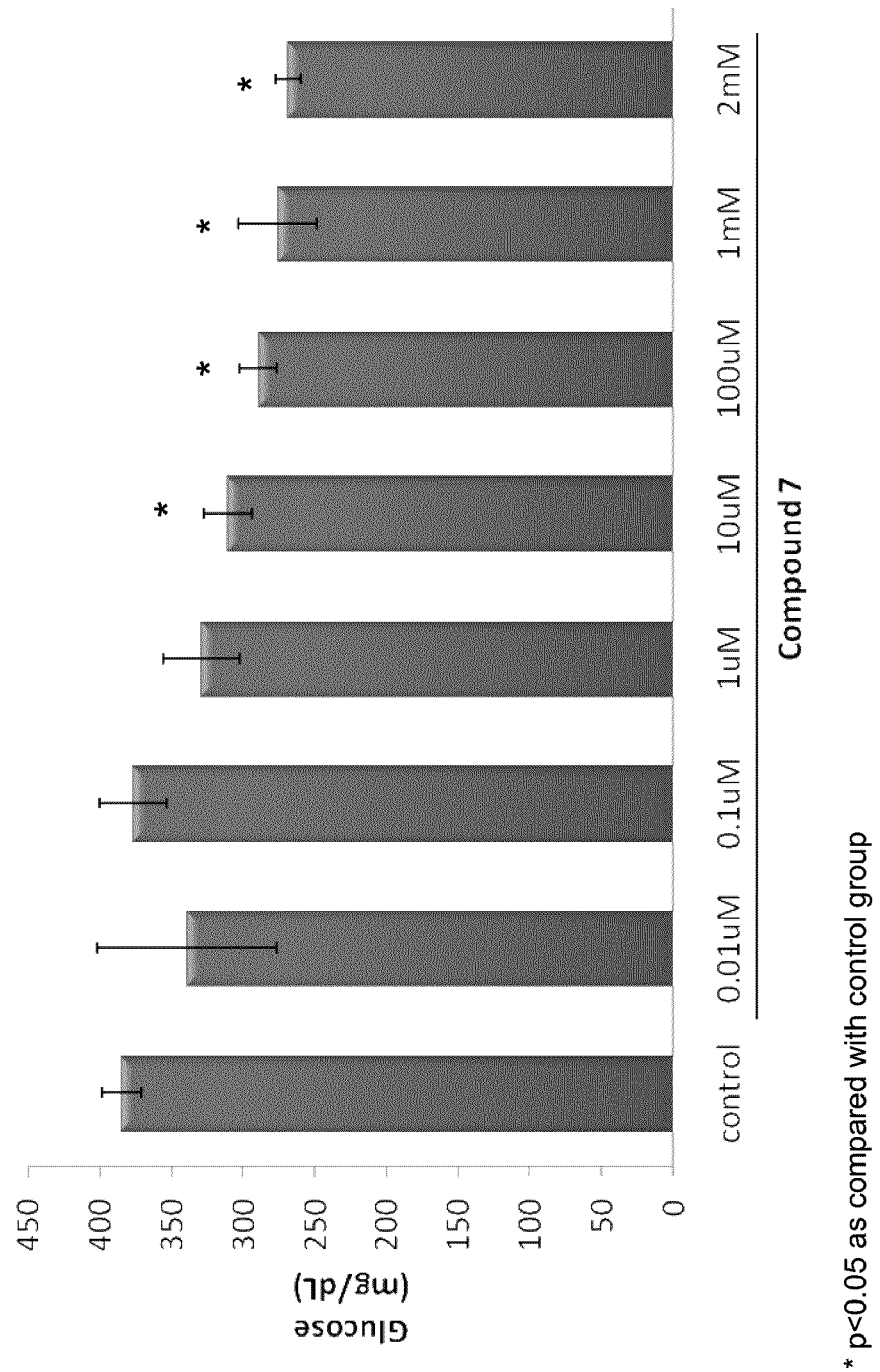
FIG. 1 is a bar graph showing extracellular glucose levels measured in conditioned media of hepatic cells treated with different concentrations of the diastereomeric mixture of compound 7.

The term "alkyl" as used herein by itself or part of another group refers to a straight-chain or branched saturated aliphatic hydrocarbon having from one to eighteen carbons or the number of carbons designated, e.g., $C_1$-$C_{18}$ means from 1 to 18 carbons, inclusive. In one such embodiment, the alkyl is a $C_1$-$C_{10}$ alkyl. In another such embodiment, the alkyl is a $C_1$-$C_8$ alkyl. In certain such embodiments, the alkyl is a lower alkyl. Non-limiting exemplary alkyl groups according to certain aspects of the invention include methyl, ethyl, n-propyl, isopropyl, n-butyl, sec-butyl, isobutyl, tert-butyl, n-pentyl, isopentyl, n-hexyl, isohexyl, n-heptyl, 4,4-dimethylpentyl, n-octyl, 2,2,4-trimethylpentyl, nonyl, decyl, and the like. Other suitable alkyl groups will be familiar to those of ordinary skill in the relevant arts.

The term "lower alkyl" as used herein by itself or part of another group means the alkyl as defined above has 1 to 6 carbons, i.e., a $C_1$-$C_6$-alkyl. Non-limiting exemplary lower alkyl groups include methyl, ethyl, n-propyl, isopropyl, n-butyl, sec-butyl, isobutyl, tert-butyl, n-pentyl, isopentyl, n-hexyl, and the like. Other suitable lower alkyl groups will be familiar to those of ordinary skill in the relevant arts.

The term "optionally substituted alkyl" as used herein by itself or part of another group means that the alkyl as defined above is either unsubstituted or substituted with one, two or three substituents independently selected from hydroxy, i.e., —OH, nitro, i.e., —NO$_2$, cyano, i.e., —CN, halo, amino, optionally substituted cycloalkyl, optionally substituted heteroaryl, optionally substituted heterocyclo, alkoxy, aryloxy, aralkyloxy, alkylthio, carboxamido or sulfonamido. In one such embodiment, the optionally substituted alkyl is unsubstituted. In another such embodiment, the optionally substituted alkyl is substituted with one substituent. In another such embodiment, the optionally substituted alkyl is substituted with two substituents. In certain such embodiments, the substituents are selected from hydroxy, i.e., a hydroxyalkyl, halo, i.e., a haloalkyl, or amino, i.e., an aminoalkyl. In certain such embodiments, the optionally substituted alkyl is an optionally substituted $C_1$-$C_6$-alkyl, i.e., an optionally substituted lower alkyl. Exemplary optionally substituted alkyl groups include, but are not limited to, —CH$_2$OCH$_3$, —CH$_2$CH$_2$NH$_2$, —CH$_2$CH$_2$CN, —CH$_2$CONH$_2$, hydroxymethyl, hydroxyethyl, hydroxypropyl, trifluoromethyl, and the like. Other suitable optionally substituted alkyl groups will be familiar to those of ordinary skill in the relevant arts.

The term "aralkyl" as used herein by itself or part of another group refers to an optionally substituted alkyl as defined above having one, two or three optionally substituted aryl substituents. In one such embodiment, the optionally substituted alkyl is unsubstituted. In another such embodiment, the optionally substituted aryl is unsubstituted. In certain such embodiments, the optionally substituted aryl is phenyl (abbreviated as "Ph"). In another such embodiment, the aralkyl has one optionally substituted aryl substituent. In another such embodiment, the aralkyl has two optionally substituted aryl substituents. In a particular embodiment, the aralkyl is an aryl($C_1$-$C_4$ alkyl). In certain such embodiments, the aryl($C_1$-$C_4$ alkyl) has one optionally substituted aryl substituent. Non-limiting exemplary aralkyl groups include, for example, benzyl, phenylethyl, (4-fluorophenyl)ethyl, phenylpropyl, diphenylmethyl (i.e., Ph$_2$CH—), diphenylethyl (i.e., Ph$_2$CHCH$_2$—), and the like. Other suitable aralkyl groups will be familiar to those of ordinary skill in the relevant arts.

The term "cycloalkyl" as used herein by itself or part of another group refers to saturated and partially unsaturated (containing one or two double bonds) cyclic hydrocarbon groups containing one to three rings having from three to twelve carbon atoms (i.e., $C_3$-$C_{12}$ cycloalkyl) or the number of carbons designated. In one such embodiment, the cycloalkyl has one ring. In another such embodiment, the cycloalkyl is a $C_3$-$C_7$ cycloalkyl. Non-limiting exemplary cycloalkyl groups include cyclopropyl, cyclobutyl, cyclopentyl, cyclohexyl, cycloheptyl, cyclooctyl, norbornyl, decalin, adamantyl, and the like. Other suitable cycloalkyl groups will be familiar to those of ordinary skill in the relevant arts.

The term "optionally substituted cycloalkyl" as used herein by itself or part of another group means the cycloalkyl as defined above is either unsubstituted or substituted with one, two or three substituents independently selected from halo, nitro, cyano, hydroxy, amino, optionally substituted alkyl, haloalkyl, hydroxyalkyl, aralkyl, optionally substituted cycloalkyl, optionally substituted alkenyl, optionally substituted alkynyl, optionally substituted aryl, optionally substituted heteroaryl, optionally substituted heterocyclo, alkoxy, aryloxy, aralkyloxy, alkylthio, carboxamido or sulfonamido. The term "optionally substituted cycloalkyl" also means the cycloalkyl as defined above may be fused to an optionally substituted aryl. Non-limiting exemplary optionally substituted cycloalkyl groups include:

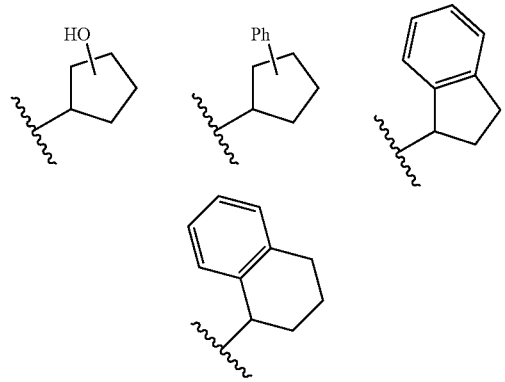

and the like. Other suitable optionally substituted cycloalkyl groups suitable for use in accordance with this aspect of the invention will be familiar to those of ordinary skill in the relevant arts.

The term "alkenyl" as used herein by itself or part of another group refers to an alkyl group as defined above containing one, two or three carbon-to-carbon double bonds. In one embodiment, the alkenyl has one carbon-to-carbon double bond. Non-limiting exemplary alkenyl groups include —CH═CH$_2$, —CH$_2$CH═CH$_2$, —CH$_2$CH$_2$CH═CH$_2$, —CH$_2$CH$_2$CH═CHCH$_3$ and the like. Other suitable alkenyl groups will be familiar to those of ordinary skill in the relevant arts.

The term "optionally substituted alkenyl" as used herein by itself or part of another group means the alkenyl as defined above is either unsubstituted or substituted with one, two or three substituents independently selected from halo, nitro, cyano, hydroxy, amino, optionally substituted alkyl, haloalkyl, hydroxyalkyl, aralkyl, optionally substituted cycloalkyl, optionally substituted alkenyl, optionally substituted alkynyl, optionally substituted aryl, optionally substituted heteroaryl, optionally substituted heterocyclo, alkoxy, aryloxy, aralkyloxy, alkylthio, carboxamido or sulfonamido. Non-limiting exemplary optionally substituted alkenyl groups include —CH=CH—, —CH=CHPh, —CH$_2$CH=CHPh, and the like. Other suitable optionally alkenyl groups will be familiar to those of ordinary skill in the relevant arts.

The term "alkynyl" as used herein by itself or part of another group refers to an alkyl group as defined above containing one to three carbon-to-carbon triple bonds. In one embodiment, the alkynyl has one carbon-to-carbon triple bond. Non-limiting exemplary alkynyl groups include —C≡CH, —C≡CCH$_3$, —CH$_2$C≡CH, —CH$_2$CH$_2$C≡CH and —CH$_2$CH$_2$CCCH$_3$. Other suitable alkynyl groups will be familiar to those of ordinary skill in the relevant arts.

The term "optionally substituted alkynyl" as used herein by itself or part of another group means the alkynyl as defined above is either unsubstituted or substituted with one, two or three substituents independently selected from halo, nitro, cyano, hydroxy, amino, optionally substituted alkyl, haloalkyl, hydroxyalkyl, aralkyl, optionally substituted cycloalkyl, optionally substituted alkenyl, optionally substituted alkynyl, optionally substituted aryl, optionally substituted heteroaryl, optionally substituted heterocyclo, alkoxy, aryloxy, aralkyloxy, alkylthio, carboxamido or sulfonamido. Non-limiting exemplary optionally substituted alkenyl groups include —C≡CPh, —CH$_2$C≡CPh and the like. Other suitable optionally substituted alkynyl groups will be familiar to those of ordinary skill in the relevant arts.

The term "aryl" as used herein by itself or part of another group refers to monocyclic and bicyclic aromatic ring systems having from six to fourteen carbon atoms (i.e., $C_6$-$C_{14}$ aryl) such as phenyl (abbreviated as Ph), 1-naphthyl and 2-naphthyl, and the like. Other aryl groups suitable for use in accordance with this aspect of the invention will be familiar to those of ordinary skill in the relevant arts.

The term "optionally substituted aryl" as used herein by itself or part of another group means the aryl as defined above is either unsubstituted or substituted with one to five substituents independently selected from halo, nitro, cyano, hydroxy, amino, optionally substituted alkyl, haloalkyl, hydroxyalkyl, aralkyl, optionally substituted cycloalkyl, optionally substituted alkenyl, optionally substituted alkynyl, optionally substituted aryl, optionally substituted heteroaryl, optionally substituted heterocyclo, alkoxy, aryloxy, aralkyloxy, alkylthio, carboxamido or sulfonamido. In one such embodiment, the optionally substituted aryl is an optionally substituted phenyl, which in certain embodiments has four substituents, three substituents, two substituents or one substituent. Non-limiting exemplary substituted aryl groups include 2-methylphenyl, 2-methoxyphenyl, 2-fluorophenyl, 2-chlorophenyl, 2-bromophenyl, 3-methylphenyl, 3-methoxyphenyl, 3-fluorophenyl, 3-chlorophenyl, 4-methylphenyl, 4-ethylphenyl, 4-methoxyphenyl, 4-fluorophenyl, 4-chlorophenyl, 2,6-difluorophenyl, 2,6-di-chlorophenyl, 2-methyl, 3-methoxyphenyl, 2-ethyl, 3-methoxyphenyl, 3,4-di-methoxyphenyl, 3,5-di-fluorophenyl 3,5-di-methylphenyl and 3,5-dimethoxy, 4-methylphenyl and the like. As used herein, the term "optionally substituted aryl" is also meant to include groups having fused optionally substituted cycloalkyl and fused optionally substituted heterocyclo rings. Non-limiting exemplary examples include:

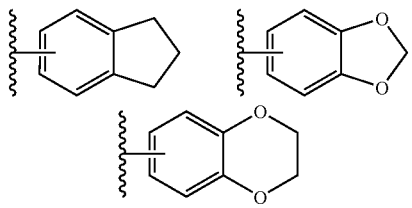

and the like. Additional suitable optionally substituted aryl groups for use in accordance with this aspect of the invention will be familiar to those of ordinary skill in the relevant arts.

The term "heteroaryl" as used herein by itself or part of another group refers to monocyclic and bicyclic aromatic ring systems typically having from five to fourteen carbon atoms (i.e., $C_5$-$C_{14}$ heteroaryl) and one, two, three or four heteroatoms independently selected from the group consisting of oxygen, nitrogen and sulfur. In one such embodiment, the heteroaryl has four heteroatoms. In another such embodiment, the heteroaryl has three heteroatoms. In another such embodiment, the heteroaryl has two heteroatoms. In another such embodiment, the heteroaryl has one heteroatom. Non-limiting exemplary heteroaryl groups include 1-pyrrolyl, 2-pyrrolyl, 3-pyrrolyl, 2-imidazolyl, 4-imidazolyl, pyrazinyl, 2-oxazolyl, 4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl pyrimidyl, 4-pyrimidyl, purinyl, 2-benzimidazolyl, 4-benzimidazolyl, 5-benzimidazolyl, 2-benzthiazolyl, 4-benzthiazolyl, 5-benzthiazolyl, 5-indolyl, 3-indazolyl, 4-indazolyl, 5-indazolyl, 1-isoquinolyl, 5-isoquinolyl, 2-quinoxalinyl, 5-quinoxalinyl, 2-quinolyl, 3-quinolyl, 6-quinolyl and the like. As used herein, the term "heteroaryl" is also meant to include possible N-oxides. Non-limiting exemplary N-oxides include pyridyl N-oxide and the like. Additional suitable heteroaryl groups for use in accordance with this aspect of the invention will be familiar to those of ordinary skill in the relevant arts.

The term "optionally substituted heteroaryl" as used herein by itself or part of another group means the heteroaryl as defined above is either unsubstituted or substituted with one to four substituents, typically one or two substituents, which are typically independently selected from halo, nitro, cyano, hydroxy, amino, optionally substituted alkyl, haloalkyl, hydroxyalkyl, aralkyl, optionally substituted cycloalkyl, optionally substituted alkenyl, optionally substituted alkynyl, optionally substituted aryl, optionally substituted heteroaryl, optionally substituted heterocyclo, alkoxy, aryloxy, aralkyloxy, alkylthio, carboxamido or sulfonamido. In one such embodiment, the optionally substituted heteroaryl has one substituent. According to this aspect of the invention, any available carbon or nitrogen atom may be substituted. Non-limiting exemplary optionally substituted heteroaryl groups include:

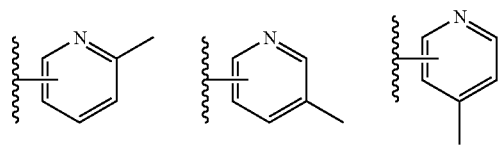

and the like. Additional suitable optionally substituted heteroaryl groups for use in accordance with this aspect of the invention will be familiar to those of ordinary skill in the relevant arts.

The term "heterocyclo" as used herein by itself or part of another group refers to saturated and partially unsaturated (containing one or two double bonds) cyclic groups containing one to three rings having from two to twelve carbon atoms (i.e., $C_2$-$C_{12}$ heterocyclo) and one or two oxygen, sulfur or nitrogen atoms. According to this aspect of the invention, the heterocyclo can be optionally linked to the rest of the molecule through a carbon or nitrogen atom. Non-limiting exemplary heterocyclo groups include:

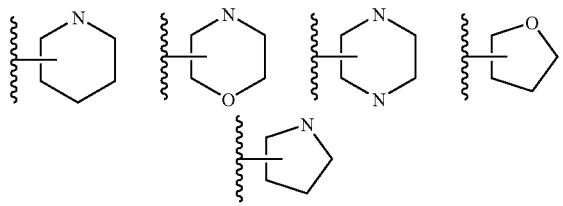

and the like. Additional suitable heterocyclo groups for use in accordance with this aspect of the invention will be familiar to those of ordinary skill in the relevant arts.

The term "optionally substituted heterocyclo" as used herein by itself or part of another group means the heterocyclo as defined above is either unsubstituted or substituted with one to four substituents which are typically independently selected from halo, nitro, cyano, hydroxy, amino, optionally substituted alkyl, haloalkyl, hydroxyalkyl, aralkyl, optionally substituted cycloalkyl, optionally substituted alkenyl, optionally substituted alkynyl, optionally substituted aryl, optionally substituted heteroaryl, optionally substituted heterocyclo, alkoxy, aryloxy, aralkyloxy, alkylthio, carboxamido or sulfonamido. Substitution may occur on any available carbon or nitrogen atom. Non-limiting exemplary substituted heterocyclo groups include:

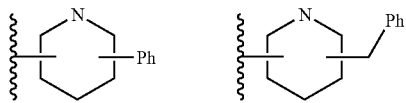

and the like. In certain embodiments of the invention, an optionally substituted heterocyclo may be fused to an aryl group to provide an optionally substituted aryl as described above.

The term "alkoxy" as used herein by itself or part of another group refers to a haloalkyl, optionally substituted alkyl, optionally substituted cycloalkyl, optionally substituted alkenyl or optionally substituted alkynyl attached to a terminal oxygen atom. Non-limiting exemplary alkoxy groups include methoxy, tert-butoxy, —OCH$_2$CH=CH$_2$ and the like.

The term "aryloxy" as used herein by itself or part of another group refers to an optionally substituted aryl attached to a terminal oxygen atom. Non-limiting exemplary aryloxy groups include phenoxy and the like.

The term "aralkyloxy" as used herein by itself or part of another group refers to an aralkyl attached to a terminal oxygen atom. Non-limiting exemplary aralkyloxy groups include benzyloxy and the like.

The term "alkylthio" as used herein by itself or part of another group refers to a haloalkyl, aralkyl, optionally substituted alkyl, optionally substituted cycloalkyl, optionally substituted alkenyl or optionally substituted alkynyl attached to a terminal sulfur atom. Non-limiting exemplary alkyl groups include —SCH$_3$ and the like.

The term "halo" or "halogen" as used herein by itself or part of another group refers to fluoro, chloro, bromo or iodo. In certain embodiments of the present invention, the halo is fluoro or chloro.

The term "amino" as used herein by itself or part of another group refers to a radical of formula —NR$^a$R$^b$ wherein R$^a$ and R$^b$ are independently hydrogen, haloalkyl, aralkyl, optionally substituted alkyl, optionally substituted cycloalkyl, optionally substituted heterocyclo, optionally substituted aryl or optionally substituted heteroaryl; or R$^a$ and R$^b$ taken together with the nitrogen atom to which they are attached form a four to seven membered optionally substituted heterocyclo. Non-limiting exemplary amino groups include —NH$_2$, —N(H)CH$_3$, —N(CH$_3$)$_2$, N(H)CH$_2$CH$_3$, N(CH$_2$CH$_3$), —N(H)CH$_2$Ph and the like.

The term "carboxamido" as used herein by itself or part of another group refers to a radical of formula —CO-amino. Non-limiting exemplary carboxamido groups include —CONH$_2$, —CON(H)CH$_3$, —CON(H)Ph, —CON(H)CH$_2$CH$_2$Ph, —CON(CH$_3$)$_2$, CON(H)CHPh$_2$ and the like.

The term "sulfonamido" as used herein by itself or part of another group refers to a radical of formula —SO$_2$-amino. Non-limiting exemplary sulfonamido groups include —SO$_2$NH$_2$, —SO$_2$N(H)CH$_3$, —SO$_2$N(H)Ph and the like.

The term "about," as used herein, includes the recited number ±10%. Thus, "about 10" means 9 to 11, inclusive.

The term "leaving group" as used herein refers to an atom or group that becomes detached from an atom or group in what is considered to be the residual or main part of the substrate in a specified reaction. In amide coupling reactions, exemplary leaving groups (i.e., leaving groups designated L$^1$) include —F, —Cl, —Br, —OH, —OC$_6$F$_5$, —O(CO)alkyl and the like. In one embodiment, the leaving group, L$^1$, is —Cl. In another embodiment, the leaving group, L$^1$, is an activated form of —OH (e.g., OBt, O-acylisourea). In certain such embodiments of the invention, an activating agent (e.g., dicyclohexylcarbodiimide (DCC), 1-ethyl-3-(3- dimethylaminopropyl)carbodiimide (EDC), benzotriazol-1-yloxy)tripyrrolidinophosphonium hexafluorophosphate (PyBop)) may be employed to active a carboxylic acid (i.e., the leaving group is —OH) toward amide formation. Such activating agents are well known to those of skill in the art of organic synthesis. Other additives, such as N-hydroxybenzotriazole (HOBt) or N-hydroxysuccinimide (HOSu), may also be added to optimize reaction parameters (e.g., rate, yield, purity, racemization). In nucleophilic displacement reactions (e.g., S$_N$2 reactions), exemplary leaving groups (i.e., leaving groups designated L$^2$) include Cl, —Br, —I, —OSO$_2$Me (mesylate), —OSO$_2$CF$_3$ (triflate), OSO$_2$C$_6$H$_5$ (besylate), —OSO$_2$CH$_3$C$_6$H$_4$ (tosylate) and the like. In one embodiment, the leaving group, L$^2$, is —OSO$_2$CF$_3$ or —I In another embodiment, the leaving group, L$^2$, is —OSO$_2$CF$_3$. In another embodiment, the leaving group L$^2$ is —I.

The term "amine protecting group" as used herein refers to group that blocks (i.e., protects) the amine functionality while reactions are carried out on other functional groups or parts of the molecule. Those skilled in the art will be familiar with the selection, attachment, and cleavage of amine protecting groups and will appreciate that many different protective groups are known in the art, the suitability of one protective group or another being dependent on the particular the synthetic scheme planned. Treatises on the subject are available for consultation, such as Greene and Wuts, "Protective Groups in Organic Synthesis," 3rd Ed., pp. 17-245 (J. Wiley & Sons, 1999), the disclosure of which is incorporated herein by reference. Suitable amine protecting groups include the carbobenzyloxy (Cbz), tert-butyloxycarbonyl (BOC), 9-fluorenylmethyloxycarbonyl (FMOC), phthalimide and benzyl (Bn) groups. With regard to a compound of Formula VII, in one such embodiment, the amine protecting group, $R^6$, is the carbobenzyloxy or tert-butyloxycarbonyl, and $R^7$ is hydrogen. In another such embodiment, the amine protecting groups, $R^6$ and $R^7$, are benzyl. In another such embodiment, $R^6$ and $R^7$ taken together form an amine protecting group, such as a phthalimide group.

The term "$C_1$-$C_4$ alcohol" as used herein refers to an alcohol having 1 to 4 carbons such as methanol, ethanol, propanol, isopropanol, butanol, isobutanol, sec-butanol and tert-butanol. In one embodiment, the $C_1$-$C_4$ alcohol is methanol.

The term "monovalent pharmaceutically acceptable cation" as used herein refers to inorganic cations such as, but not limited to, alkaline metal ions, e.g., $Na^+$ and $K^-$, as well as organic cations such as, but not limited to, ammonium and substituted ammonium ions, e.g., $NH_4^+$, $NHMe_3^+$, $NH_2Me_2^+$, $NHMe_3^+$ and $NMe_4^+$.

The term "divalent pharmaceutically acceptable cation" as used herein refers to inorganic cations such as, but not limited to, alkaline earth metal cations, e.g., $Ca^{2+}$ and $Mg^{2+}$.

Examples of monvalent and divalent pharmaceutically acceptable cations are discussed in Berge et al. *J. Pharm. Sci.*, 66, 1997, 1-19, the disclosure of which is incorporated herein by reference.

The term "pharmaceutically acceptable anion" as used herein refers to an anion associated with a quaternary ammonium compound of the present invention that is acceptable for administration to a patient, e.g., a mammal, e.g., a human. In one embodiment, the pharmaceutically acceptable anion is the anion of a pharmaceutically acceptable inorganic acid, e.g., hydrochloric, perchloric, sulfuric, phosphoric, hydrobromic, hydroiodic or nitric acid and the like. In one embodiment, the pharmaceutically acceptable anion is the anion of a pharmaceutically acceptable organic acid, e.g., a mono or polyvalent organic acid, e.g., citric, fumaric, maleic, malic, ascorbic, succinic, tartaric, benzoic, acetic, phenylacetic, methanesulfonic, ethansulfonic, benzenesulfonic or p-toluenesulfonic acid and the like.

The term "pharmaceutically acceptable salt," as used herein, refers to any salt (e.g., obtained by reaction with an acid or a base) of a compound of the present invention that is physiologically tolerated in the target animal (e.g., a mammal, such as a human). Salts of the compounds of the present invention may be derived from inorganic or organic acids and bases. Examples of suitable acids include, but are not limited to, hydrochloric, hydrobromic, sulfuric, nitric, perchloric, fumaric, maleic, phosphoric, glycolic, lactic, salicylic, succinic, toluene-p-sulfonic, tartaric, acetic, citric, methanesulfonic, ethansulfonic, formic, benzoic, boronic, malonic, sulfonic, picolinic, naphthalene-2-sulfonic, benzenesulfonic acid, and the like. Other acids, such as oxalic, while not in themselves pharmaceutically acceptable, may be employed in the preparation of salts useful as intermediates in obtaining the compounds of the invention and their pharmaceutically acceptable acid addition salts.

Examples of suitable bases include, but are not limited to, alkali metal (e.g., sodium) hydroxides, alkaline earth metal (e.g., magnesium) hydroxides, ammonia, and compounds of formula $NW_4^+$, wherein W is $C_{1-4}$ alkyl, and the like.

Examples of suitable such salts include, but are not limited to: acetate, adipate, alginate, aspartate, benzoate, benzenesulfonate, bisulfate, borate, boronate, butyrate, citrate, camphorate, camphorsulfonate, cyclopentanepropionate, digluconate, dodecylsulfate, ethanesulfonate, fumarate, flucoheptanoate, glycerophosphate, hemisulfate, heptanoate, hexanoate, chloride, bromide, iodide, 2-hydroxyethanesulfonate, lactate, maleate, mesylate, methanesulfonate, 2-naphthalenesulfonate, nicotinate, oxalate, palmoate, pectinate, persulfate, phenylpropionate, picrate, pivalate, propionate, succinate, tartrate, thiocyanate, tosylate, undecanoate, nitrate, sulfate, picolinate, besylate, perchloriate, salicylate, phosphate, and the like. Other examples of suitable salts according to the invention include anions of the compounds of the present invention compounded with a suitable cation such as $Na^+$, $K_+$, $Ca^{2+}$, $Mg^{2+}$, $Mn^{2+}$, $NH_4^+$, and $NW_4^+$ (wherein W is a $C_{1-4}$ alkyl group), and the like, including additional pharmaceutically acceptable salts that are well known in the art (see, e.g., Remington's Pharmaceutical Sciences, Mack Publishing Co., Easton, Pa., 19th ed. 1995) and others that are known to those of ordinary skill in the relevant arts. For therapeutic use, salts of the compounds of the present invention are contemplated as being pharmaceutically acceptable. However, salts of acids and bases that are non-pharmaceutically acceptable may also find use, for example, in the preparation or purification of a pharmaceutically acceptable compound.

The term "one pot process" as used herein refers to a strategy to improve the efficiency of a compound synthesis whereby a reactant is subjected to successive chemical reactions in one reactor or reaction vessel. Use of this process potentially avoids the need for lengthy separation processes and purification of the synthetic intermediates. In addition, a one pot process may increase chemical yield. The chemical conversion of leucine to (3-trimethylamonium-2-hydroxy-5-methyl-hexyl)-phosphonic acid dimethyl ester; iodide without isloation and/or purification of any synthetic intermediates is an example of a one pot process.

The term "pharmaceutical composition" as used herein refers to a composition comprising one or more active pharmaceutical ingredients including, but not limited to, one or more compounds of the invention which can be used to treat, prevent or reduce the severity of a disease, disorder or condition in a subject, e.g., a mammal such as a human, that is suffering from, that is predisposed to, or that has been exposed to the disease, disorder or condition. A pharmaceutical composition generally comprises an effective amount of one or more active agents, e.g., a compound of the present invention such as a compound of Formula I or II, or a stereoisomer or mixture of stereoisomers thereof, and a pharmaceutically acceptable carrier. The pharmaceutical composition can also a comprise a compound of the invention and one or more additional ingredients, including but not limited to one or more therapeutic agents such as one or more anticholesterolemics, one or more statins, e.g., atorvastatin, lovastatin, pravastatin, rosuvastatin, fluvastatin or simvastatin, one or more anticoagulants, e.g., warfarin, one or more anti-obesity drugs, e.g., orlistat or sibutramine, or one or more anti-diabetic drugs, such as one or more sulfonylureas, e.g., glimepiride, glibenclamide, one or more biguanides, e.g., metformin, or one or more glitazones, e.g., pioglitazone or rosiglitazone.

The term "pharmaceutically acceptable carrier" encompasses any of the standard pharmaceutical carriers, buffers and excipients, including phosphate-buffered saline solution, water, and emulsions (such as an oil/water or water/oil emulsion), and various types of wetting agents and/or adjuvants. Suitable pharmaceutical carriers and their formulations are described in Remington's Pharmaceutical Sciences, Mack Publishing Co., Easton, Pa., 19th ed. 1995. Preferred pharmaceutical carriers depend upon the intended mode of administration of the active agent. Typical modes of administration are described below.

The term "therapeutically effective amount," as used herein, refers to that amount of a given therapeutic agent sufficient to result in amelioration of one or more symptoms of a disorder or condition, or prevent appearance or advancement of a disorder or condition, or cause regression of or cure from the disorder or condition.

The term "therapeutic agent," as used herein refers to any chemical substance that can be used in the treatment, management, prevention or amelioration of a disease, condition or disorder or one or more symptoms thereof. Suitable therapeutic agents include, but are not limited to, small molecules, synthetic drugs, peptides, polypeptides, proteins, nucleic acids (e.g., DNA and RNA polynucleotides including, but not limited to, antisense nucleotide sequences, triple helices, and nucleotide sequences encoding biologically active proteins, polypeptides, or peptides), antibodies, synthetic or natural inorganic molecules, mimetic agents, and synthetic or natural organic molecules. In some embodiments, the therapeutic agent is one which is known to be useful for, or has been or is currently being used for, the treatment, management, prevention or amelioration of a condition or disorder or one or more symptoms thereof The term "borohydride reducing agent" as used herein refers to a borohydride-based reducing agent capable of reducing a ketone to a secondary alcohol, e.g., sodium borohydride, lithium borohydride, borane, etc. In one embodiment, the borohydride reducing agent is sodium borohydride.

The stereochemical terms and conventions used in the specification are consistent with those described in *Pure & Appl. Chem* 68:2193 (1996), unless otherwise indicated.

The term "purity," as used herein, refers to chemical and/or stereoisomeric (i.e., diastereomeric or enantiomeric) purity, unless otherwise indicated.

The term "enantiomeric excess" or "ee" refers to a measure for how much of one enantiomer is present compared to the other. For a mixture of R and S enantiomers, the percent enantiomeric excess is defined as |R−S|*100, where R and S are the respective mole or weight fractions of enantiomers in a mixture such that R+S=1. With knowledge of the optical rotation of a chiral substance, the percent enantiomeric excess is defined as $([\alpha]_{obs}/[\alpha]_{max})*100$, where $[\alpha]_{obs}$ is the optical rotation of the mixture of enantiomers and $[\alpha]_{max}$ is the optical rotation of the pure enantiomer.

The term "diastereomeric excess" or "de" refers to a measure for how much of one diastereomer is present compared to the other and is defined by analogy to enantiomeric excess. Thus, for a mixture of diastereomers, D1 and D2, the percent diastereomeric excess is defined as |D1−D2|*100, where D1 and D2 are the respective mole or weight fractions of diastereomers in a mixture such that D1+D2=1.

The determination of diastereomeric and/or enantiomeric excess is possible using a variety of analytical techniques, including NMR spectroscopy, chiral column chromatography and/or optical polarimetry according to routine protocols will be familiar to those of ordinary skill in the art.

The term "substantially free," as used herein, refers to a composition comprising at least about 90% by weight of one stereoisomer, i.e., enantiomer or diastereomer, over the corresponding stereoisomer. In another embodiment, the composition comprises at least about 91%, about 92%, about 93%, about 94%, about 95%, about 96%, about 97%, about 98%, about 99% or about 99.5% by weight of the desired stereoisomer. Thus, the term "a compound of Formula 2S,3S-III substantially free from a compound of Formula 2R,3S-III," as used herein, refers to a composition comprising at least about 90% of a compound of Formula 2S,3S-III and at most about 10% of a compound of Formula 2R,3S-III. Similarly, the term "a compound of Formula 2R,3S-III substantially free from a compound of Formula 2S,3S-III," as used herein, refers to a composition comprising at least about 90% of a compound of Formula 2R,3S-III and at most about 10% of a compound of Formula 2S,3S-III.

The term "anti-solvent" as used herein refers to a solvent that reduces the solubility of a solute, e.g., a compound of Formula III, in a solution thereby facilitating precipitation, i.e., crystal growth. In one embodiment, the anti-solvent is selected from the group consisting of hexane, ethyl acetate, acetone, methyl ethyl ketone and methyl t-butyl ether.

Throughout the specification, groups and optional substituents thereof are chosen to provide stable moieties and compounds.

Compounds of the present invention exist as stereoisomers including optical isomers. The invention includes all stereoisomers, as pure individual stereoisomer preparations and as enriched preparations of each, and as the racemic mixtures of such stereoisomers as well as the individual enantiomers and diastereomers that may be separated according to methods that are well-known to those of skill in the art.

Overview

The present invention provides β-hydroxy-γ-aminophosphonates and β-amino-γ-aminophosphonates, or stereoisomers or mixtures of stereoisomers thereof, that inhibit carnitine acyltransferases. Thus, compounds of the invention are useful for the treatment, amelioration or prevention of pathological conditions, diseases or disorders that are linked with fatty acid metabolism, including but not limited to, non-insulin dependent diabetes mellitus, obesity, hyperlipoproteinemia, hyperlipidemia, cardiac disorders, e.g., myocardial dysfunction, renal anemia, and Alzheimer's disease. The present invention also provides pharmaceutical compositions comprising one or more compounds of the invention, and optionally, one or more additional therapeutic agents. The present invention also provides methods of treating, ameliorating, or preventing a disorder or condition responsive to the inhibition of carnitine acyltransferase in a patient, comprising administering to the patient a therapeutically effective amount of a compound of the invention, and optionally one or more additional therapeutic agents. The present invention also provides methods for the preparation of β-hydroxy-γ-aminophosphonates and β-amino-γ-aminophosphonates, or stereoisomers or mixtures of stereoisomers thereof.

Thus, in one embodiment, the present invention provides β-hydroxy-γ-aminophosphonates and β-amino-γ-aminophosphonates of Formula I:

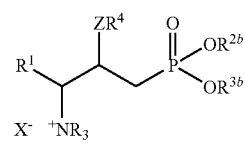

I particularly wherein:

R is selected from the group consisting of hydrogen and lower alkyl;

R¹ is selected from the group consisting of hydrogen, optionally substituted alkyl, aralkyl, optionally substituted cycloalkyl, optionally substituted alkenyl, optionally substituted alkynyl, optionally substituted aryl, optionally substituted heteroaryl, and optionally substituted heterocyclo;

$R^2$ and $R^3$ are independently selected from the group consisting of hydrogen, optionally substituted alkyl, aralkyl, optionally substituted aryl, and monovalent pharmaceutically acceptable cation, or taken together $R^2$ and $R^3$ represent a divalent pharmaceutically acceptable cation;

$R^4$ is selected from the group consisting of hydrogen, optionally substituted alkyl, optionally substituted cycloalkyl, optionally substituted alkenyl, optionally substituted alkynyl, and $COR^5$;

$R^5$ is selected from the group consisting of optionally substituted alkyl, aralkyl, optionally substituted cycloalkyl, optionally substituted alkenyl, optionally substituted alkynyl, optionally substituted aryl, optionally substituted heteroaryl, and optionally substituted heterocyclo;

$X^-$ is a pharmaceutically acceptable anion, or $X^-$ and $R^2$ are absent and the compound of Formula I is a zwitterion, Z is selected from the group consisting of O and $NR^{10}$; and $R^{10}$ is selected from the group consisting of hydrogen, optionally substituted alkyl, aralkyl, optionally substituted cycloalkyl, optionally substituted alkenyl, optionally substituted alkynyl, optionally substituted aryl, optionally substituted heteroaryl, and optionally substituted heterocyclo;

or pharmaceutically acceptable hydrates, crystalline forms or amorphous forms thereof, or a stereoisomer or mixture of stereoisomers thereof.

In one embodiment, a compound of Formula I is a mixture of stereoisomers, e.g., a mixture of diastereomers and/or enantiomers. In another embodiment, a compound of Formula I is a mixture of diastereomers. In another embodiment, a compound of Formula I is a mixture of enantiomers. In another embodiment, a compound of Formula I is a single enantiomer.

In another particular embodiment, β-hydroxy-γ-aminophosphonates and β-amino-γ-aminophosphonate analogs of the present invention are compounds selected from the group consisting of Formula 3S-I; 3R-I; 2R,3S-I;, 2S,3S-I; 2R,3R-I; and 2S,3R-I:

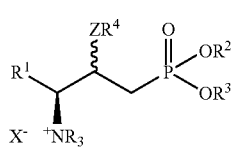

3S-I

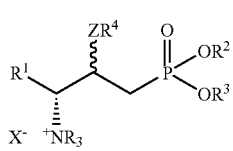

3R-I

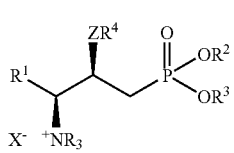

2R,3S-I

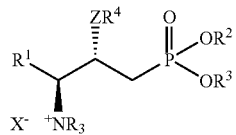

2S,3S-I

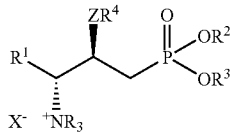

2R,3R-I

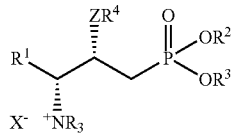

2S,3R-I or pharmaceutically acceptable hydrates, crystalline forms or amorphous forms of any one thereof, particularly wherein R, $R^1$, $R^2$, $R^3$, $R^4$, $X^-$ and Z have the meanings as described above for Formula I.

In one embodiment, β-hydroxy-γ-aminophosphonate or β-amino-γ-aminophosphonate of the present invention is a compound of Formula 3S-I, i.e., a diastereomeric mixture having S-stereochemistry at the 3-position, i.e., the γ-position. In another embodiment, a β-hydroxy-γ-aminophosphonate or β-amino-γ-aminophosphonate analog of the present invention is a compound of Formula 3R-I, i.e., a diastereomeric mixture having R-stereochemistry at the 3-position. In another embodiment, a β-hydroxy-γ-aminophosphonate or β-amino-γ-aminophosphonate analog of the present invention is a compound of Formula 2R,3S-I, i.e., the 2R,3S-isomer. In another embodiment, a β-hydroxy-γ-aminophosphonate or β-amino-γ-aminophosphonate analog of the present invention is a compound of Formula 2S,3S-I, i.e., the 2S,3S-isomer. In another embodiment, a β-hydroxy-γ-aminophosphonate or β-amino-γ-aminophosphonate analog of the present invention is a compound of Formula 2R,3R-I, i.e., the 2R,3R-isomer. In another embodiment, a β-hydroxy-γ-aminophosphonate or β-amino-γ-aminophosphonate analog of the present invention is a compound of Formula 2S,3R-I, i.e., the 2S,3R-isomer.

In certain such embodiments, a compound of Formula I, or a stereoisomer or mixture of stereoisomers thereof, has purity of about 90% or more, e.g., about 91%, about 92%, about 93%, about 94%, about 95%, about 96%, about 97%, about 98%, about 99%, about 99.5% or more.

As it relates to a compound of Formula I, or a stereoisomer or a mixture of stereoisomers thereof, e.g., a compound of Formulae 3S -I; 3R-I; 2R,3S -I; 2S ,3S -I; 2R,3R-I; or 2S,3R-I; in one embodiment, R is lower alkyl. In another such embodiment, R is methyl.

In additional embodiments, $R^1$ is selected from the group consisting of hydrogen, optionally substituted lower alkyl, aralkyl, and optionally substituted aryl. In additional embodiments, $R^1$ is selected from the group consisting of lower alkyl, aralkyl, and optionally substituted aryl. In certain such embodiments, $R^1$ is selected from the group consisting of methyl, ethyl, n-propyl, isopropyl, n-butyl, isobutyl, sec-butyl, tert-butyl, benzyl, and phenyl. In another embodiment, $R^1$ is isobutyl.

In additional embodiments, $R^2$ and $R^3$ are independently selected from the group consisting of hydrogen, optionally substituted lower alkyl, aralkyl and optionally substituted aryl. In certain such embodiments, $R^2$ and $R^3$ are independently selected from the group consisting of hydrogen, lower alkyl, aralkyl, and aryl. In certain such embodiments, $R^2$ and $R^3$ are independently selected from the group consisting of hydrogen, methyl, ethyl, n-propyl, isopropyl, n-butyl, isobutyl, sec-butyl, tert-butyl, isopenyl, benzyl, and phenyl. In additional embodiments, $R^2$ and $R^3$ are independently selected from the group consisting of hydrogen and methyl. In another embodiment, $R^2$ and $R^3$ are hydrogen.

In another embodiment, $R^2$ is a monovalent pharmaceutically acceptable cation and $R^3$ is selected from the group consisting of hydrogen, optionally substituted alkyl, aralkyl, and optionally substituted aryl. In one such embodiment, the monovalent pharmaceutically acceptable cation is selected from the group consisting of $Na^+$ and $K^+$.

In additional embodiments, $R^2$ and $R^3$ are each a monovalent pharmaceutically acceptable cation. In one such embodiment, the monovalent pharmaceutically acceptable cation is selected from the group consisting of $Na^+$ and $K^+$.

In additional embodiments, $R^2$ and $R^3$ taken together represent a divalent pharmaceutically acceptable cation. In one such embodiment, the divalent pharmaceutically acceptable cation is selected from the group consisting of $Mg^{2+}$ and $Ca^{2+}$.

In additional embodiments, $R^4$ is selected from the group consisting of hydrogen, optionally substituted lower alkyl, and $COR^5$. In one such embodiment, $R^4$ is hydrogen. In another such embodiment, $R^4$ is optionally substituted lower alkyl. In still another such embodiment, $R^4$ is lower alkyl. In additional such embodiments, $R^4$ is $COR^5$. In one such embodiment, $R^5$ is optionally substituted lower alkyl. In another such embodiment, $R^5$ is lower alkyl, such as methyl, ethyl, propyl or butyl.

In additional embodiments, $X^-$ is a pharmaceutically acceptable anion which in certain embodiments is selected from the group consisting of hydroxide, chloride, bromide, iodide, sulphate, nitrate, phosphate, formate, acetate, maleate, fumarate, citrate, oxalate, succinate, tartrate, malate, mandelate, lactate, gluconate, trifluoroacetate, methanesulphonate, besylate and p-toluenesulphonate. In one such embodiment, $X^-$ is a pharmaceutically acceptable anion selected from the group consisting of hydroxide, chloride, bromide and iodide.

In additional embodiments, $X^-$ and $R^2$ are absent and the compound of Formula I is a zwitterion.

In additional embodiments, Z is $NR^{10}$. In one such embodiment, $R^{10}$ is selected from the group consisting of hydrogen and optionally substituted lower alkyl, particularly hydrogen.

In additional embodiments, Z is O.

In additional embodiments, R is lower alkyl and $R^1$ is selected from the group consisting of optionally substituted lower alkyl, aralkyl, and optionally substituted aryl. In one such embodiment, R is methyl and $R^1$ is selected from the group consisting of lower alkyl, aralkyl, and optionally substituted aryl. In another such embodiment, R is methyl and $R^1$ is selected from the group consisting of methyl, ethyl, n-propyl, isopropyl, n-butyl, isobutyl, sec-butyl, tert-butyl, benzyl, and phenyl. In another such embodiment, R is methyl and $R^1$ is isobutyl.

In additional embodiments, R is lower alkyl, $R^1$ is selected from the group consisting of optionally substituted lower alkyl, aralkyl, and optionally substituted aryl, and $R^2$ and $R^3$ are independently selected from the group consisting of hydrogen, optionally substituted lower alkyl, aralkyl, and optionally substituted aryl. In one such embodiment, R is methyl, $R^1$ is selected from the group consisting of optionally substituted lower alkyl, aralkyl, and optionally substituted aryl, and $R^2$ and $R^3$ are independently selected from the group consisting of hydrogen, optionally substituted lower alkyl, aralkyl, and optionally substituted aryl. In another such embodiment, R is methyl, $R^1$ is selected from the group consisting of methyl, ethyl, n-propyl, isopropyl, n-butyl, isobutyl, sec-butyl, tert-butyl, benzyl, and phenyl, and $R^2$ and $R^3$ are independently selected from the group consisting of hydrogen, methyl, ethyl, n-propyl, isopropyl, n-butyl, isobutyl, sec-butyl, tert-butyl, isopenyl, benzyl and phenyl. In another such embodiment, R is methyl, $R^1$ is isobutyl and $R^2$ and $R^3$ are selected from the group consisting of hydrogen or methyl. In another such embodiment, R is methyl, $R^1$ is isobutyl and $R^2$ and $R^3$ are hydrogen.

In additional embodiments, R is lower alkyl, $R^1$ is selected from the group consisting of lower alkyl, aralkyl, and optionally substituted aryl, $R^2$ and $R^3$ are independently selected from the group consisting of hydrogen, optionally substituted lower alkyl, aralkyl, and optionally substituted aryl, and $R^4$ is selected from the group consisting of hydrogen and $COR^5$. In one such embodiment, R is lower alkyl, $R^1$ is selected from the group consisting of lower alkyl, aralkyl, and optionally substituted aryl, $R^2$ and $R^3$ are independently selected from the group consisting of hydrogen, optionally substituted lower alkyl, aralkyl, and optionally substituted aryl, and $R^4$ is hydrogen. In another such embodiment, R is methyl, $R^1$ is selected from the group consisting of lower alkyl, aralkyl, and optionally substituted aryl, $R^2$ and $R^3$ are independently selected from the group consisting of hydrogen, optionally substituted lower alkyl, aralkyl, and optionally substituted aryl, and $R^4$ is selected from the group consisting of hydrogen and $COR^5$. In another such embodiment, R is methyl, $R^1$ is selected from the group consisting of lower alkyl, aralkyl, and optionally substituted aryl, $R^2$ and $R^3$ are independently selected from the group consisting of hydrogen, optionally substituted lower alkyl, aralkyl and optionally substituted aryl, and $R^4$ is hydrogen. In another such embodiment, R is methyl, $R^1$ is selected from the group consisting of methyl, ethyl, n-propyl, isopropyl, n-butyl, isobutyl, sec-butyl, tert-butyl, benzyl, and phenyl, $R^2$ and $R^3$ are independently selected from the group consisting of hydrogen, methyl, ethyl, n-propyl, isopropyl, n-butyl, isobutyl, sec-butyl, tert-butyl, isopenyl, benzyl, and phenyl, and $R^4$ is selected from the group consisting of hydrogen and $COR^5$. In still another such embodiment, R is methyl, $R^1$ is selected from the group consisting of methyl, ethyl, n-propyl, isopropyl, n-butyl, isobutyl, sec-butyl, tert-butyl, benzyl and phenyl, $R^2$ and $R^3$ are independently selected from the group consisting of hydrogen, methyl, ethyl, n-propyl, isopropyl, n-butyl, isobutyl, sec-butyl, tert-butyl, isopenyl, benzyl, and phenyl, and $R^4$ is hydrogen. In another such embodiment, R is methyl, $R^1$ is isobutyl, $R^2$ and $R^3$ are selected from the group consisting of hydrogen or methyl, and $R^4$ is selected from the group consisting of hydrogen and $COR^5$. In another such embodiment, R is methyl, $R^1$ is isobutyl, $R^2$ and $R^3$ are hydrogen, and $R^4$ is selected from the group consisting of hydrogen and $COR^5$. In another such embodiment, R is methyl, $R^1$ is isobutyl, $R^2$ and $R^3$ are hydrogen, and $R^4$ is hydrogen.

In additional embodiments, R is lower alkyl, $R^1$ is selected from the group consisting of lower alkyl, aralkyl and optionally substituted aryl, $R^2$ and $R^3$ are independently selected from the group consisting of hydrogen, optionally substituted lower alkyl, aralkyl and optionally substituted aryl, $R^4$ is selected from the group consisting of hydrogen and $COR^5$, Z is $NR^{10}$, $R^{10}$ is selected from the group consisting of hydrogen and optionally substituted lower alkyl, and $X^-$ is a pharmaceutically acceptable cation, which in certain embodiments is selected from the group consisting of hydroxide, chloride, bromide, iodide, sulphate, nitrate, phosphate, formate, acetate, maleate, fumarate, citrate, oxalate, succinate, tartrate, malate, mandelate, lactate, gluconate, trifluoroacetate, methanesulphonate, besylate and p-toluenesulphonate. In one such embodiment, R is lower alkyl, $R^1$ is selected from the group consisting of lower alkyl, aralkyl and optionally substituted aryl, $R^2$ and $R^3$ are independently selected from the group consisting of hydrogen, optionally substituted lower alkyl, aralkyl and optionally substituted aryl, $R^4$ and $R^{10}$ are hydrogen, and $X^-$ is selected from the group consisting of hydroxide, chloride, bromide, iodide, sulphate, nitrate, phosphate, formate, acetate, maleate, fumarate, citrate, oxalate, succinate, tartrate, malate, mandelate, lactate, gluconate, trifluoroacetate, methanesulphonate, besylate, and p-toluenesulphonate. In another such embodiment, R is methyl, $R^1$ is selected from the group consisting of methyl, ethyl, n-propyl, isopropyl, n-butyl, isobutyl, sec-butyl, tert-butyl, benzyl, and phenyl, $R^2$ and $R^3$ are independently selected from the group consisting of hydrogen, methyl, ethyl, n-propyl, isopropyl, n-butyl, isobutyl, sec-butyl, tert-butyl, isopenyl, benzyl, and phenyl, $R^4$ is selected from the group consisting of hydrogen and $COR^5$, $R^{10}$ is hydrogen, and $X^-$ is selected from the group consisting of hydroxide, chloride, bromide, iodide, sulphate, nitrate, phosphate, formate, acetate, maleate, fumarate, citrate, oxalate, succinate, tartrate, malate, mandelate, lactate, gluconate, trifluoroacetate, methanesulphonate, besylate and p-toluenesulphonate. In still another such embodiment, R is methyl, $R^1$ is selected from the group consisting of methyl, ethyl, n-propyl, isopropyl, n-butyl, isobutyl, sec-butyl, tert-butyl, benzyl, and phenyl, $R^2$ and $R^3$ are independently selected from the group consisting of hydrogen, methyl, ethyl, n-propyl, isopropyl, n-butyl, isobutyl, sec-butyl, tert-butyl, isopenyl, benzyl, and phenyl, $R^4$ and $R^{10}$ are hydrogen, and $X^-$ is selected from the group consisting of hydroxide, chloride, bromide, iodide, sulphate, nitrate, phosphate, formate, acetate, maleate, fumarate, citrate, oxalate, succinate, tartrate, malate, mandelate, lactate, gluconate, trifluoroacetate, methanesulphonate, besylate and p-toluenesulphonate. In another such embodiment, R is methyl, $R^1$ isobutyl, $R^2$ and $R^3$ are independently selected from the group consisting of hydrogen and methyl, $R^4$ is selected from the group consisting of hydrogen and $COR^5$, $R^{10}$ is hydrogen, and $X^-$ is selected from the group consisting of hydroxide, chloride, bromide, iodide, sulphate, nitrate, phosphate, formate, acetate, maleate, fumarate, citrate, oxalate, succinate, tartrate, malate, mandelate, lactate, gluconate, trifluoroacetate, methanesulphonate, besylate and p-toluenesulphonate. In still another such embodiment, R is methyl, $R^1$ isobutyl, $R^2$ and $R^3$ are independently selected from the group consisting of hydrogen and methyl, $R^4$ and $R^{10}$ are hydrogen, and $X^-$ is selected from the group consisting of hydroxide, chloride, bromide, iodide, sulphate, nitrate, phosphate, formate, acetate, maleate, fumarate, citrate, oxalate, succinate, tartrate, malate, mandelate, lactate, gluconate, trifluoroacetate, methanesulphonate, besylate and p-toluenesulphonate. In another such embodiment, R is methyl, $R^1$ isobutyl, $R^2$ and $R^3$ are hydrogen, $R^4$ and $R^{10}$ are hydrogen, and $X^-$ is selected from the group consisting of hydroxide, chloride, bromide, iodide, sulphate, nitrate, phosphate, formate, acetate, maleate, fumarate, citrate, oxalate, succinate, tartrate, malate, mandelate, lactate, gluconate, trifluoroacetate, methanesulphonate, besylate and p-toluenesulphonate.

In additional embodiments, R is lower alkyl, $R^1$ is selected from the group consisting of lower alkyl, aralkyl and optionally substituted aryl, $R^2$ and $R^3$ are independently selected from the group consisting of hydrogen, optionally substituted lower alkyl, aralkyl and optionally substituted aryl, $R^4$ is selected from the group consisting of hydrogen and $COR^5$, Z is O, and $X^-$ is a pharmaceutically acceptable cation, which in certain embodiments is selected from the group consisting of hydroxide, chloride, bromide, iodide, sulphate, nitrate, phosphate, formate, acetate, maleate, fumarate, citrate, oxalate, succinate, tartrate, malate, mandelate, lactate, gluconate, trifluoroacetate, methanesulphonate, besylate and p-toluenesulphonate. In one such embodiment, R is lower alkyl, $R^1$ is selected from the group consisting of lower alkyl, aralkyl and optionally substituted aryl, $R^2$ and $R^3$ are independently selected from the group consisting of hydrogen, optionally substituted lower alkyl, aralkyl and optionally substituted aryl, $R^4$ is hydrogen, Z is O, and $X^-$ is selected from the group consisting of hydroxide, chloride, bromide, iodide, sulphate, nitrate, phosphate, formate, acetate, maleate, fumarate, citrate, oxalate, succinate, tartrate, malate, mandelate, lactate, gluconate, trifluoroacetate, methanesulphonate, besylate, and p-toluenesulphonate. In another such embodiment, R is methyl, $R^1$ is selected from the group consisting of methyl, ethyl, n-propyl, isopropyl, n-butyl, isobutyl, sec-butyl, tert-butyl, benzyl, and phenyl, $R^2$ and $R^3$ are independently selected from the group consisting of hydrogen, methyl, ethyl, n-propyl, isopropyl, n-butyl, isobutyl, sec-butyl, tert-butyl, isopenyl, benzyl, and phenyl, $R^4$ is selected from the group consisting of hydrogen and $COR^5$, Z is O, and $X^-$ is selected from the group consisting of hydroxide, chloride, bromide, iodide, sulphate, nitrate, phosphate, formate, acetate, maleate, fumarate, citrate, oxalate, succinate, tartrate, malate, mandelate, lactate, gluconate, trifluoroacetate, methanesulphonate, besylate and p-toluenesulphonate. In still another such embodiment, R is methyl, $R^1$ is selected from the group consisting of methyl, ethyl, n-propyl, isopropyl, n-butyl, isobutyl, sec-butyl, tert-butyl, benzyl, and phenyl, $R^2$ and $R^3$ are independently selected from the group consisting of hydrogen, methyl, ethyl, n-propyl, isopropyl, n-butyl, isobutyl, sec-butyl, tert-butyl, isopenyl, benzyl, and phenyl, $R^4$ is hydrogen, Z is O, and $X^-$ is selected from the group consisting of hydroxide, chloride, bromide, iodide, sulphate, nitrate, phosphate, formate, acetate, maleate, fumarate, citrate, oxalate, succinate, tartrate, malate, mandelate, lactate, gluconate, trifluoroacetate, methanesulphonate, besylate and p-toluenesulphonate. In another such embodiment, R is methyl, $R^1$ isobutyl, $R^2$ and $R^3$ are independently selected from the group consisting of hydrogen and methyl, $R^4$ is selected from the group consisting of hydrogen and $COR^5$, Z is O, and $X^-$ is selected from the group consisting of hydroxide, chloride, bromide, iodide, sulphate, nitrate, phosphate, formate, acetate, maleate, fumarate, citrate, oxalate, succinate, tartrate, malate, mandelate, lactate, gluconate, trifluoroacetate, methanesulphonate, besylate and p-toluenesulphonate. In still another such embodiment, R is methyl, $R^1$ isobutyl, $R^2$ and $R^3$ are independently selected from the group consisting of hydrogen and methyl, $R^4$ is hydrogen, Z is O, and $X^-$ is selected from the group consisting of hydroxide, chloride, bromide, iodide, sulphate, nitrate, phosphate, formate, acetate, maleate, fumarate, citrate, oxalate, succinate, tartrate, malate, mandelate, lactate, gluconate, trifluoroacetate, methanesulphonate, besylate and p-toluenesulphonate. In another such embodiment, R is methyl, $R^1$ isobutyl, $R^2$ and $R^3$ are hydrogen, $R^4$ is hydrogen, Z is O, and $X^-$ is selected from the group consisting of hydroxide, chloride, bromide, iodide, sulphate, nitrate, phosphate, formate, acetate, maleate, fumarate, citrate, oxalate, succinate, tartrate, malate, mandelate, lactate, gluconate, trifluoroacetate, methanesulphonate, besylate and p-toluenesulphonate.

In additional embodiments, β-hydroxy-γ-aminophosphonates and β-amino-γ-aminophosphonates of the present invention are zwitterionic compounds of Formula II:

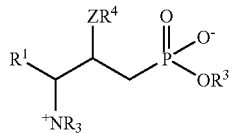
II or pharmaceutically acceptable hydrates, crystalline forms or amorphous forms thereof, particularly wherein R, $R^1$, $R^3$, $R^4$ and Z have the meanings as described above for Formula I.

In one such embodiment, a compound of Formula II is a mixture of stereoisomers, e.g., a mixture of diastereomers and/or enantiomers. Thus, in one particular such embodiment, a compound of Formula II is a mixture of diastereomers. In another particular such embodiment, a compound of Formula I is a mixture of enantiomers. In yet another embodiment, a compound of Formula II is a single enantiomer.

In additional embodiments, the β-hydroxy-γ-aminophosphonates and β-amino-γ-aminophosphonates of the present invention are zwitterionic compounds of Formulae 3S-II; 3R-II; 2R,3S-II; 2S,3S-II; 3R,3R-II; or 2S,3R-II:

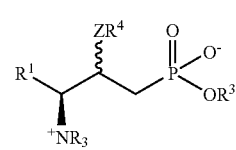
3S-II

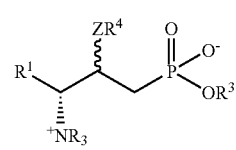
3R-II

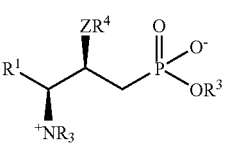
2R,3S-II

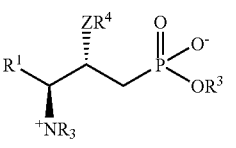
2S,3S-II

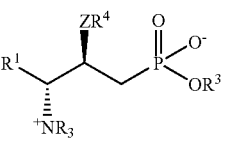
2R,3R-II

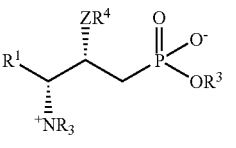
2S,3R-II or pharmaceutically acceptable hydrates, crystalline forms or amorphous forms of any one thereof, particularly wherein R, $R^1$, $R^3$, $R^4$ and Z have the meanings as described above for Formula I.

In one such embodiment, a β-hydroxy-γ-aminophosphonate or β-amino-γ-aminophosphonate analog is a zwitterionic compound of Formula 3S-II, i.e., a diastereomeric mixture having S-stereochemistry at the 3-position. In another such embodiment, a β-hydroxy-γ-aminophosphonate or β-amino-γ-aminophosphonate analog is a zwitterionic compound of Formula 3R-II, i.e., a diastereomeric mixture having R-stereochemistry at the 3-position. In another such embodiment, a β-hydroxy-γ-aminophosphonate or β-amino-γ-aminophosphonate analog is a zwitterionic compound of Formula 2R,3S-II, i.e., the 2R, 3S-isomer. In another such embodiment, a β-hydroxy-γ-aminophosphonate or β-hydroxy-γ-aminophosphonate analog is a zwitterionic compound of Formula 2S,3S-II, i.e., the 2S,3S-isomer. In another embodiment, a β-hydroxy-γ-aminophosphonate or β-amino-γ-aminophosphonate analog is a zwitterionic compound of Formula 2R,3R-II, i.e., the 2R,3R-isomer. In another embodiment, the β-hydroxy-γ-aminophosphonate or β-amino-γ-aminophosphonate analog is a zwitterionic compound of Formula 2S,3R-II, i.e., the 2S,3R-isomer.

In certain such embodiments, a compound of Formula II, or a stereoisomer or mixture of stereoisomers thereof, has a purity of about 90% or more, e.g., about 90%, about 91%, about 92%, about 93%, about 94%, about 95%, about 96%, about 97%, about 98%, about 99%, about 99.5% or more.

As it relates to a compound of Formula II, or a stereoisomer or mixture of stereoisomers thereof, e.g., a compound of Formulae 3S-II; 3R-II; 2R,3S-II; 2S,3S-II; 3R,3R-II or 2S,3R-II, in one embodiment, R is lower alkyl. In another such embodiment, R is methyl.

In additional embodiments, $R^1$ is selected from the group consisting of hydrogen, optionally substituted lower alkyl, aralkyl and optionally substituted aryl.

In additional embodiments, $R^1$ is selected from the group consisting of lower alkyl, aralkyl, and optionally substituted aryl. In one such embodiment, $R^1$ is selected from the group consisting of methyl, ethyl, n-propyl, isopropyl, n-butyl, isobutyl, sec-butyl, tert-butyl, benzyl, and phenyl, and particularly isobutyl.

In additional embodiments, $R^3$ is selected from the group consisting of hydrogen, optionally substituted lower alkyl, aralkyl, and optionally substituted aryl.

In additional embodiments, $R^3$ is selected from the group consisting of hydrogen, lower alkyl, aralkyl, and aryl. In one such embodiment, $R^3$ is selected from the group consisting of hydrogen, methyl, ethyl, n-propyl, isopropyl, n-butyl, isobutyl, sec-butyl, tert-butyl, isopenyl, benzyl, and phenyl, particularly hydrogen or methyl, and more particularly hydrogen.

In additional embodiments, $R^4$ is selected from the group consisting of hydrogen, optionally substituted lower alkyl and $COR^5$. In one such embodiment, $R^4$ is hydrogen. In another such embodiment, $R^4$ is optionally substituted lower alkyl. In one embodiment, $R^4$ is lower alkyl. In still another such embodiment, $R^4$ is $COR^5$. In one such embodiment, $R^5$ is optionally substituted lower alkyl. In another such embodiment, $R^5$ is lower alkyl, such as methyl.

In additional embodiments, Z is $NR^{10}$. In one such embodiment, $R^{10}$ is selected from the group consisting of hydrogen and optionally substituted alkyl. In another such embodiment, $R^{10}$ is hydrogen.

In additional embodiments, Z is O.

In additional embodiments, R is lower alkyl and $R^1$ is selected from the group consisting of optionally substituted lower alkyl, aralkyl, and optionally substituted aryl. In one such embodiment, R is methyl and $R^1$ is selected from the group consisting of lower alkyl, aralkyl, and optionally substituted aryl. In another such embodiment, R is methyl and $R^1$ is selected from the group consisting of methyl, ethyl, n-propyl, isopropyl, n-butyl, isobutyl, sec-butyl, tert-butyl, benzyl, and phenyl. In another such embodiment, R is methyl and $R^1$ is isobutyl.

In additional embodiments, R is lower alkyl, $R^1$ is selected from the group consisting of lower alkyl, aralkyl and optionally substituted aryl, and $R^3$ is selected from the group consisting of hydrogen, optionally substituted lower alkyl, aralkyl and optionally substituted aryl. In one such embodiment, R is methyl, $R^1$ is selected from the group consisting of methyl, ethyl, n-propyl, isopropyl, n-butyl, isobutyl, sec-butyl, tert-butyl, benzyl, and phenyl, and $R^3$ is selected from the group consisting of hydrogen, methyl, ethyl, n-propyl, isopropyl, n-butyl, isobutyl, sec-butyl, tert-butyl, isopenyl, benzyl, and phenyl. In another such embodiment, R is methyl, $R^1$ is isobutyl, and $R^3$ is selected from the group consisting of hydrogen or methyl, particularly hydrogen.

In additional embodiments, R is lower alkyl, $R^1$ is selected from the group consisting of lower alkyl, aralkyl, and optionally substituted aryl, $R^3$ is selected from the group consisting of hydrogen, optionally substituted lower alkyl, aralkyl, and optionally substituted aryl, $R^4$ is selected from the group consisting of hydrogen and $COR^5$, Z is $NR^{10}$, and $R^{10}$ is selected from the group consisting of hydrogen and optionally substituted lower alkyl. In one such embodiment, R is lower alkyl, $R^1$ is selected from the group consisting of lower alkyl, aralkyl, and optionally substituted aryl, $R^3$ is selected from the group consisting of hydrogen, optionally substituted lower alkyl, aralkyl, and optionally substituted aryl, Z in $NR^{10}$, and $R^4$ and $R^{10}$ are hydrogen. In another such embodiment, R is methyl, $R^1$ is selected from the group consisting of methyl, ethyl, n-propyl, isopropyl, n-butyl, isobutyl, sec-butyl, tert-butyl, benzyl, and phenyl, $R^3$ is selected from the group consisting of hydrogen, methyl, ethyl, n-propyl, isopropyl, n-butyl, isobutyl, sec-butyl, tert-butyl, isopenyl, benzyl, and phenyl, Z is $NR^{10}$, $R^{10}$ is hydrogen, and $R^4$ is selected from the group consisting of hydrogen and $COR^5$. In such another embodiment, R is methyl, $R^1$ is selected from the group consisting of methyl, ethyl, n-propyl, isopropyl, n-butyl, isobutyl, sec-butyl, tert-butyl, benzyl, and phenyl, $R^3$ is selected from the group consisting of hydrogen, methyl, ethyl, n-propyl, isopropyl, n-butyl, isobutyl, sec-butyl, tert-butyl, isopenyl, benzyl, and phenyl, and $R^4$ is hydrogen. In another such embodiment, R is methyl, $R^1$ is isobutyl, $R^3$ is selected from the group consisting of hydrogen or methyl, Z is $NR^{10}$, $R^{10}$ is hydrogen, and $R^4$ is selected from the group consisting of hydrogen and $COR^5$. In another such embodiment, R is methyl, $R^1$ is isobutyl, $R^3$ is hydrogen, Z is $NR^{10}$, $R^{10}$ is hydrogen, and $R^4$ is selected from the group consisting of hydrogen and $COR^5$. In one particular embodiment, R is methyl, $R^1$ is isobutyl, Z is $NR^{10}$, and $R^3$, $R^4$, and $R^{10}$ are hydrogen.

In additional embodiments, R is lower alkyl, $R^1$ is selected from the group consisting of lower alkyl, aralkyl, and optionally substituted aryl, $R^3$ is selected from the group consisting of hydrogen, optionally substituted lower alkyl, aralkyl, and optionally substituted aryl, $R^4$ is selected from the group consisting of hydrogen and $COR^5$, and Z is O. In one such embodiment, R is lower alkyl, $R^1$ is selected from the group consisting of lower alkyl, aralkyl, and optionally substituted aryl, $R^3$ is selected from the group consisting of hydrogen, optionally substituted lower alkyl, aralkyl, and optionally substituted aryl, Z is O, and $R^4$ is hydrogen. In another such embodiment, R is methyl, $R^1$ is selected from the group consisting of methyl, ethyl, n-propyl, isopropyl, n-butyl, isobutyl, sec-butyl, tert-butyl, benzyl, and phenyl, $R^3$ is selected from the group consisting of hydrogen, methyl, ethyl, n-propyl, isopropyl, n-butyl, isobutyl, sec-butyl, tert-butyl, isopenyl, benzyl, and phenyl, Z is O, and $R^4$ is selected from the group consisting of hydrogen and $COR^5$. In such another embodiment, R is methyl, $R^1$ is selected from the group consisting of methyl, ethyl, n-propyl, isopropyl, n-butyl, isobutyl, sec-butyl, tert-butyl, benzyl, and phenyl, $R^3$ is selected from the group consisting of hydrogen, methyl, ethyl, n-propyl, isobutyl, sec-butyl, tert-butyl, isopenyl, benzyl, and phenyl, Z is O, and $R^4$ is hydrogen. In another such embodiment, R is methyl, $R^1$ is isobutyl, $R^3$ is selected from the group consisting of hydrogen or methyl, Z is O, and $R^4$ is selected from the group consisting of hydrogen and $COR^5$. In another such embodiment, R is methyl, $R^1$ is isobutyl, $R^3$ is hydrogen, Z is O, and $R^4$ is selected from the group consisting of hydrogen and $COR^5$. In one particular embodiment, R is methyl, $R^1$ is isobutyl, Z is O, and $R^3$ and $R^4$ are hydrogen.

In certain embodiments of the invention the compound is selected from the group consisting of:

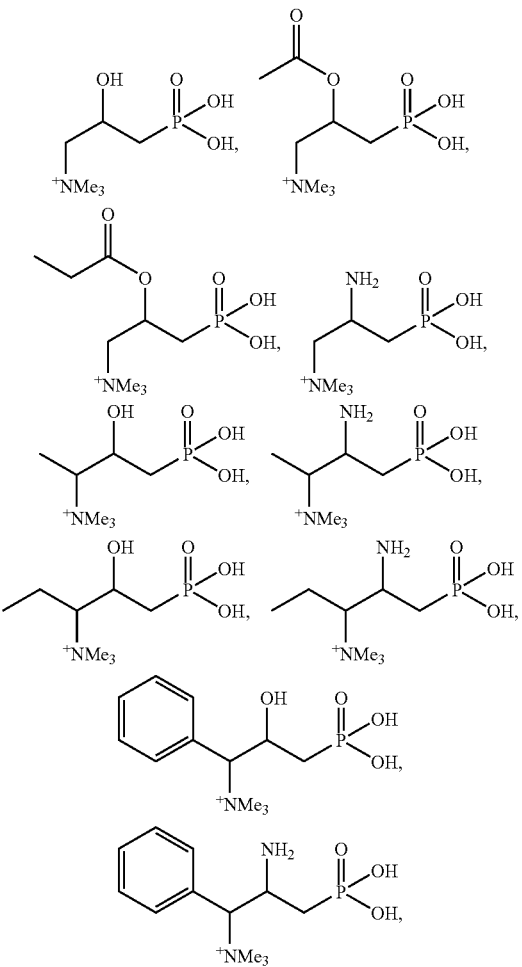

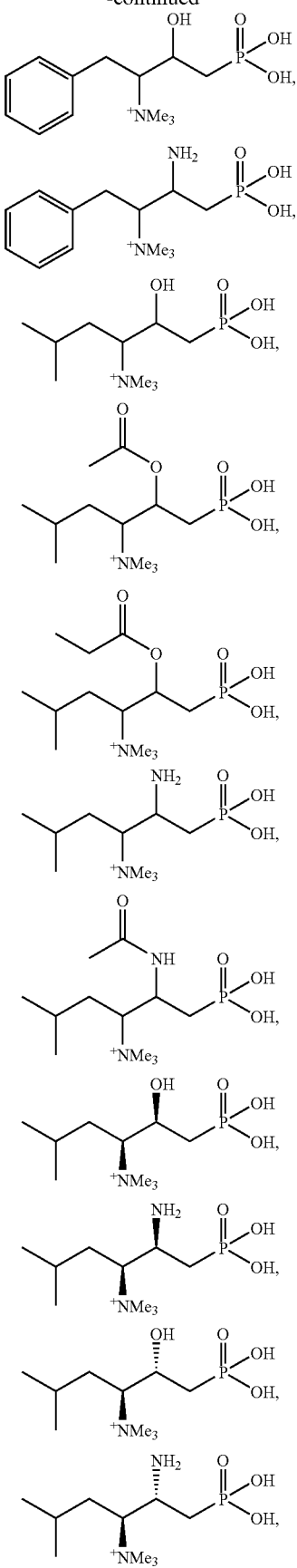

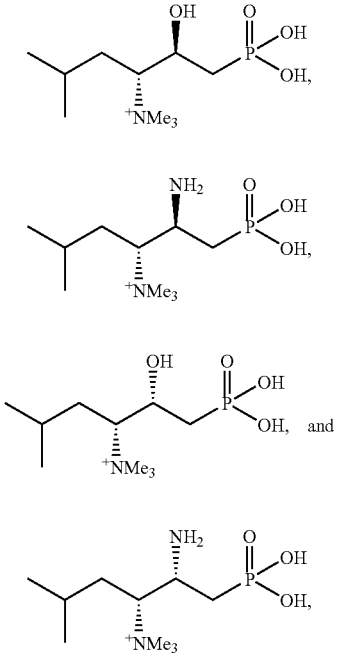

or pharmaceutically acceptable salts, esters, amides, zwitterions or other pharmaceutically acceptable derivatives, variants or forms thereof.

In another such embodiment, the compound is selected from the group consisting of:

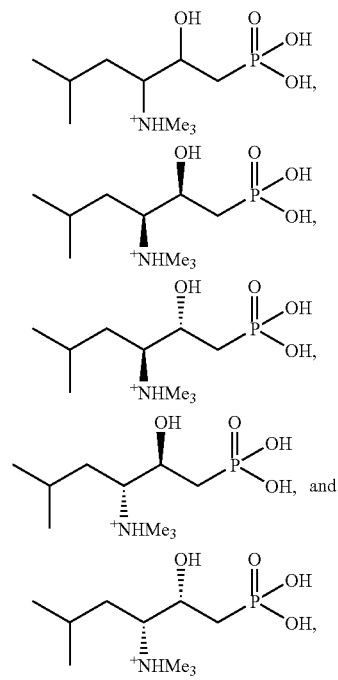

or pharmaceutically acceptable salts, esters, zwitterions or other pharmaceutically acceptable derivatives, variants or forms thereof.

In another such embodiment, the compound is:

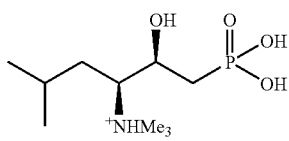

or a pharmaceutically acceptable salt, ester, zwitterion or other pharmaceutically acceptable derivative, variant or form thereof.

Methods of Synthesis

In additional embodiments, the present invention also provides methods for the preparation of a β-hydroxy-γ-aminophosphonate of Formula III:

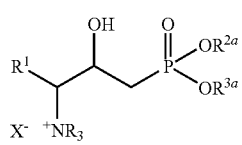

III particularly wherein:
R is selected from the group consisting of hydrogen and lower alkyl;
$R^1$ is selected from the group consisting of hydrogen, optionally substituted alkyl, aralkyl, optionally substituted cycloalkyl, optionally substituted alkenyl, optionally substituted alkynyl, optionally substituted aryl, optionally substituted heteroaryl, and optionally substituted heterocyclo;
$R^{2a}$ and $R^{3a}$ are independently selected from the group consisting of optionally substituted alkyl, aralkyl, and optionally substituted aryl; and
$X^-$ is a pharmaceutically acceptable anion, the methods comprising:
(a) reacting a compound of Formula IV

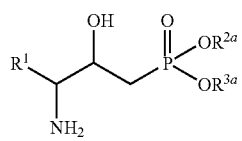

IV with RX, to give a compound of Formula III, or a stereoisomer or mixture of stereoisomers thereof; and
(b) isolating said compound of Formula III.

In one such embodiment, a compound of Formula III is a diastereomeric mixture having S-stereochemistry at the 3-position, referred to as the "3S-isomer," i.e., a compound of Formula 3S-III:

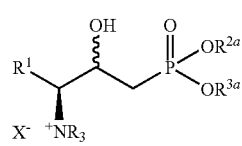

3S-III

In another such embodiment, a compound of Formula III is a diastereomeric mixture having R-stereochemistry at the 3-position, referred to as the "3R-isomer," i.e., a compound of Formula 3R-III:

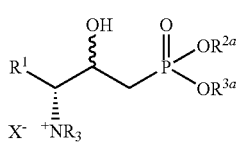

3R-III

In another such embodiment, a compound of Formula III is in the 2R, 3S-isomeric form, i.e., a compound of Formula 2R,3S-III:

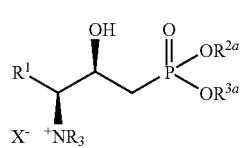

2R,3S-III

In another such embodiment, a compound of Formula III is in the 2S, 3S-isomeric form, i.e., a compound of Formula 2S,3S-III:

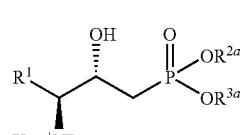

2S,3S-III

In another such embodiment, a compound of Formula III is in the 2R,3R-isomeric form, i.e., a compound of Formula 2R,3R-III:

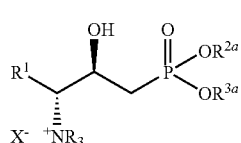

2R,3R-III

In another such embodiment, a compound of Formula III is in the 2S,3R-isomeric form, i.e., a compound of Formula 2R,3R-III.

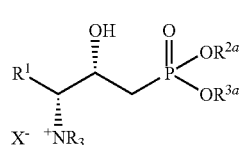

2S,3R-III

In one embodiment, particularly as it relates to a compound of Formula III, or a stereoisomer or mixture of stereoisomers thereof, RX is lower alkyl halide. In another such embodiment, RX is a lower alkyl iodide. In still another such embodiment, RX is methyl iodide. In certain embodiments, about a 3-fold excess or more of RX is used in the reaction between a compound of Formula IV and RX, e.g., about a 4-fold, about a 5-fold, about a 6-fold, about a 7-fold, about a 8-fold, about a 9-fold or about a 10-fold excess or more.

In additional embodiments, the reaction is carried out in the presence of a base, which may be, for example, potassium carbonate.

In additional embodiments, the reaction is carried out in a solvent selected from the group consisting of $C_1$-$C_4$ alcohol (e.g., methanol), tetrahydrofuran, acetonitrile and dichloromethane.

In additional embodiments, the reaction is carried out a temperature from about 20° C. to about 50° C., such as a temperature from about 37° C. to about 42° C.

In additional embodiments, the reaction mixture is filtered and the solvent is removed by evaporation to give a compound of Formula III.

In another embodiment, $R^1$ is selected from the group consisting of hydrogen, optionally substituted lower alkyl, aralkyl, and optionally substituted aryl. In another such embodiment, $R^1$ is selected from the group consisting of lower alkyl, aralkyl, and optionally substituted aryl, including but not limited to, methyl, ethyl, n-propyl, isopropyl, n-butyl, isobutyl, sec-butyl, tert-butyl, benzyl, and phenyl, and particularly isobutyl.

In additional embodiments, $R^2$ and $R^3$ are independently selected from the group consisting of lower alkyl, aralkyl, and aryl, including but not limited to, methyl, ethyl, n-propyl, isopropyl, n-butyl, isobutyl, sec-butyl, tert-butyl, isopenyl, benzyl, and phenyl, and particularly methyl.

The progress of the reaction between a compound of Formula IV, or stereoisomer or mixture of stereoisomers thereof, and RX can be monitored by analytical methods known in the art such as TLC, LC, LC/MS, HPLC, NMR, etc., according to routine protocols that will be familiar to those of ordinary skill in the art. A compound of Formula III, or a stereoisomer or mixture of stereoisomers thereof can be isolated and purified by any means known in the art such normal- and reverse-phase column chromatography (e.g., column chromatography on silica gel or reverse-phase HPLC), crystallization, extraction, etc., according to routine protocols that will be familiar to those of ordinary skill in the art. The product thus isolated can be subjected to further purification (e.g., recrystallization) until the desired level of purity is achieved. Thus, in certain embodiments, the compounds of Formula III, or the stereoisomers or mixture of stereoisomers thereof, have a purity of about 90% or more, e.g., about 91%, about 92%, about 93%, about 94%, about 95%, about 96%, about 97%, about 98%, about 99%, about 99.5% or more. In such embodiments, the level of purity can be determined by any suitable analytical technique, e.g., NMR, LC, HPLC, etc., according to protocols that will be familiar to the ordinarily skilled artisan.

In additional embodiments, the present invention also provides methods for separating the stereoisomers, e.g., diastereomers, of a compound of Formula III. Thus, in certain such embodiments, the present invention provides methods for the preparation of a compound of Formula 2S,3S-III from a compound of Formula 3S-III, for example, comprising isolating a compound of Formula 2S,3S-III, i.e., the 2S,3S-isomer, that is substantially free from a compound of Formula 2R,3S-III, i.e., the 2R,3S-isomer. In additional embodiments, the invention provides methods for the preparation of a compound of Formula 2R,3S-III from a compound of Formula 3S-III, for example, comprising isolating a compound of Formula 2R,3S-III that is substantially free from a compound of Formula 2S,3S-III. In additional embodiments, the invention provides methods for the preparation of a compound of Formula 2R,3R-III from a compound of Formula 3R-III, for example, comprising isolating a compound of Formula 2R,3R-III, i.e., the 2R,3R-isomer, that is substantially free from a compound of Formula 2S,3R-III, i.e., the 2S,3R-isomer. In additional embodiments, the invention provides methods for the preparation of a compound of Formula 2S,3R-III from a compound of Formula 3R-III, for example, comprising isolating a compound of Formula 2S,3R-III that is substantially free from a compound of Formula 2R,3R-III.

According to this aspect of the invention, the diastereomers of a compound of Formulae 3S-III or 3R-III can be isolated by any suitable separation technique known in the art of chemical synthesis, e.g., chromatography or crystallization, as described in further detail herein below. In one such embodiment, the diastereomers are isolated by chromatography, e.g., reverse phase chromatography. In another such embodiment, the diastereomers are isolated by crystallization.

In one embodiment, a compound of Formula 2R,3S-III is isolated with a diastereomeric excess of about 90% or more, e.g., about 91%, about 92%, about 93%, about 94%, about 95%, about 96%, about 97%, about 98%, about 99% or more. In another embodiment, a compound of Formula 2S,3S-III is isolated with a diastereomeric excess of about 90% or more, e.g., about 91%, about 92%, about 93%, about 94%, about 95%, about 96%, about 97%, about 98%, about 99% or more. In still another embodiment, a compound of Formula 2R,3R-III is isolated with a diastereomeric excess of about 90% or more, e.g., about 91%, about 92%, about 93%, about 94%, about 95%, about 96%, about 97%, about 98%, about 99% or more. In still another embodiment, a compound of Formula 2S,3R-III is isolated with a diastereomeric excess of about 90% or more, e.g., about 91%, about 92%, about 93%, about 94%, about 95%, about 96%, about 97%, about 98%, about 99% or more. In such embodiments, the level of diastereomeric excess can be determined by any suitable analytical technique, e.g., NMR, LC, HPLC, etc., according to protocols that will be familiar to the ordinarily skilled artisan.

In one particular embodiment according to this aspect of the invention, the diastereomers of a compound of Formulae 3S-III or 3R-III are separated by crystallization. In one such embodiment, the crystallization comprises:

(a) dissolving a compound of Formulae 3S-III or 3R-III in a solvent or solvent system, i.e., a mixture of solvents, e.g., methanol/water, ethanol/water, tetrahydrofuran/water, acetonitrile/water, etc., to give a solution;
(b) allowing precipitation to occur thereby forming a precipitate; and
(c) separating crystalline product in said precipitate from the solution.

In certain such embodiments, the solution is a homogeneous solution, i.e., the compound of Formulae 3S-III or 3R-III is completely dissolved. In certain embodiments, the solvent or solvent system is selected from the group consisting of dichloromethane, methanol, methanol/water, ethanol, ethanol/water, isopropanol, isopropanol/water, tetrahydrofuran, tetrahydrofuran/water, acetonitrile and acetonitrile/water.

In other embodiments of the invention, precipitation of the desired product, i.e., a compound of Formulae 2R,3S-III, 2S,3S-III, 3R,3R-III or 2S,3R-III, is induced by adding an anti-solvent to said solution. In certain such embodiments, the anti-solvent is selected from the group consisting of hexane, ethyl acetate, acetone, methyl ethyl ketone, and methyl t-butyl ether, and particularly ethyl acetate.

In additional embodiments, precipitation of the product during crystallization is induced by cooling the solution, for example to about 10° C., to about 5° C., or to about 0° C. In certain such embodiments, the solution is heated before, during, or after the addition of the anti-solvent.

In certain additional embodiments, the crystalline product is isolated by filtration.

The present invention also provides methods for the preparation of a compound of Formula IV, the methods comprising:
(a) removing $R^6$, or removing $R^6$ and $R^7$, from a compound of Formula V

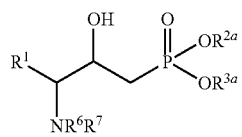

particularly wherein:
$R^6$ is an amine protecting group; and
$R^7$ is selected from the group consisting of hydrogen and an amine protecting group, or $R^6$ and $R^7$ taken together represent an amine protecting group; and $R^1$, $R^{2a}$ and $R^{3a}$ have the meanings as described above for Formula III, to give a compound of Formula IV, or stereoisomer or mixture of stereoisomers thereof; and
(b) isolating said compound of Formula IV; or
(c) using said compound of Formula IV in the next reaction without isolation.

In one such embodiment, a compound of Formula V is a diastereomeric mixture having S-stereochemistry at the 3-position, i.e. a compound of Formula 3S-V:

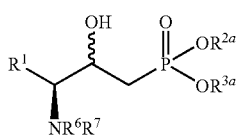

In another such embodiment, a compound of Formula V is a diastereomeric mixture having R-stereochemistry at the 3-position, i.e. a compound of Formula 3R-V:

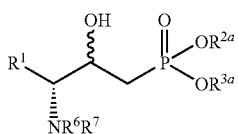

As it relates to a compound of Formula V, or a stereoisomer or mixture of stereoisomers thereof, in certain embodiments, —$NR^6R^7$ represents a mono-protected amine, i.e., $R^6$ is an amine protecting group, and $R^7$ is hydrogen. In one such embodiment, $R^6$ is selected from the group consisting of carbobenzyloxy and tert-butyloxycarbonyl, i.e., —$NR^6R^7$ is —N(H)CBz or —N(H)Boc. In another such embodiment, —$NR^6R^7$ represents a di-protected amine wherein $R^6$ and $R^7$ are each independently an amine protecting group. In still another such embodiment, $R^6$ is selected from the group consisting of carbobenzyloxy and tert-butyloxycarbonyl, and $R^7$ is benzyl, i.e., —$NR^6R^7$ is —N(Cbz)Bn or —N(Boc)Bn. In additional embodiments, —$NR^6R^7$ represents a di-protected amine wherein $R^6$ and $R^7$ taken together represent an amine protecting group such as a phthalimide group.

In one particular embodiment, $R^6$ and $R^7$ are benzyl, i.e., —$NR^6R^7$ is —$NBn_2$.

In one such embodiment, the benzyl groups are removed, i.e., the amine is deprotected to give —$NH_2$, for example, under an atmosphere of hydrogen gas using palladium on carbon as the catalyst. In such one embodiment the deprotection is carried out in a solvent selected from the group consisting of $C_1$-$C_4$ alcohol (e.g., methanol), tetrahydrofuran, acetonitrile and dichloromethane. In certain such embodiments, the deprotection is carried out a temperature from about 20° C. to about 50° C., e.g., about 37° C. to about 42° C.

In certain such embodiments, the reaction mixture is filtered through a pad of celite and the solvent(s) are removed by evaporation. In other embodiments, however, a compound of Formula IV is used in the next synthetic step without additional purification.

In certain embodiments according to this aspect of the invention, $R^1$ in a compound of Formula V, or a stereoisomer or mixture or stereoisomers thereof, is selected from the group consisting of hydrogen, optionally substituted lower alkyl, aralkyl, and optionally substituted aryl. In other embodiments, $R^1$ is selected from the group consisting of lower alkyl, aralkyl, and optionally substituted aryl. In certain such embodiments, $R^1$ is selected from the group consisting of methyl, ethyl, n-propyl, isopropyl, n-butyl, isobutyl, sec-butyl, tert-butyl, benzyl, and phenyl, and particularly isobutyl. In additional embodiments, $R^2$ and $R^3$ are independently selected from the group consisting of lower alkyl, aralkyl, and aryl, including but not limited to, methyl, ethyl, n-propyl, isopropyl, n-butyl, isobutyl, sec-butyl, tert-butyl, isopenyl, benzyl, and phenyl. In certain such embodiments, $R^2$ and $R^3$ are methyl.

The progress of the removal, i.e., deprotection, of the $R^6$ group, or $R^6$ and $R^7$ groups, from a compound of Formula V to give a compound of Formula IV can be monitored by analytical methods known in the art such as TLC, LC, LC/MS, HPLC, NMR, etc., according to routine protocols that will be familiar to those of ordinary skill in the art. A compound of Formula IV, or a stereoisomer or mixture of stereoisomers thereof, can be isolated and purified by any means known in the art such normal- and reverse-phase column chromatography (e.g., column chromatography on silica gel or reverse-phase HPLC), crystallization, extraction, etc., according to routine protocols that will be familiar to those of ordinary skill in the art. The product thus isolated can be optionally subjected to further purification (e.g., recrystallization) until the desired level of purity is achieved. Thus, in certain embodiments of the invention, a compound of Formula IV, or a stereoisomer or mixture of stereoisomers thereof, has a purity of about 90%, about 91%, about 92%, about 93%, about 94%, about 95%, about 96%, about 97%, about 98%, about 99%, about 99.5% or more. In such embodiments, the level of purity can be determined by any suitable analytical technique, e.g., NMR, LC, HPLC, etc., according to protocols that will be familiar to the ordinarily skilled artisan.

The present invention also provides methods for the preparation of β-hydroxy-γ-aminophosphonates of Formula V, the methods comprising:

(a) reducing a β-keto-γ-aminophosphonate of Formula VI:

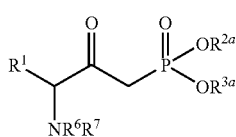

VI particularly wherein $R^1$, $R^{2a}$ and $R^{3a}$ have the meanings as described above for Formula III, and $R^6$ and $R^7$ have the meanings as described above for Formula V, to give a compound of Formula V, or a stereoisomer or mixture of stereoisomers thereof; and
(b) isolating said compound of Formula V; or
(c) using said compound of Formula V in the next reaction without isolation.

In one such embodiment, a compound of Formula VI has S-stereochemistry at the 3-position, i.e. a compound of Formula 3S-VI:

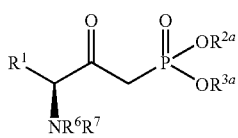

3S-VI

In another such embodiment, a compound of Formula VI has R-stereochemistry at the 3-position, i.e. a compound of Formula 3R-VI:

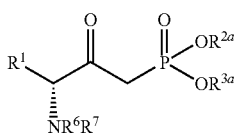

3R-VI

As it relates to a compound of Formula VI, or a stereoisomer or mixture of stereoisomers thereof, in certain embodiments, the oxo group, i.e., C=O, of a compound of Formula VI is reduced using a borohydride reducing agent. In one such embodiment, the borohydride reducing agent is sodium borohydride.

In additional embodiments, the reaction is carried out in a solvent system comprising a $C_1$-$C_4$ alcohol (e.g., methanol) and tetrahydrofuran. In one such embodiment, the solvent system comprises about 5% to about 15% tetrahydrofuran in methanol (v/v). In another such embodiment, the solvent system comprises about 10% tetrahydrofuran and about 90% methanol (v/v).

In additional embodiments, the reduction is carried out a temperature from about −30° C. to about 20° C., and particularly from about −10° C. to about 5° C.

In certain embodiments according to this aspect of the invention, the compound of Formula V is used in the next reaction without purification.

In certain embodiments according to this aspect of the invention, $R^1$ is selected from the group consisting of hydrogen, optionally substituted lower alkyl, aralkyl, and optionally substituted aryl. In one such embodiment, $R^1$ is selected from the group consisting of lower alkyl, aralkyl and optionally substituted aryl. In certain such embodiments, $R^1$ is selected from the group consisting of methyl, ethyl, n-propyl, isopropyl, n-butyl, isobutyl, sec-butyl, tert-butyl, benzyl, and phenyl, and particularly isobutyl.

In additional embodiments, $R^2$ and $R^3$ are independently selected from the group consisting of lower alkyl, aralkyl, and aryl. In one such embodiment, $R^2$ and $R^3$ are independently selected from the group consisting of methyl, ethyl, n-propyl, isopropyl, n-butyl, isobutyl, sec-butyl, tert-butyl, isopenyl, benzyl, and phenyl. In another such embodiment, $R^2$ and $R^3$ are methyl. In still another such embodiment, $R^6$ and $R^7$ are benzyl.

The progress of the reduction of a β-keto-γ-aminophosphonate of Formula VI to a β-hydroxy-γ-aminophosphonate of Formula V can be monitored by analytical methods known in the art such as TLC, LC, LC/MS, HPLC, NMR, etc., according to routine protocols that will be familiar to those of ordinary skill in the art. A compound of Formula V, or a stereoisomer or mixture of stereoisomers thereof, can be isolated and purified by any means known in the art such normal- and reverse-phase column chromatography (e.g., column chromatography on silica gel or reverse-phase HPLC), crystallization, extraction, etc., according to routine protocols that will be familiar to those of ordinary skill in the art. The product thus isolated can be optionally subjected to further purification (e.g., recrystallization) until the desired level of purity is achieved. Thus, in certain embodiments of the invention, a compound of Formula V has a purity of about 90% or more, e.g., about 91%, about 92%, about 93%, about 94%, about 95%, about 96%, about 97%, about 98%, about 99% or more. In such embodiments, the level of purity can be determined by any suitable analytical technique, e.g., NMR, LC, HPLC, etc., according to protocols that will be familiar to the ordinarily skilled artisan.

Alternatively, a compound of Formula V can be used in a subsequent chemical transformation without further purification.

The present invention also provides methods for the preparation of a compound of Formula VI, the methods comprising:
(a) condensing of a compound of Formula VII:

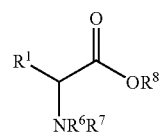

VII with a compound of Formula VIII:

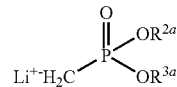

VIII particularly wherein $R^1$, $R^{2a}$ and $R^{3a}$ have the meanings as described above for Formula III, $R^6$ and $R^7$ have the meanings as described above for Formula V, and $R^8$ is selected from the group consisting of optionally substituted alkyl, aralkyl, and optionally substituted aryl, to give a compound of Formula VI, or a stereoisomer or mixture of stereoisomers thereof; and
(b) isolating said compound of Formula VI; or
(c) using said compound of Formula VI in the next reaction without isolation.

In one such embodiment, a compound of Formula VII is the S-isomer, i.e. a compound of Formula S-VII:

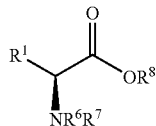

S-VII

In another such embodiment, a compound of Formula VII is the R-isomer, i.e. a compound of Formula R-VII:

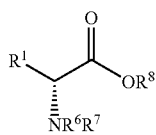

R-VII

As it relates to a compound of Formula VII, or a stereoisomer or mixture of stereoisomers thereof, in certain embodiments, the condensation with a compound of Formula VIII is carried out in an inert organic solvent. In one such embodiment, the inert organic solvent is tetrahydrofuran.

In additional embodiments, the condensation is carried out at temperature ranging from about −78° C. to about −20° C., particularly at about −50° C.

In certain embodiments according to this aspect of the invention, $R^1$ is selected from the group consisting of hydrogen, optionally substituted lower alkyl, aralkyl, and optionally substituted aryl. In another such embodiment, $R^1$ is selected from the group consisting of lower alkyl, aralkyl, and optionally substituted aryl. In still another such embodiment, $R^1$ is selected from the group consisting of methyl, ethyl, n-propyl, isopropyl, n-butyl, isobutyl, sec-butyl, tert-butyl, benzyl, and phenyl, and particularly isobutyl.

In additional embodiments, $R^2$ and $R^3$ are independently selected from the group consisting of lower alkyl, aralkyl, and aryl. In another such embodiment, $R^2$ and $R^3$ are independently selected from the group consisting of methyl, ethyl, n-propyl, isopropyl, n-butyl, isobutyl, sec-butyl, tert-butyl, isopentyl, benzyl, and phenyl. In still another such embodiment, $R^2$ and $R^3$ are methyl.

In additional embodiments, $R^6$, $R^7$ and $R^8$ are benzyl.

The progress of the condensation of a compound of Formula VII with a compound of Formula VIII can be monitored by analytical methods known in the art such as TLC, LC, LC/MS, HPLC, NMR, etc., according to routine protocols that will be familiar to those of ordinary skill in the art. A compound of Formula VI, or a stereoisomer or mixture of stereoisomers thereof, can be isolated and purified by any means known in the art such normal- and reverse-phase column chromatography (e.g., column chromatography on silica gel or reverse-phase HPLC), crystallization, extraction, etc., according to routine protocols that will be familiar to those of ordinary skill in the art. The product thus isolated can be optionally subjected to further purification (e.g., recrystallization) until the desired level of purity is achieved. Thus, in certain embodiments of the invention, a compound of Formula VI, or a stereoisomer or mixture of stereoisomers thereof, has a purity of about 90% or more, e.g., about 91%, about 92%, about 93%, about 94%, about 95%, about 96%, about 97%, about 98%, about 99 or more. In such embodiments, the level of purity can be determined by any suitable analytical technique, e.g., NMR, LC, HPLC, etc., according to protocols that will be familiar to the ordinarily skilled artisan.

Alternatively, a compound of Formula VI can be used in a subsequent chemical transformation without further purification.

The present invention also provides methods for the preparation of a compound of Formula VIII, the methods comprising:

(a) condensing a compound of Formula IX:

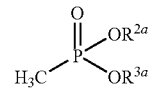

IX with $LiR^9$, particularly wherein $R^{2a}$ and $R^{3a}$ have the meanings as described above for Formula III and $R^9$ is selected from the group consisting of lower alkyl and aryl, to give a compound of Formula VIII; and (b) isolating said compound of Formula VIII; or (c) using said compound of Formula VIII without isolation.

In one such embodiment according to this aspect of the invention, $R^{2a}$ and $R^{3a}$ are independently selected from the group consisting of lower alkyl, and aralkyl. In another such embodiment, $R^{2a}$ and $R^{3a}$ are lower alkyl, particularly methyl. In one embodiment, $R^9$ is lower alkyl, particularly n-butyl (i.e., in that particular embodiment, $LiR^9$ is n-butyl lithium).

In certain embodiments, the condensation is carried out in an inert organic solvent such as tetrahydrofuran.

In certain embodiments, the condensation is carried out at temperature ranging from about −78° C. to about −20° C., more particularly at about −60° C. to about −30° C., still more particularly at about −60° C. to about −50° C., and still more particularly at about −50° C.

The progress of the condensation of a compound of Formula IX with $LiR^9$ can be monitored by analytical methods known in the art such as TLC, LC, LC/MS, HPLC, NMR, etc., according to routine protocols that will be familiar to those of ordinary skill in the art. A compound of Formula VIII is typically used in situ without isolation or purification.

The present invention also provides methods for the preparation of a compound of Formula X:

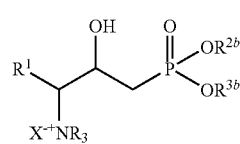

X particularly wherein R and $R^1$ have the meanings as described above for Formula III, $R^{2b}$ and $R^{3b}$ are selected from the group consisting of hydrogen and monovalent pharmaceutically acceptable cation; or taken together $R^{2b}$ and $R^{3b}$ represent a divalent pharmaceutically acceptable cation; or $X^-$ and $R^{2b}$ are absent (i.e., a compound of Formula X is a zwitterion), the method comprising:

(a) removing $R^{2a}$ and $R^{3a}$ from a compound of Formula III, to give a compound of Formula X, or a stereoisomer or mixture of stereoisomers thereof; and (b) isolating said compound of Formula X.

In one such embodiment, a compound of Formula X is a diastereomeric mixture having S-stereochemistry at the 3-position, i.e., a compound of Formula 3S-X:

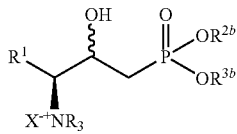

3S-X

In another such embodiment, a compound of Formula X is a diastereomeric mixture having R-stereochemistry at the 3-position, i.e., a compound of Formula 3R-X:

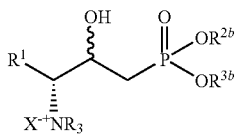

3R-X

In another such embodiment, a compound of Formula X is the 2R, 3S-isomer, i.e., a compound of Formula 2R,3S-X:

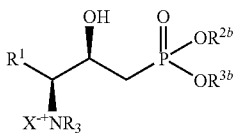

2R,3S-X

In another such embodiment, a compound of Formula X is the 2S, 3S-isomer, i.e., a compound of Formula 2S,3S-X:

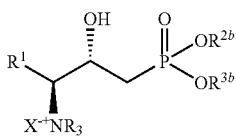

2S,3S-X

In another such embodiment, a compound of Formula X is the 2R, 3R-isomer, i.e., a compound of Formula 2R,3R-X:

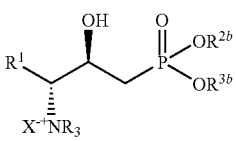

2R,3R-X

In another such embodiment, a compound of Formula X is the 2S, 3R-isomer, i.e., a compound of Formula 2S,3R-X:

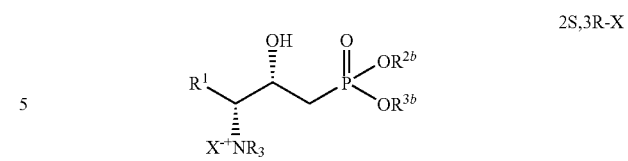

2S,3R-X

As it relates to a compound of Formula X, or a stereoisomer or mixture of stereoisomers thereof, in certain embodiments, R is lower alkyl, particularly methyl. In additional embodiments, $R^1$ is selected from the group consisting of hydrogen, optionally substituted lower alkyl, aralkyl, and optionally substituted aryl. In another such embodiment, $R^1$ is selected from the group consisting of lower alkyl, aralkyl, and optionally substituted aryl, particularly methyl, ethyl, n-propyl, iso-propyl, n-butyl, isobutyl, sec-butyl, tert-butyl, benzyl, and phenyl. In still another such embodiment, $R^1$ is isobutyl. In additional embodiments, $R^{2b}$ and $R^{3b}$ are hydrogen.

In certain embodiments according to this aspect of the invention, $R^{2b}$ and $R^{3b}$ are each a monovalent pharmaceutically acceptable cation, including but not limited to $Na^+$ and $K^+$.

In another embodiment, $R^{2b}$ and $R^{3b}$ taken together represent a divalent pharmaceutically acceptable cation, including but not limited to $Mg^{2+}$ and $Ca^{2+}$.

In another embodiment, $X^-$ and $R^{2b}$ are absent and the compound of Formula X, or stereoisomer or mixture of stereoisomers thereof, is a zwitterion.

In additional embodiments, $R^{2a}$ and $R^{3a}$ of a compound of Formula III, or a stereoisomer or mixture of stereoisomers thereof, are benzyl. In certain embodiments, the benzyl groups are removed under an atmosphere of hydrogen gas, and palladium on carbon is the catalyst. In one embodiment the benzyl groups are removed in a solvent selected from the group consisting of $C_1$-$C_4$ alcohol (e.g., methanol), tetrahydrofuran, acetonitrile and dichloromethane.

In additional embodiments, the benzyl groups are removed at temperature from about 20° C. to about 50° C., e.g., from about 37° C. to about 42° C.

In additional embodiments, the reaction mixture is filtered through a pad of celite and the solvent(s) are removed by evaporation to give a compound of Formula X, or a stereoisomer or mixture of stereoisomers thereof wherein $R^{2b}$ and $R^{3b}$ are hydrogen.

In additional embodiments, $R^{2a}$ and $R^{3a}$ of a compound of Formula III, or a stereoisomer or mixture of stereoisomers thereof, are methyl. In certain embodiments, the methyl groups are removed using bromo trimethylsilane. In one embodiment the methyl groups are removed in a solvent selected from the group consisting of tetrahydrofuran and dichloromethane.

In additional embodiments, the methyl groups are removed at temperature from about 20° C. to about 50° C., e.g., from about 37° C. to about 42° C.

In additional embodiments, the solvents are removed by evaporation. In additional embodiments, the reaction mixture is dissolved in water.

In additional embodiments, the reaction mixture is filtered and the solvent(s) are removed by evaporation to give a compound of Formula X, or a stereoisomer or mixture of stereoisomers thereof, wherein $R^{2b}$ and $R^{3b}$ are hydrogen The progress the removal of the $R^{2a}$ and $R^{3a}$ groups from a compound of Formula III to give a compound of Formula X can be monitored by analytical methods known in the art such as TLC, LC, LC/MS, HPLC, NMR, etc., according to routine protocols that will be familiar to those of ordinary skill in the art. A compound of Formula X, or a stereoisomer or mixture of stereoisomers thereof, can be isolated and purified by any means known in the art such normal- and reverse-phase column chromatography (e.g., column chromatography on silica gel or reverse-phase HPLC), crystallization, extraction, etc., according to routine protocols that will be familiar to those of ordinary skill in the art. The product thus isolated can be optionally subjected to further purification (e.g., recrystallization) until the desired level of purity is achieved. Thus, in certain embodiments of the invention, a compound of Formula X, or stereoisomer or mixture of stereoisomers thereof, has a purity of about 90%, about 91%, about 92%, about 93%, about 94%, about 95%, about 96%, about 97%, about 98%, about 99%, about 99.5% or more. In such embodiments, the level of purity can be determined by any suitable analytical technique, e.g., NMR, LC, HPLC, etc., according to protocols that will be familiar to the ordinarily skilled artisan.

In additional embodiments, the invention provides methods for the preparation of a compound of Formula VII, the method comprising:
(a) protecting the amine of an amino acid of Formula XI; and
(b) esterifying the carboxylic acid of an amino acid of Formula XI:

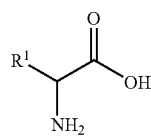

XI to give a compound of Formula VII, particularly wherein $R^1$ has the meaning as described above for Formula III; and
(c) isolating said compound of Formula VII; or
(d) using said compound of Formula VII in the next reaction without isolation.

In one such embodiment, the compound of Formula XI is the S-isomer having Formula S-XI:

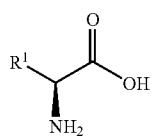

S-XI

In another such embodiment, the compound of Formula XI is the R-isomer having Formula R-XI:

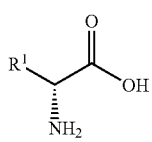

R-XI

In certain embodiments, the protection and esterification of a compound of Formula XI are accomplished simultaneously by condensation with a benzyl halide. In one such embodiment, about a 3-fold excess or more (i.e., about a 4-fold, 5-fold, 6-fold, 7-fold, 8-fold, 9-fold, 10-fold excess or more) of a benzyl halide, such as benzyl bromide, is used in the condensation. In certain embodiments, the condensation with a benzyl halide is carried out in a solvent system selected from the group consisting of a $C_1$-$C_4$-alcohol/water or acetonitrile/water. In one such embodiment, the $C_1$-$C_4$-alcohol is methanol. In a further embodiment, the solvent system comprises about 5% to about 50% solvent in water. In additional embodiments, the condensation with a benzyl halide is carried out in the presence of a base, such as potassium carbonate.

In certain aspects of the present invention, compounds of Formula I and II, or stereoisomers or mixtures of stereoisomers thereof, inhibit carnitine acyltransferases. Therefore, it is contemplated by the present invention that such compounds will be useful therapeutic agents, e.g., anticholesteremic, hypolipidemic, antidiabetic or antiobesity agents. Thus, the present invention provides compounds, compositions and methods for use in patients, particularly mammals such as humans, having diseases, conditions or disorders linked with disorders in fatty acid metabolism.

Thus, in certain embodiments of the invention, the compound of Formula I is selected from the group consisting of:

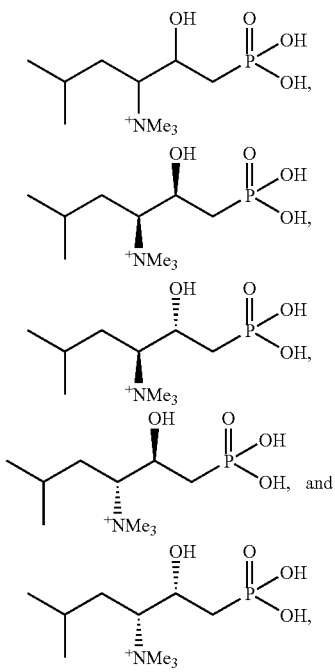

or pharmaceutically acceptable salts, esters, amides or zwitterions or other pharmaceutically acceptable derivatives, variants or forms thereof.

In additional embodiments, the compounds, compositions and methods of the present invention are used in methods provided by the invention to treat diseased cells, tissues, organs, organ systems, or pathological conditions, disorders, and/or disease states in patients (e.g., a mammalian subject including, but not limited to, humans and veterinary animals). In this regard, various pathological conditions and/or disease states are amenable to treatment, amelioration or prevention using the methods and compositions provided by the present invention.

In certain embodiments, the pathological condition and/or disease state that is amenable to treatment, amelioration or prevention using the present methods and compositions is one that is linked with disorders in fatty acid metabolism. In other embodiments, the pathological conditions and/or diseases state that are amenable to treatment, amelioration or prevention using the present methods and compositions includes, but is not limited to, hyperlipoproteinemia, hyperlipidemia, cardiac disorders, e.g., myocardial dysfunction, renal anemia, Alzheimer's disease, non-insulin dependent diabetes mellitus and obesity. Methods according to such aspects of the invention include, for example, (a) identifying a patient suffering from, afflicted with, or predisposed to a condition, disorder or disease state associated with disorders in fatty acid metabolism (including but not limited to the conditions, disorders and disease states noted above); and (b) administering to said patient one or more compounds or pharmaceutical compositions of the invention in an amount effective to treat, ameliorate and/or prevent the appearance, effects, symptoms and/or progression of the disease, condition or disorder in the patient. According to certain such aspects of the invention, the approximate dosage form(s), mode(s) of administration, dosage amounts and dosing regimen(s) for use in these methods include those described herein, although additional suitable dosage forms, modes of administration, dosage amounts and dosing regimens will be familiar to those of ordinary skill in the relevant arts and/or can be empirically determined by the clinical practitioner using routine methods known to the ordinarily skilled artisan based on the guidance provided herein and in view of the information that is readily available in the art.

Compositions within the scope of the present invention include all compositions wherein one or more of the compounds of the present invention are contained in an amount which is effective to achieve its intended purpose. While individual needs vary, determination of optimal ranges of effective amounts of each component is within the expertise of those of ordinary skill in the art. Typically, the compounds may be administered to mammals, e.g. humans, orally at a dose of about 0.0025 to about 50 mg/kg, or an equivalent amount of the pharmaceutically acceptable salt or ester thereof. For example, about 0.01 to about 25 mg/kg can be orally administered to treat, ameliorate, or prevent such disorders. For intramuscular injection, the dose is generally about one-half of the oral dose, for example, a suitable intramuscular dose would be about 0.0025 to about 25 mg/kg, e.g., from about 0.01 to about 5 mg/kg.

Compositions with the scope of the present invention also include all compositions wherein one or more of the compounds of the present invention are combined with one or more additional therapeutic agents (e.g., anticholesterolemics, anticoagulants, anti-obesity or anti-diabetic drugs) in therapeutically effective amounts. In addition to active agents (e.g., one or more compounds of the invention and one or more additional therapeutic agents), such compositions can optionally comprise one or more pharmaceutical excipients well-known in the relevant arts. Typically, such compositions are administered orally. The optimal amounts of each active agent in the composition can be determined by the clinical practioner using routine methods known to the ordinarily skilled artisan based on the guidance provided herein and in view of the information that is readily available in the art.

The unit oral dose may comprise from about 0.01 to about 1000 mg, e.g., about 0.1 to about 100 mg of the compound. The unit dose may be administered one or more times daily as one or more tablets or capsules each containing from about 0.1 to about 10, conveniently about 0.25 to 50 mg of the compound or its solvates.

In a topical formulation, the compound may be present at a concentration of about 0.01 to 100 mg per gram of carrier. In one embodiment, the compound is present at a concentration of about 0.07-1.0 mg/ml, e.g., about 0.1-0.5 mg/ml, e.g., about 0.4 mg/ml.

In addition to administering the compound as a raw chemical, the compounds of the invention may be administered as part of a pharmaceutical composition comprising one or more compounds of the invention and one or more suitable pharmaceutically acceptable carriers, such as one or more excipients or auxiliaries which facilitate processing of the compounds into preparations which can be used pharmaceutically. Preferably, such pharmaceutical compositions contain from about 0.01 to 99 percent, e.g., from about 0.25 to 75 percent of active compound(s), together with the excipient(s), particularly those compositions which can be administered orally or topically and which can be used for the preferred type of administration, such as tablets, dragees, slow release lozenges and capsules, mouth rinses and mouth washes, gels, liquid suspensions, and also preparations which can be administered rectally, such as suppositories, as well as suitable solutions for administration by parenteral administration, e.g., via intravenous infusion, intramuscular or subcutaneous injection.

The pharmaceutical compositions of the invention may be administered to any patient who may experience the beneficial effects of the compounds and/or compositions of the invention. Foremost among such patients are humans, although the invention is not intended to be so limited. Other patients include veterinary animals (cows, sheep, pigs, horses, dogs, cats and the like).

The compounds and pharmaceutical compositions of the invention may be administered by any means that achieve their intended purpose. For example, administration may be by parenteral, subcutaneous, intravenous, intramuscular, intradermal, intraperitoneal, transdermal, buccal, sublingual, intrathecal, intracranial, intranasal, ocular, pulmonary (e.g., via inhalation) or topical routes. Alternatively, or concurrently, administration may be by the oral route. The dosage administered will be dependent upon the age, health, and weight of the recipient, kind of concurrent treatment, if any, frequency of treatment, and the nature of the effect desired.

Suitable oral pharmaceutical compositions of the present invention are manufactured in a manner which is itself well-known in the art, for example, by means of conventional mixing, granulating, dragee-making, dissolving, or lyophilizing processes. Thus, solid pharmaceutical preparations for oral use can be obtained by combining one or more of the compounds of the invention and optionally one or more additional active pharmaceutical ingredients with one or more solid excipients, optionally grinding the resulting mixture and processing the mixture of granules, after adding suitable auxiliaries, if desired or necessary, to obtain tablets or dragee cores.

Suitable excipients are, in particular, fillers such as saccharides, for example lactose, sucrose, fructose and the like; sugar alcohols such as mannitol, sorbitol, or xylitol and the like; cellulose preparations and/or calcium phosphates, for example tricalcium phosphate or calcium hydrogen phosphate; as well as binders such as starch paste, using, for example, maize starch, wheat starch, rice starch, potato starch, gelatin, tragacanth, methyl cellulose, hydroxypropyl-methylcellulose, sodium carboxymethylcellulose, and/or polyvinyl pyrrolidone. If desired, disintegrating agents may be added such as the above-mentioned starches and also carboxymethyl-starch, cross-linked polyvinyl pyrrolidone, agar, or alginic acid or a salt thereof, such as sodium alginate. Auxiliaries are, above all, flow-regulating agents and lubricants, for example, silica, talc, stearic acid or salts thereof, such as magnesium stearate or calcium stearate, and/or poly(ethylene glycol). Dragee cores are provided with suitable coatings which, if desired, are resistant to gastric juices. For this purpose, concentrated saccharide solutions may be used, which may optionally contain gum arabic, talc, polyvinyl pyrrolidone, poly(ethylene glycol) and/or titanium dioxide, lacquer solutions and suitable organic solvents or solvent mixtures. In order to produce coatings resistant to gastric juices, solutions of suitable cellulose preparations such as acetylcellulose phthalate or hydroxypropylmethyl-cellulose phthalate, can be used. Dye stuffs or pigments may be added to the tablets or dragee coatings, for example, for identification or in order to characterize combinations of active ingredients or doses thereof.

Other pharmaceutical preparations which can be used orally include push-fit capsules made of gelatin, as well as soft, sealed capsules made of gelatin and a plasticizer such as glycerol or sorbitol. In certain embodiments, the push-fit capsules can comprise one or more of the compounds of the invention in the form of granules which may be mixed with fillers such as lactose, binders such as starches, and/or lubricants such as talc or magnesium stearate and, optionally, stabilizers. In soft capsules, one or more pharmaceutical ingredients (e.g., one or more compounds of the invention and optionally one or more additional active pharmaceutical ingredients) are preferably dissolved or suspended in suitable liquids, such as fatty oils, or liquid paraffin. In addition, stabilizers may be added.

Suitable pharmaceutical preparations which can be used rectally include, for example, suppositories, which comprise a combination of one or more of the compounds of the invention with a suppository base. Suitable suppository bases are, for example, natural or synthetic triglycerides, or paraffin hydrocarbons. In addition, it is also possible to use gelatin rectal capsules which consist of a combination of the active compounds with a base. Possible base materials include, for example, liquid triglycerides, poly(ethylene glycols), or paraffin hydrocarbons.

In addition to the solid dosage forms disclosed throughout, the present invention also provides chewable oral formulations. In certain such embodiments, the formulations will comprise (or consist essentially of) an effective amount of one or more compounds of the invention along with suitable excipients that allow the formulations to be chewed by the patient. In additional embodiments, the formulations can further comprise one or more taste-masking or sweetening agents, such as those described herein. In one embodiment, sucralose is used in the chewable formulations. Additional active agents, such as those described herein, can also optionally be added to the chewable formulations. The amount of one or more compounds of the invention, other optional active agents (e.g., anticholesterolemics, anticoagulants, anti-obesity or anti-diabetic drugs), and sweetening agents (e.g., sucralose) in the chewable formulations of the present invention are readily determinable by those of ordinary skill in the art, and include those amounts and combinations described herein. For example, the chewable formulations of the present invention comprise (or consist essentially of) about 0.05% to about 5% of a one or more compounds of the invention, optionally about 0.01% to about 10% other active agent(s) (or more as required), and about 0.05% to about 0.15% sucralose. Such chewable formulations are especially useful in patient populations where compliance is an issue, such as children, the elderly, and patients who may have difficulty swallowing or using spray/inhalable formulations.

The formulations may also contain colorants to improve the appearance of the chewable formulations, especially since an attractive coloration imparted by a colorant may improve patient compliance. The relative amounts of the colorants selected will vary depending upon the particular hue of the individual colorants and the resultant color desired.

Any standard pharmaceutically acceptable excipient can be used in the chewable tablet formulations which provides adequate compression such as diluents (e.g., mannitol, xylitol, maltitol, lactitol, sorbitol, lactose, sucrose, and compressible sugars such as DiPac® (dextrinized sucrose), available from Austin Products Inc. (Holmdel, N.J.), binders, disintegrants, splitting or swelling agents (e.g., polyvinyl polypyrrolidone, croscarmellose sodium (e.g., Ac-Di-Sol available from FMC BioPolymer, Philadelphia, Pa.), starches and derivatives, cellulose and derivatives, microcrystalline celluloses, such as Avicel™ PH 101 or Avicel™ CE-15 (a microcrystalline modified with guar gum), both available from FMC BioPolymer, (Philadelphia, Pa.), lubricating agents (e.g., magnesium stearate), and flow agents (e.g., colloidal silicon dioxide, such as Cab-O-Sil M5® available from Cabot Corporation, Kokomo, Ind.).

Suitable amounts of sweetener (e.g., sucralose) used in the chewable formulations, will be familiar to, and can be readily determined by, those skilled in the art. In certain embodiments, the sweetener is present in an amount from about 0.05% to about 5.0% (e.g., about 0.05%, about 0.1%, about 0.125%, about 0.15%, about 0.2%, about 0.3%, about 0.4%, about 0.5%, about 0.6%, about 0.7%, about 0.8%, about 0.9%, about 1%, about 1.25% about 1.5%, about 1.75%, about 2%, about 2.25%, about 2.5%, about 2.75%, about 3%, about 3.25%, about 3.5%, about 3.75%, about 4%, about 4.25%, about 4.5%, about 4.75% or about 5%). Those or ordinary skill in the art will appreciate that the amount of sweetener may vary depending on the strength of the particular sweetener used and the levels approved by the regulatory authorities for use in pharmaceutical products.

Suitable cyclodextrins for use in the chewable formulations of the present invention include $\alpha$, $\beta$, or $\gamma$ cyclodextrins, or an alkylated or hydroxyalkylated derivatives thereof, such as heptakis (2,6-di-o-methyl)-$\beta$-cyclodextrin (DIMEB), randomly methylated $\beta$-cyclodextrin (RAMEB), and hydroxypropyl $\beta$-cyclodextrin (HP$\beta$CD). A suitable cyclodextrin is $\beta$-cyclodextrin (available from Cerestar USA, Inc., Hammond, Ind. or from Roquette America, Inc., Keokuk. Iowa under the trade name Kleptose™). If desired, the complex of the active substance with cyclodextrin can be prepared in advance, for example, by malaxating or granulating the compounds of the invention and any additional active substance(s) and the cyclodextrin in the presence of water, or by preparing an aqueous solution containing the one or more compounds of the invention and any additional active substance(s) and the cyclodextrin in the desired molar ratio. Alternatively, the compound(s) of the invention and any additional active substance(s) and the cyclodextrin can be simply mixed with other excipients and adjuvants. The molar ratio of the compound(s) and any additional active substance(s) to cyclodextrin is suitably from about 1.0:1.0 to about 4.0:1.0.

A typical manufacturing process for making either a single layer or bi-layer chewable tablet generally involves blending of the desired ingredients to form a uniform distribution of the compound(s) of the invention (and any other active agent(s)), excipients (e.g., colorants and flavoring agents as well as others). If desired, an inclusion complex of the compound(s) of the invention and any other active agent(s) and cyclodextrin (e.g., $\beta$-cyclodextrin) may be formed prior to blending into the mixture by malaxating the compound(s) of the invention and any other active agent(s) and cyclodextrin in the presence of water in a planetary mixer for about 20 minutes.

The mixture is then dried in a drying oven. After drying, the complex is mixed with any color/flavoring blend. The blend is then compressed into a single layer or bi-layer tablet using standard methods well-known to those skilled in the art (e.g., Kilian T-100 tablet press or Courtoy 292/43 rotary bi-layer press). The colorants and flavoring agents may be added to both layers to form a uniform presentation of the tablet. Methods for preparation of chewable tablets and various components for use in the tablets can be found throughout the detailed description section and the Examples of U.S. Patent Publication No. 2003/0215503, the disclosure of which is incorporated by reference herein for all purposes. Additional chewable/orally dissolving tablets, and methods for their manufacture, are disclosed in U.S. Patent Publication No. 2004/0265372 and U.S. Pat. No. 6,270,790, the disclosures of each of which are incorporated by reference herein for all purposes.

In another embodiment, the present invention provides orally disintegrating/orodispersible tablets, such as those disclosed in U.S. Pat. No. 6,723,348, the disclosure of which is incorporated herein by reference in its entirety for all purposes. The orally disintegrating/orodispersible tablets suitably disintegrate in the buccal cavity upon contact with saliva forming an easy-to-swallow suspension. Such tablets comprise (or consist essentially of) compound(s) of the invention, and optionally, one or more additional active agents (such as those described herein), in the form of coated granules, and a mixture of excipients comprising at least one disintegrating agent, a soluble diluent agent, a lubricant and optionally a swelling agent, an antistatic (fluid flow) agent, a permeabilising agent, taste-masking agents/sweeteners, flavoring agents and colors. In certain such embodiments, the disintegrating/orodispersible tablets comprise the taste-masking agent sucralose. The amounts of compound(s) of the invention, other optional active agents (e.g., anticholesterolemics, anticoagulants, anti-obesity or anti-diabetic drugs), and sweetening agents (e.g., sucralose) in the orally disintegrating tablet formulations of the present invention are readily determinable by those of ordinary skill in the art, and include those amounts and combinations described herein. For example, the orally disintegrating tablet formulations of the present invention comprise about 0.1% to about 0.15% of compound(s) of the invention, optionally about 0.01% to about 10% other active agent(s) (or more as required), and about 0.05% to about 0.15% sucralose.

In suitable embodiments, the particles/granules of compound(s) of the invention (and any other optional active agents) have a particle size such that about 100% of the particles have an average size of less than about 50 µm. In suitable such embodiments, compound(s) of the invention (and any other optional active agents) are present as coated granules.

In one embodiment, the disintegrating tablets according to the invention comprise coated granules of compound(s) of the invention (and optionally, one or more additional active agents), a taste-masking agent such as sucralose, and a mixture of excipients, the ratio of the mixture of excipients to the coated granules suitably is about 0.4:1 to about 9:1, more suitable about 1.5:1 to about 5:1, or about 2 to 3 parts by weight, the mixture of excipients suitably comprising: at least one disintegrating agent, a soluble diluent agent, a lubricant, and optionally a permeabilising agent, a swelling agent, an antistatic agent, flavoring agents and one or more coloring agents.

In suitable embodiments, the disintegrating agent is selected from the group consisting of croscarmellose, available as e.g. Ac-di-sol™, crospovidone available as e.g. Kollidon CL™, sodium starch glycolate and mixtures thereof.

According to one embodiment of the invention, the soluble diluent is a polyol having less than 13 carbon atoms and being either in the form of a directly compressible product with an average particle size of about 100 to 500 µm, or in the form of a powder with an average particle size of less than about 100 µm, this polyol suitably being selected from the group consisting of mannitol, xylitol, sorbitol and maltitol. The proportion of disintegrating agent suitably is from about 3 to about 15% by weight, e.g., about 5 to about 15% by weight, and in the case of a mixture, each disintegrating agent being present between about 1 and about 10% by weight, e.g., about 5 to about 10% by weight, and the proportion of soluble diluent agent being about 30 to about 90% by weight, e.g., about 40 to about 60% by weight, based in each case on the weight of the tablet.

Suitable lubricants for use in the disintegrating tablets include, but are not limited to, magnesium stearate, stearic acid, sodium stearyl fumarate, micronised polyoxyethyleneglycol (micronised Macrogol 6000), leukine, sodium benzoate and mixtures thereof. The amount of lubricant generally is from about 0 to about 3%, e.g., from about 1 to about 2% by weight, based on the weight of the tablet. The lubricant can be dispersed within the mixture of excipients, or according to one embodiment, sprayed over the outer surface of the tablet. Thus, according to one embodiment of the disintegrating tablets of the invention, the lubricant is in powder form and is, at least in part, disposed on the surface of the tablets.

The permeabilising agent allows the creation of a hydrophilic network which facilitates the penetration of saliva and hence assists the disintegration of the tablet. Suitable permeabilising agent include, but are not limited to, silica with a high affinity for aqueous solvents, such as colloidal silica (Aerosil™), precipitated silica (Syloid™ FP 244), maltodextrins, β-cyclodextrins and mixtures thereof. The amount of permeabilising agent suitably is between about 0 and about 5%, e.g., from about 0.5 to about 2% by weight, based on the weight of the tablet.

A swelling agent can be incorporated in the mixture of excipients. Suitable swelling agents include, but are not limited to, starch, modified starch or microcrystalline cellulose.

An antistatic agent can also be incorporated as a flow aid. Suitable antistatic agents include, but are not limited to, micronised or non-micronised talc, fumed silica (Aerosil™ R972), colloidal silica (Aerosil™ 200), precipitated silica (Syloid™ FP 244), and mixtures thereof.

According to one such embodiment of the invention, the granules of compound(s) of the invention (and optionally, one or more additional active agents such as those described herein) are characterized in that the granules are coated and comprise microcrystals of compound(s) of the invention, sucralose, at least one binder, and optionally a diluent agent, an antistatic agent, and a coloring agent. Furthermore, the granulation excipients can also include disintegrating agents and/or surfactants.

Suitable binders include, but are not limited to, cellulosic polymers, such as ethylcellulose, hydroxypropylcellulose and hydroxypropylmethyl cellulose, acrylic polymers, such as insoluble acrylate ammoniomethacrylate copolymer, polyacrylate or polymethacrylic copolymer, povidones, copovidones, polyvinylalcohols, alginic acid, sodium alginate, starch, pregelatinized starch, sucrose and its derivatives, guar gum, poly(ethylene glycol), for example an acrylic polymer, such as Eudragit™ E100, and mixtures thereof.

Optionally, in order to enhance the granulation of the compound(s) of the invention (and one or more additional active agents) or one of its pharmaceutically acceptable salts, a diluent agent can be used. Suitable diluent agents include, but are not limited to, microcrystalline cellulose, sucrose, dicalcium phosphate, starches, lactose and polyols of less than 13 carbon atoms, such as mannitol, xylitol, sorbitol, maltitol, pharmaceutically acceptable amino acids, such as glycin, and their mixtures.

In one embodiment, a granule of compound(s) of the invention (as well as any additional active agents, such as those described herein), can be in the form of a core of granulated microcrystals of compound(s) of the invention, coated with at least one layer comprising compound(s) of the invention. Such a coated core is characterized in that the core and the layer comprise each from 70% to 95%, preferably 80% to 95% by weight of compound(s) of the invention, the balance to 100% being formed with at least one binder and optionally sucralose, and that the coated core is suitably a sphere. See e.g., French patent application FR 00 14803, the disclosure of which is incorporated by reference herein.

In one embodiment of the invention, the granules can comprise (or consist essentially of): from about 10% to about 95%, e.g., from about 50% to about 70% of one or more compounds of the invention and optionally one or more additional active agents, such as those described herein, at most about 20% by weight of the binder, relative to the weight of the one or more compounds of the invention, at most about 5%, suitably about 2% by weight of the antistatic agent, relative to the weight of said granules, suitably about 0.05% to about 5% sucralose and optionally a diluent agent for the balance to 100%.

The granules can also be coated with a coating composition comprising at least one coating polymer selected from the group consisting of cellulosic polymers, acrylic polymers and their mixtures. Among the cellulosic polymers, ethylcellulose, hydroxypropylcellulose (HPC) and hydroxypropylmethylcellulose (HPMC), can be used. Among the acrylic polymers, insoluble acrylate ammonio-methacrylate copolymer (Eudragit™ RL100 or RS100 or Eudragit™ RL30D or RS30D), polyacrylate (Eudragit™ NE30D), or methacrylic copolymers (e.g., Eudragit™ L100-55 Eudragit™ L30D, Eudragit™ E100 and Eudragit™ EPO) can be used, alone, in combination, or in admixture with pH-dependent polymers. Eudragit™ E100 or a mixture of Eudragit™ EPO and Eudragit™ NE30D are suitably used. In one embodiment, the binder and the coating polymer are the same polymer.

Optionally, permeabilising agents, plasticizers, soluble agents, disintegrating agents and surfactants, can be added as coating additives. Suitable plasticizers include, but are not limited to, triacetine, triethylacetate, triethylcitrate (Eudraflex™), ethylphthalate, or mixtures thereof. The plasticizer is used in proportions of at most about 30%, preferably 10% by weight of the coating polymers. Suitable soluble agents include polyols having less than 13 carbon atoms. Surfactants may be an anionic, nonionic, cationic, zwitterionic or amphoteric surfactant. Suitable disintegrating agents include, but are not limited to, croscarmellose, available as e.g. Ac-di-sol™, crospovidone available as e.g. Kollidon CL™, and mixtures thereof.

Suitably, the coated granules according to the present invention have a particle size distribution between about 150 μm and about 500 μm, more suitably between about 150 μm and about 425 μm, such that at least 50%, more suitably at least 70% of the granules have a particle size ranging between about 150 and about 425 μm, and less than 15% of the granules have a particle size less than about 150 μm.

In one embodiment, the coated granules according to the invention comprise: from about 10% to about 95%, preferably about 40 to about 75% of granules of a compound(s) of the invention and optionally one or more optional additional active agents, such as those disclosed herein, sucralose from about 0.05% to about 5%, from about 5 to about 90%, suitably about 10 to about 70% and even more suitably from about 25 to about 55% of a coating polymer, such as Eudragit™ E100, the percentages being expressed by weight relative to the weight of the granules of a compound(s) of the invention, from about 0 to about 10% of a permeabilising agent, such as colloidal silica, the percentages being expressed by weight relative to the weight of the coating polymer.

In another embodiment, the present invention provides a solid, effervescent, rapidly dissolving dosage form of one or more compounds of the invention for oral administration, such as disclosed in U.S. Pat. No. 6,245,353, the disclosure of which is incorporated by reference herein in its entirety. In such an embodiment, the effervescent formulation comprise (or consist essentially of) (a) one or more compounds of the invention, and optionally one or more additional active agents such as those disclosed herein, (b) an effervescent base comprising at least one of (i) at least one of (1) an organic edible acid and (2) a salt thereof, (ii) at least one of an alkali metal and an alkaline earth metal carbonate and bicarbonate, and (c) optionally a pharmaceutically acceptable auxiliary ingredient. In certain suitable embodiments, the effervescent formulations further comprise one or more taste-masking agents, such as sucralose, and/or other taste-masking agents described herein. The amounts of one or more compounds of the invention, other optional active agents (e.g., anticholesterolemics, anticoagulants, anti-obesity or anti-diabetic drugs, and combinations thereof), and sweetening agents (e.g., sucralose) in the effervescent formulations of the present invention are readily determinable by those of ordinary skill in the art, and include those amounts and combinations described herein. For example, the effervescent formulations of the present invention comprise about 0.1% to about 0.15% of one or more compounds of the invention, optionally about 0.01% to about 10% other active agent(s) (or more if required), and about 0.05% to about 0.15% sucralose.

A solution or suspension of one or more compounds of the invention is formed by adding water to the soluble or dispersible effervescent tablets or soluble granules, with evolution of $CO_2$ gas. The resulting effervescent solution or suspension can be ingested very easily, even by patients who have difficulties swallowing. The rapidly disintegrating tablet can also be administered so that it directly disintegrates in the mouth. A rapid release of the active ingredient is of particular importance here, to ensure a rapid onset of action.

Effervescent agents capable of releasing $CO_2$, which can be used in the present invention, include alkali metal carbonates or alkali metal bicarbonates, such as sodium carbonate or sodium bicarbonate. Agents for inducing $CO_2$ release which are suitably employed are edible organic acids, or their acidic salts, which are present in solid form and which can be formulated with the one or more compounds of the invention active ingredient(s) and the other auxiliary ingredients (as well as any other active agents) to provide granules or tablets, without premature evolution of $CO_2$. Edible organic acids which can be so used include for example, tartaric acid, malic acid, fumaric acid, adipic acid, succinic acid, ascorbic acid, maleic acid or citric acid. Pharmaceutically acceptable acidic salts include, for example, salts of polybasic acids which are present in solid form and in which at least one acid function is still present, such as sodium dihydrogen or disodium hydrogen phosphate or monosodium or disodium citrate.

In one embodiment, the present invention provides effervescent formulations of one or more compounds of the invention including the formulations and compositions described herein, having an effervescent base comprising (a) a mixture of calcium carbonate with an organic edible acid; (b) a mixture of calcium carbonate, sodium carbonate, sodium bicarbonate and an organic edible acid; or (c) a mixture of sodium bicarbonates, sodium carbonate and an organic edible acid.

The soluble or dispersible effervescent tablets of one or more compounds of the invention or the soluble granules suitably comprise (or consisting essentially of) from about 0.5 mg to about 50 mg of one or more compounds of the invention and from about 50 mg to about 5000 mg, suitably from about 500 mg to about 3000 mg of an effervescent base, optionally, along with other active agents (such as those described herein) and excipients, including taste-masking agents such as sucralose, suitably at about 0.05% to about 5%.

The effervescent base suitably comprises from about 100 mg to about 500 mg calcium ions as, for example, calcium carbonate, and from about 20 mg to about 1500 mg citric acid and/or its salts. In another embodiment, the effervescent base comprises from about 50 mg to about 2000 mg sodium bicarbonate, from about 20 mg to about 200 mg of sodium carbonate and from about 20 mg to about 1500 mg citric acid and/or from about 20 mg to about 500 mg tartaric acid.

An additional suitable composition of the effervescent base comprises from about 50 mg to about 500 mg sodium bicarbonate, from about 20 mg to about 100 mg sodium carbonate, and from about 50 mg to about 750 mg calcium carbonate and from about 100 mg to about 1500 mg of citric acid.

The soluble/dispersible tablets can be prepared by known processes for preparing effervescent bases, such as those disclosed in U.S. Pat. No. 6,245,353, the disclosure of which is incorporated herein by reference in its entirety.

Another embodiment of the present invention is directed to a physiologically acceptable film that is particularly well-adapted to dissolve in the oral cavity of a warm-blooded animal including humans, and adhere to the mucosa of the oral cavity, to allow delivery of one or more compounds of the invention, and optionally one or more additional active agents such as those described herein. Such physiologically acceptable films suitable for use in accordance with this aspect of the present invention are disclosed in U.S. Patent Application No. 2004/0247648, the disclosure of which is incorporated herein by reference in its entirety.

In one such embodiment of the present invention, an orally dissolving/consumable film comprises a modified starch, one or more compounds of the invention, and optionally, one or more additional active agents such as those described herein, suitably, one or more taste-masking agents, such as sucralose, and optionally, at least one water soluble polymer. The amounts of one or more compounds of the invention, other optional active agents (e.g., steroids, decongestants, leukotriene antagonists, and combinations thereof), and sweetening agents (e.g., sucralose) in the orally dissolving/consumable film formulations of the present invention are readily determinable by those of ordinary skill in the art, and include those amounts and combinations described herein. For example, the orally dissolving/consumable film formulations of the present invention comprise about 0.5 mg to about 10 mg of one or more compounds of the invention, optionally about 0.50 mg to about 50 mg other active agent(s), and about 0.05% to about 0.15% sucralose.

The consumable films of the present invention may comprise one or more of the following ingredients: water, antimicrobial agents, additional film forming agents or water soluble polymers, plasticizing agents, flavorings, sulfur precipitating agents, saliva stimulating agents, cooling agents, surfactants, stabilizing agents, emulsifying agents, thickening agents, binding agents, coloring agents, triglycerides, poly(ethylene) oxides, propylene glycols, additional taste-masking agents or sweeteners, fragrances, preservatives and the like, as described in U.S. Pat. No. 6,596,298, the disclosure of which is incorporated by reference herein in its entirety.

In one such embodiment, the consumable films of the present invention include a modified starch. The modified starches used in accordance with the present invention can be prepared by mechanically, chemically or thermally modifying unmodified starches. For example, modified starches may be prepared by chemically treating starches to produce, for example, acid treatment starches, enzyme treatment starches, oxidized starches, cross-bonding starches, and other starch derivatives. Starches suitable for modification to produce modified starches may be obtained from natural products such as corn, potatoes, tapioca as well as genetically modified forms of the same such as high amylose and waxy corn as well as sorghum varieties.

Examples of modified starches for use in the practice of the present invention include, but are not limited to, modified corn starches, modified tapioca starches, acid and enzyme hydrolyzed corn and/or potato starches, hypochlorite-oxidized starches, acid-thinned starches, ethylated starches, cross-bonded starches, hydroxypropylated tapioca starches, hydroxypropylated corn starches, pregelatinized modified starches, and the like. Preferred modified starches are selected from pregelatinized modified corn starches and pregelatinized modified tapioca starches.

Representative examples of commercially available modified starches useful in the present invention include PURE-COTE™ modified starches such as PURE-COTE™ B793 (a pregelatinized modified corn starch) and PURE-COTE™ B795 (a pregelatinized modified corn starch), for example, available from Grain Processing Corporation, 1600 Oregon Street, Muscatine, Iowa 52761-1494 USA.

In one such embodiment of the present invention, the modified starch is present in amounts ranging from about 1% to about 90% by weight, in another embodiment about 10% to about 90% by weight, and in yet another embodiment from about 35% to about 80% by weight of the film.

Modified starch may be included in the film alone or optionally in combination with an additional water soluble film forming polymers such as those selected from, for example, pullulan, hydroxypropylmethyl cellulose, hydroxyethyl cellulose, hydroxypropyl cellulose, polyvinyl pyrrolidone, carboxymethyl cellulose, polyvinyl alcohol, sodium alginate, poly(ethylene glycol), tragacanth gum, guar gum, acacia gum, arabic gum, polyacrylic acid, methylmethacrylate copolymers, carboxyvinyl polymers, amylose, high amylose starch, hydroxypropylated high amylose starch, pectin, dextrin, chitin, chitosan, levan, elsinan, collagen, gelatin, zein, gluten, soy protein isolate, whey protein isolate, casein and combinations thereof. A preferred water soluble polymer is pullulan. The amount of the water soluble polymer typically is up to about 99% by weight, suitably up to about 80% by weight, more suitably up to about 50% by weight, and most suitably up to about 40% by weight of the film.

Suitable formulations for oral and/or parenteral administration include aqueous solutions of one or more of the compounds of the invention, and optionally one or more additional active pharmaceutical ingredients, in water-soluble form, for example, water-soluble salts and alkaline solutions. In addition, suspensions of the active ingredient(s) as appropriate oily injection suspensions may be administered. Suitable lipophilic solvents or vehicles include fatty oils, for example, sesame oil, or synthetic fatty acid esters, for example, ethyl oleate or triglycerides or poly(ethylene glycol)-400. Aqueous injection suspensions may optionally also comprise substances which increase the viscosity of the suspension including, for example, sodium carboxymethyl cellulose, sorbitol, and/or dextran. Optionally, the suspension may also contain one or more stabilizers, one or more preservatives (e.g., sodium edetate, benzalkonium chloride, and the like), and/or other components commonly used in formulating pharmaceutical compositions.

Suitable topical pharmaceutical compositions of the invention are formulated preferably as oils, creams, lotions, ointments and the like by choice of appropriate carriers. Such compositions of the invention therefore comprise one or more compounds of the invention, optionally one or more additional active pharmaceutical ingredients, and one or more carriers suitable for use in preparing such pharmaceutical compositions for topical administration. Suitable such carriers include vegetable or mineral oils, white petrolatum (white soft paraffin), branched chain fats or oils, animal fats and high molecular weight alcohol (greater than C12). The preferred carriers are those in which the active pharmaceutical ingredient(s) are soluble. Emulsifiers, stabilizers, humectants and antioxidants may also be included, as well as agents imparting color or fragrance, if desired. Additionally, one or more transdermal penetration enhancers can be employed in these topical formulations. Non-limiting examples of suitable such enhancers can be found in U.S. Pat. Nos. 3,989,816 and 4,444,762, which are incorporated be reference herein in their relevant parts.

Creams are preferably formulated from a mixture of mineral oil, self-emulsifying beeswax and water in which mixture the active ingredient, dissolved in a small amount of an oil such as almond oil, is admixed. A typical example of such a cream is one which includes about 40 parts water, about 20 parts beeswax, about 40 parts mineral oil and about 1 part almond oil.

Ointments may be formulated by mixing a solution of the active ingredient in a vegetable oil such as almond oil with warm soft paraffin and allowing the mixture to cool. A typical example of such an ointment is one which includes about 30% almond oil and about 70% white soft paraffin by weight.

Lotions may be conveniently prepared by dissolving the active ingredient, in a suitable high molecular weight alcohol such as propylene glycol or poly(ethylene glycol).

Suitable liquid pharmaceutical compositions for ocular administration comprise (or consisting essentially of) a therapeutically effective dose of one or more compounds of the invention, and one or more pharmaceutically acceptable carriers or excipients, wherein at least one of the pharmaceutically acceptable carriers or excipients is sucralose, wherein the composition is free, or substantially free of preservatives, and wherein the composition is provided in a single unit-dose container. Suitably, the amount of one or more compounds of the invention in such liquid, unit-dose pharmaceutical compositions is about 0.05% to about 0.15% by weight and the amount of sucralose in such liquid, unit-dose pharmaceutical compositions is about 0.05% to about 0.15% by weight. Suitable unit-dose containers include, but are not limited to, high density polyethylene containers, for example, high density polyethylene containers produced using a blow-fill-seal manufacturing technique with a volume capacity of about 1 mL.

Suitable liquid pharmaceutical compositions for nasal administration in unit-dose or multi-dose configurations, comprising (or consisting essentially of) a therapeutically effective dose of one or more compounds of the invention, and one or more pharmaceutically acceptable carriers or excipients, wherein at least one of the pharmaceutically acceptable carriers or excipients is sucralose, wherein the composition is free, or substantially free of preservatives, and wherein the composition is provided in either a unit-dose or multi-dose container. Suitably, the amount of one or more compounds of the invention in such liquid, unit-dose or multi-dose pharmaceutical compositions is about 0.05% to about 0.15% by weight and the amount of sucralose in such liquid, unit-dose or multi-dose pharmaceutical compositions is about 0.05% to about 0.15% by weight. Suitable unit-dose or multi-dose containers include, but are not limited to, high density polyethylene bottles with a volume capacity of about 1 ml to 10 mL fitted with a spray pump specifically designed for use with preservative free formulations.

The present invention also provides inhalable powder pharmaceutical compositions comprising (or consisting essentially of), a therapeutically effective dose of one or more compounds of the invention, and one or more pharmaceutically acceptable carriers or excipients, wherein the compound(s) of the invention are in the form of micronized particles and wherein at least one of the pharmaceutically acceptable carriers or excipients is sucralose, for example, micronized particles of sucralose. Suitable such inhalable powder pharmaceutical compositions comprise micronized particles of one or more compounds of the invention with an average particle size of about 1 µm to about 5 µm, and micronized particles of sucralose with an average particle size of about 1 µm to about 20 µm. Such inhalable powder pharmaceutical compositions of the present invention can be formulated for pulmonary delivery using, for example, a dry powder inhaler. Suitably, the amount of one or more compounds of the invention in such inhalable powder pharmaceutical compositions is about 0.1% to about 20.0% by weight and the amount of sucralose in such inhalable powder pharmaceutical compositions is about 0.05% to about 20.0% by weight.

The present invention also provides inhalable spray pharmaceutical compositions comprising (or consisting essentially of), a suitable concentration to provide a therapeutically effective dose of one or more compounds of the invention, and one or more pharmaceutically acceptable carrier, stabilizer or excipient, wherein the compound(s) of the invention is(are) in a solution form and wherein at least one of the pharmaceutically acceptable carriers or excipients is sucralose dissolved in the solution. Such inhalable spray pharmaceutical compositions when used with a suitable device provide a fine spray of the components (including active and non-active components) having an average particle size of about 1 µm to about 5 µm. Such inhalable spray pharmaceutical compositions of the present invention can be formulated for pulmonary delivery using, for example, a suitable device or inhaler. Suitably the amount of one or more compounds of the invention in such inhalable spray pharmaceutical compositions is about 0.1% to about 10% by weight and the amount of sucralose in such inhalable spray pharmaceutical compositions is about 0.05% to about 0.15% by weight.

Liquid dosage forms for nasal, ocular or oral administration include pharmaceutically acceptable emulsions, solutions, suspensions, syrups and elixirs. In addition to the active one or more compounds of the invention, the liquid dosage forms may contain inert diluents and/or solvents commonly used in the art. Water is the solvent of choice for the formulations of the invention; however, combinations of water with other physiologically acceptable solvents as required are also satisfactory for use. Other solvents, solubilizing agents and emulsifiers suitable for use in place of, or in addition to, water include but are not limited to saturated aliphatic mono- and polyvalent alcohols which contain 2-6 carbon atoms (including, but not limited to, ethanol, 1,2-propylene glycol, sorbitol, and glycerine), polyglycols such as poly(ethylene glycols), and surfactants/emulsifiers like the fatty acid esters of sorbitan, and mixtures thereof. Oils, in particular, cottonseed, peanut, or corn oils, may also be added to the compositions. The combination of the additional solvents in the aqueous solution should preferably not exceed about 15% (w/v) of the total composition. Besides inert diluents, the oral compositions can also include adjuvants such as wetting agents, emulsifying and suspending agents (e.g., microcrystalline cellulose, sodium carboxymethyl cellulose, hypromellose, carbopol and the like), surfactants, sweetening, flavoring, and perfuming agents, including those described in further detail herein below. Liquid dosage forms that provide the active ingredient in suspension may comprise, in addition to the active one or more compounds of the invention, one or more suspending agents such as microcrystalline cellulose, magnesium aluminum silicate, bentonite, agar-agar, hypromellose, sodium carboxymethyl cellulose, carbopol/carbomer, pectin, acacia, tragacanth or their mixtures.

Certain liquid compositions of the invention may further comprise one or more preservatives and/or one or more stabilizers. Preservatives that are suitable for use in the compositions of the invention include, but are not limited to, edetic acid and their alkali salts such as disodium EDTA (also referred to as "disodium edetate" or "the disodium salt of edetic acid") and calcium EDTA (also referred to as "calcium edetate"), benzyl alcohol, methylparaben, propylparaben, butylparaben, chlorobutanol, phenylethyl alcohol, benzalkonium chloride, thimerosal, propylene glycol, sorbic acid, and benzoic acid derivatives. The preservatives should be used at a concentration of from about 0.001% to about 0.5% (w/v) in the final composition. The combination of benzalkonium chloride, used at a concentration of from about 0.001% to about 0.5% or preferably from about 0.005% to about 0.1% (w/v), and edetic acid (as a disodium salt), used at a concentration of from about 0.005% to about 0.1% (w/v), are suitable preservative/stabilizer combination used in the compositions of the present invention.

Certain compositions of the invention may further comprise one or more solubility-enhancing agents that are used to improve the solubility of the one or more compounds of the invention used as an active ingredient. Solubility-enhancing agents that are suitable for use in the compositions of the invention include, but are not limited to, polyvinylpyrrolidone (preferably grades 25, 30, 60, or 90), poloxamer, polysorbate 80, sorbitan monooleate 80, and poly(ethylene glycols) (molecular weights of 200 to 600).

Certain compositions of the invention may further comprise one or more agents that are used to render the composition isotonic, particularly in those compositions in which water is used as a solvent. Such agents are particularly useful in compositions formulated for nasal or ocular application, since they adjust the osmotic pressure of the formulations to the same osmotic pressure as nasal or ocular secretions. Agents that are suitable for such a use in the compositions of the invention include, but are not limited to, sodium chloride, sorbitol, propylene glycol, dextrose, sucrose, and glycerine, and other isotonicity agents that are known in the art (see, e.g., Reich et al., "Chapter 18: Tonicity, Osmoticity, Osmolality and Osmolarity," in: *Remington: The Science and Practice of Pharmacy*, 20$^{th}$ Edition, Lippincott Williams and Wilkins, Philadelphia, Pa. (2000)).

It is desirable that the compositions of the present invention that are to be administered in liquid form (including intranasally, orally or ocularly applied formulations) have a pH of about 4.5 to about 7.4, and preferably have a pH of about 5.5 to 7.1, for physiological reasons. Accordingly, in additional embodiments, the compositions of the invention may further comprise one or more buffering agents or combinations thereof, that are used to adjust and/or maintain the compositions into the desired pH range. Adjustment of pH or buffering agents that are suitable for use in the compositions of the invention include, but are not limited to, citric acid, sodium citrate, sodium phosphate (dibasic, heptahydrate form), and boric acid or equivalent conventional buffers, or combinations thereof. The appropriate amounts of buffers and buffering agents, or combinations thereof, that are to be used in the compositions of the invention are readily determined by those of ordinary skill without undue experimentation, particularly in view of the guidance contained herein and in standard formularies such as the United States Pharmacopoeia, *Remington: The Science and Practice of Pharmacy*, and the like, the disclosures of which are incorporated herein by reference in their entireties.

In certain embodiments, the liquid formulations of the invention, particularly those that are to be administered intranasally, ocularly, or orally, further comprise one or more taste-masking agents, one or more flavoring agents, and/or one or more sweetening agents, or a combination of such agents. Non-limiting examples of such substances include sucralose (about 0.001 to about 1%), sucrose (about 0.5 to about 10%), saccharin (including the salt forms: sodium, calcium, etc.) (about 0.01 to about 2%), fructose (about 0.5 to about 10%), dextrose (about 0.5 to about 10%), corn syrup (about 0.5 to about 10%), aspartame (about 0.01 to about 2%), acesulfame-K (about 0.01 to about 2%), xylitol (about 0.1 to about 10%), sorbitol (about 0.1 to about 10%), erythritol (about 0.1 to about 10%), ammonium glycyrrhizinate (about 0.01 to about 4%), thaumatin (Talin™) (about 0.01 to about 2%), neotame (about 0.01 to about 2%) mannitol (about 0.5 to about 5%), menthol (about 0.01 to about 0.5%), eucalyptus oil (about 0.01 to about 0.5%), camphor (about 0.01 to about 0.5%), natural and/or artificial flavors such as Artificial Custard Cream Flavor #36184 from International Flavors and Fragrances, Inc. (New York, N.Y.) (about 0.01 to about 1.0%), and the like. Sucralose, an intense sweetener marketed for food and beverage use as SPLENDA® by McNeil Nutritionals LLP (Fort Washington, Pa.), is especially effective as a sweetening and taste-masking agent in the compositions of the present invention, particularly when used at concentrations of from about 0.001% to about 1%, preferably at concentrations of from about 0.01% to about 0.5%, and more preferably at concentrations of from about 0.02% to about 0.2%, and most preferably from about 0.05% to about 0.15% (e.g., about 0.05%, about 0.06%, about 0.07%, about 0.08%, about 0.09%, about 0.10%, about 0.11%, about 0.12%, about 0.13%, about 0.14%, or about 0.15%), of the total composition. Sucralose has been shown to be useful as a taste modifying agent in oral delivery of certain pharmaceutical compositions, for example in sore throat spray products (see U.S. Pat. No. 6,319,513), oral suspensions (see U.S. Pat. Nos. 5,658,919 and 5,621,005), solid dosage forms (see U.S. Pat. No. 6,149,941), quick melt dosage forms (see U.S. Pat. No. 6,165,512) and mucosal delivery (see U.S. Pat. No. 6,552,024), but has not heretofore been shown to be useful in intranasally or ocularly applied compositions such as those of the present invention. Additional such compositions of the invention may comprise one or more additional taste-masking or flavoring agents such as those described herein, for example menthol at a concentration of from about 0.01% to about 1%, preferably at a concentration of from about 0.05% to about 0.1%. Suitable compositions of the invention include, for example, about 0.1%-0.15% of one or more compounds of the invention and about 0.05%-0.15% sucralose, for example, about 0.1% one or more compounds of the invention and about 0.05%-0.15% sucralose, or about 0.125%-0.15% one or more compounds of the invention and about 0.05%-0.15% sucralose, or about 0.10% one or more compounds of the invention and about 0.15% sucralose, or about 0.15% one or more compounds of the invention and about 0.15% sucralose.

In further embodiments, the present invention provides formulations and compositions for pulmonary delivery of one or more compounds of the invention, and optionally, one or more additional active agents, such as those described herein. For example, inhalable preparations comprising one or more compounds of the invention, and optionally, one or more additional active agents such as those described herein, can be produced.

Inhalable preparations include inhalable powders, propellant-containing metering aerosols or propellant-free inhalable solutions Inhalable powders according to the invention containing one or more compounds of the invention, and optionally one or more additional active ingredients including those described herein, may comprise the active ingredients on their own, or a mixture of the active ingredients with physiologically acceptable excipients. In certain such embodiments, the inhalable formulas comprise the compositions of the present invention in an inhalable form. Within the scope of the present invention, the term propellant-free inhalable solutions also includes concentrates or sterile inhalable solutions ready for use. The preparations according to the invention may comprise one or more compounds of the invention and optionally one or more additional active ingredients including those described herein, in one formulation, or in two or more separate formulations.

Physiologically acceptable excipients that may be used to prepare the inhalable powders according to the present invention include, but are not limited to, monosaccharides (e.g., glucose or arabinose), disaccharides (e.g., lactose, saccharose, maltose), oligo- and polysaccharides (e.g., dextran), polyalcohols (e.g., sorbitol, mannitol, xylitol), salts (e.g., sodium chloride, calcium carbonate) or mixtures of these excipients with one another. Suitably, mono- or disaccharides are used, for example, lactose or glucose in the form of their hydrates. Lactose and lactose monohydrate represent exemplary excipients. Excipients for use in the inhalable preparations can have an average particle size of up to about 250 μm, suitably between about 10 μm and about 150 μm, most suitably between about 15 μm and about 80 μm. In certain such embodiments, finer excipient fractions can be added with an average particle size of about 1 μm to about 9 μm. These finer excipients are also selected from the group of possible excipients disclosed throughout. Finally, in order to prepare the inhalable powders according to the present invention, micronised active ingredients (e.g., one or more compounds of the invention and optionally one or more additional agents described throughout), suitably with an average particle size of about 0.5 μm to about 10 μm, more suitably from about 1 μm to about 5 μm, are added to the excipient mixture. Processes for producing the inhalable powders according to the present invention by grinding and micronizing and by finally mixing the ingredients together are routine and well known to those of ordinary skill in the art. The inhalable powders according to the present invention can be prepared and administered either in the form of a single powder mixture which contains one or more compounds of the invention and optionally one or more additional active agents such as those described herein, or in the form of separate inhalable powders, in which one powder contains only one or more compounds of the invention, and another powder contains one or more additional active agents such as those described herein. Methods for preparing the inhalable powders of the present invention, as well as devices for their delivery, are disclosed in U.S. Pat. Nos. 6,696,042 and 6,620,438; U.S. Published Patent Application Nos. 2002/0009418, 2005/0121032, 2005/0121027 and 2005/0123486, the disclosures of each of which are incorporated herein by reference in their entireties.

The inhalable powders according to the present invention may be administered using inhalers well known in the art Inhalable powders according to the present invention which contain a physiologically acceptable excipient in addition to the active agents may be administered, for example, by means of inhalers which deliver a single dose from a supply using a measuring chamber as described in U.S. Pat. No. 4,570,630, or by other means as described in U.S. Pat. Nos. 5,035,237 and 4,811,731, the disclosures of which are incorporated by reference herein in their entireties. The inhalable powders of the present invention can also be administered by dry powder inhalers (DPIs) or pre-metered DPIs (see e.g., U.S. Pat. Nos. 6,779,520, 6,715,486 and 6,328,034, the disclosures of each of which are incorporated herein by reference in their entireties). Suitably, the inhalable powders according to the present invention which contain physiologically acceptable excipients in addition to the active agents are packed into capsules (to produce so-called inhalettes) which are used in inhalers as described, for example, in U.S. Pat. No. 5,947,118, the disclosure of which is incorporated herein by reference in its entirety. An additional DPI that can be used with the powder formulations of the present invention is the Novalizer® by Sofotec (Bad Homburg, Germany). A description of this DPI, as well as methods to formulate powders for use in it, are disclosed in U.S. Pat. Nos. 5,840,279; 5,881,719; 6,071,498; and 6,681,768, the disclosures of which are incorporated herein by reference in their entireties.

According to another embodiment of the present invention, inhalation aerosols containing propellant gas comprising (or consisting essentially of) one or more compounds of the invention, and optionally, one or more additional active ingredients such as those described herein, dissolved in a propellant gas or in dispersed form, can be produced. One or more compounds of the invention, and one or more optional active ingredients, such as those disclosed herein, may be present in separate formulations or in a single preparation, in which all active ingredients are each dissolved, each dispersed, or one or more active components are dissolved and any others are dispersed. The propellant gases which may be used to prepare the inhalation aerosols according to the invention are known in the art. Suitable propellant gases include, but are not limited to, hydrocarbons such as n-propane, n-butane or isobutane and halohydrocarbons such as fluorinated derivatives of methane, ethane, propane, butane, cyclopropane or cyclobutane. The propellant gases may be used on their own or in mixtures thereof. Particularly suitable propellant gases are halogenated alkane derivatives selected from TG134a and TG227.

The propellant-driven inhalation aerosols according to the present invention may also contain other ingredients such as co-solvents, stabilizers, surfactants, antioxidants, lubricants and pH adjusters. All of these ingredients, and suitable commercial sources thereof, are well known in the art.

The inhalation aerosols containing propellant gas according to the present invention may contain up to about 5 wt. % of active substances (or more if required). Aerosols according to the invention contain, for example, about 0.002 wt. % to about 5 wt. %, about 0.01 wt. % to about 3 wt. %, about 0.015 wt. % to about 2 wt. %, about 0.1 wt. % to about 2 wt. %, about 0.5 wt. % to about 2 wt. %, or about 0.5 wt. % to about 1 wt. % of active substances (e.g., one or more compounds of the invention and optionally one or more additional active agents such as those described herein).

In embodiments where the active substance(s) are present in dispersed form, the particles of active substance(s) suitably have an average particle size of up to about 10 µm, suitably from about 0.1 µm to about 5 µm, more suitably from about 1 µm to about 5 µm.

Propellant-driven inhalation aerosols according to certain such embodiments of the present invention may be administered using inhalers known in the art (e.g., MDIs: metered dose inhalers, see e.g., U.S. Pat. Nos. 6,380,046, 6,615,826 and 6,260,549, the disclosures of each of which are incorporated herein by reference in their entireties). Accordingly, in another aspect, the present invention provides pharmaceutical compositions in the form of propellant-driven aerosols combined with one or more inhalers suitable for administering these aerosols. In addition, the present invention provides inhalers which are characterized in that they contain the propellant gas-containing aerosols described throughout. The present invention also provides cartridges which are fitted with a suitable valve and can be used in a suitable inhaler and which contain one or more of the propellant gas-containing inhalation aerosols described throughout. Suitable cartridges and methods of filling these cartridges with the inhalable aerosols containing propellant gas according to the invention are known in the art.

In another embodiment, the present invention provides propellant-free inhalable formulations, such as solutions and suspensions, comprising (or consisting essentially of) one or more compounds of the invention and optionally one or more additional active agents such as those described herein. Suitable solvents for use in such embodiments include aqueous and alcoholic solvents, suitably an ethanolic solution. The solvents may be water on its own or a mixture of water and ethanol. The relative proportion of ethanol compared with water suitably is up to about 70 percent by volume, more suitably up to about 60 percent by volume, or up to about 30 percent by volume. The remainder of the volume is made up of water. The solutions or suspensions containing one or more compounds of the invention and optionally one or more additional active agents, such as those described herein, separately or together, are adjusted to a pH of 2 to 7, using suitable acids or bases. The pH may be adjusted using acids selected from inorganic or organic acids. Examples of suitable inorganic acids include hydrochloric acid, hydrobromic acid, nitric acid, sulfuric acid and phosphoric acid. Examples of suitable organic acids include ascorbic acid, citric acid, malic acid, tartaric acid, maleic acid, succinic acid, fumaric acid, acetic acid, formic acid, propionic acid, etc. Exemplary inorganic acids include hydrochloric and sulfuric acids. It is also possible to use the acids which have already formed an acid addition salt with one or more of the active substances. Exemplary organic acids include ascorbic acid, fumaric acid and citric acid. If desired, mixtures of the above acids may be used, particularly in the case of acids which have other properties in addition to their acidifying qualities, e.g., as flavorings, antioxidants or complexing agents, such as citric acid or ascorbic acid, for example. Hydrochloric acid can be used to adjust the pH.

Co-solvents and/or other excipients may be added to the propellant-free inhalable formulations of the present invention. Suitable co-solvents are those which contain hydroxyl groups or other polar groups, e.g., alcohols—such as isopropyl alcohol, glycols—such as propylene glycol, poly(ethylene glycol), polypropylene glycol), glycol ether, glycerol, poly(oxyethylene alcohols) and poly(oxyethylene fatty acid esters). The terms excipients and additives in this context denote any pharmacologically acceptable substance which is not an active substance but which can be formulated with the active substance or substances in the pharmacologically suitable solvent in order to improve the qualitative properties of the active substance formulation. Suitably, these substances have no pharmacological effect or, in connection with the desired therapy, no appreciable or at least no undesirable pharmacological effect. The excipients and additives include, for example, surfactants such as soy lecithin, oleic acid, sorbitan esters, such as polysorbates, polyvinylpyrrolidone, other stabilizers, complexing agents, antioxidants and/or preservatives which prolong the shelf life of the finished pharmaceutical formulation, flavorings, vitamins and/or other additives known in the art. The additives also include pharmacologically acceptable salts such as sodium chloride as isotonic agents.

Exemplary excipients include antioxidants such as ascorbic acid, vitamin A, vitamin E, tocopherols and similar vitamins and provitamins occurring in the human body.

Preservatives may be used to protect the inhalable formulations disclosed herein from contamination with pathogens. Suitable preservatives are those which are known in the art, particularly cetyl pyridinium chloride, benzalkonium chloride or benzoic acid or benzoates such as sodium benzoate in the concentration known from the prior art. The preservatives mentioned above are suitably present in concentrations of up to about 50 mg/100 ml, more suitably between about 5 and about 20 mg/100 ml. Alternatively, the inhalable formulations can be prepared without preservatives, for example, in unit-dose forms, such as described herein.

The propellant-free inhalable formulations according to the present invention can be administered using inhalers of the kind which are capable of nebulizing a small amount of a liquid formulation in the therapeutic dose within a few seconds to produce an aerosol suitable for therapeutic inhalation. Suitable inhalers are those in which a quantity of less than about 100 µL, less than about 50 µL, or between about 10 µL and about 30 µL of active substance solution can be nebulized in one spray action to form an aerosol with an average particle size of less than about 20 µm, suitably less than about 10 µm, in such a way that the inhalable part of the aerosol corresponds to the therapeutically effective quantity.

Suitable apparatuses for propellant-free delivery of a metered quantity of a liquid pharmaceutical composition according to the present invention are described for example in U.S. Pat. Nos. 5,497,944; 5,662,271; 5,964,416; 6,402,055; 6,497,373; 6,726,124; and 6,918,547, the disclosures of which are incorporated herein by reference in their entireties. In another embodiment, the present invention provides pharmaceutical formulations in the form of propellant-free inhalable formulations, such as solutions or suspensions, as described herein, combined with a device suitable for administering such formulations.

The propellant-free inhalable formulations, e.g., solutions or suspensions, according to the present invention may take the form of concentrates or sterile inhalable solutions or suspensions ready for use. Formulations ready for use may be produced from the concentrates, for example, by the addition of isotonic saline solutions. Sterile formulations ready for use may be administered using energy-operated fixed or portable nebulizers which produce inhalable aerosols by means of ultrasound or compressed air by the Venturi principle or other principles.

The present invention also provides fine particle dosages of one or more compounds of the invention and optionally one or more additional active agents such as those described herein. A delivered fine particle dose (FPD) of one or more compounds of the invention administered by inhalation herein is not limited, and may generally be in a range from about 1 to about 50 μg, including about 5, 10, 15, 20, 30 and 40 μg. The correct metered dose loaded into an inhaler to be used for the purpose of administration can be adjusted for predicted losses such as retention and more or less efficient de-aggregation of the inhaled dose.

Excipient particles having a physical median particle size larger than about 25 μm and having a very narrow particle size distribution with generally less than 5% of the particles by mass being below 10 μm generally show good flow properties, and are suitable for use in mixtures together with one or more compounds of the invention and optionally one or more additional active agents, such as those described herein. For inhalation purposes, carrier particles having a mass median particle size in a range from about 10 to about 250 μm are typically selected, including about 30, 50, 70, 100, 130, 160, 190, and 220 μm. The median particle size chosen within this range depends on many factors, e.g. type of carrier substance, degree of powder flowability to be attained, type of inhaler and ease of de-aggregation during inhalation of the resulting medicament. Commercial grades of Respitos are available (lactose monohydrate from DMV of several defined particle size distributions up to 400 μm) suitable as particular excipients to be used in formulations containing one or more compounds of the invention, e.g. grade SV003. Uniform homogeneous one or more compounds of the invention powder formulations having a physical median particle size down to about 10 μm can also provide good flow properties when the particles have been modified to have a very smooth surface, thereby improving the flow properties of the formulation.

A practical lower limit for volumetric dose forming for such inhalable powder formulations is in a range of about 0.5 to 1 mg. Smaller doses can be difficult to produce and still maintain a low relative standard deviation between doses in the order of 10%. Typically, though, dose masses range from about 1 to 10 mg.

Suitable excipients for inclusion in the one or more compounds of the invention powder formulations include, but are not limited to, monosaccharides, disaccharides, polylactides, oligo- and polysaccharides, polyalcohols, polymers, salts or mixtures from these groups, e.g. glucose, arabinose, lactose, lactose monohydrate, lactose anhydrous (i.e., no crystalline water present in lactose molecule), saccharose, maltose, dextran, sorbitol, mannitol, xylitol, sodium chloride and calcium carbonate.

Excipients for use with one or more compounds of the invention and optionally one or more additional active agents, such as those described herein, generally are selected from among excipients which have good moisture qualities in the sense that the substance will not adversely affect the active agent fine particle dose (FPD) for the shelf life of the product regardless of normal changes in ambient conditions during storage. Suitable "dry" excipients are well known in the art and include those disclosed herein. For example, lactose can be selected as a dry excipient, or lactose monohydrate can be used in a formulation with one or more compounds of the invention (and optionally one or more additional active agents, such as those described herein). Lactose has the inherent property of having a low and constant water sorption isotherm. Excipients having a similar or lower sorption isotherm can also be used.

As discussed throughout, and in a further aspect of the present invention, one or more compounds of the invention may be mixed or formulated with one or more additional active agents such as those described herein in the dry powder or other inhalable formulations. The present invention also encompasses the use of one or more compounds of the invention where a combination of one or more compounds of the invention with other agents, such as those described herein, constitute a formulation from which metered doses are then produced, filled and sealed into dry, moisture-tight, high barrier seal containers intended for insertion into a DPI to be administered according to a particular dosing regime or as needed by the user. Suitable additional active agents include those disclosed throughout, for example, anticholesterolemics, anticoagulants, anti-obesity or anti-diabetic drugs.

A sealed, dry, high barrier container can be loaded with a powder form of one or more compounds of the invention and optionally one or more additional active agents, such as those described herein, in the form of a blister and may comprise a flat dose bed or a formed cavity in aluminum foil or a molded cavity in a polymer material, using a high barrier seal foil against ingress of moisture, e.g. of aluminum or a combination of aluminum and polymer materials. The sealed, dry, high barrier container may form a part of an inhaler device or it may form a part of a separate item intended for insertion into an inhaler device for administration of pre-metered doses.

The present invention also provides inhalable spray pharmaceutical compositions comprising (or consisting essentially of), a suitable concentration to provide a therapeutically effective dose of one or more compounds of the invention, and one or more pharmaceutically acceptable carrier, stabilizer or excipient, wherein the one or more compounds of the invention is in a solution form and wherein at least one of the pharmaceutically acceptable carriers or excipients is sucralose dissolved in the solution. Such inhalable spray pharmaceutical compositions when used with a suitable device provide a fine spray of the components (including active and non-active components) having an average particle size of about 1 μm to about 5 μm. Such inhalable spray pharmaceutical compositions of the present invention can be formulated for pulmonary delivery using, for example, a suitable device or inhaler. Suitably the amount of one or more compounds of the invention in such inhalable spray pharmaceutical compositions is about 0.1% to about 10% by weight and the amount of sucralose in such inhalable spray pharmaceutical compositions is about 0.05% to about 0.15% by weight, though other suitable amounts will readily be determined by the ordinarily skilled artisan.

In certain embodiments, a pharmaceutical composition comprising a compound of the invention and one or more additional therapeutic agents are administered to a patient.

In certain embodiments, compounds of the invention and one or more additional therapeutic agents are administered to a patient in separate compositions under one or more of the following conditions: at different periodicities, at different durations, at different concentrations, by different administration routes, etc. In one such embodiment, the compound of Formula I is administered prior to the one or more additional therapeutic agents, e.g., 0.5, 1, 2, 3, 4, 5, 10, 12, or 18 hours, 1, 2, 3, 4, 5, or 6 days, 1, 2, 3, or 4 weeks prior to the administration of the therapeutic agent(s). In another such embodiment, the compound is administered after the one or more additional therapeutic agents, e.g., 0.5, 1, 2, 3, 4, 5, 10, 12, or 18 hours, 1, 2, 3, 4, 5, or 6 days, 1, 2, 3, or 4 weeks after the administration of the therapeutic agent(s). In another such embodiment, the compound of Formula I and the one or more additional therapeutic agents are administered concurrently but on different schedules, e.g., the compound of Formula I is administered daily while the one or more additional therapeutic agents are administered once every two days, once every three days, once every four days, once every five days, once every six days, once a week, once every two weeks, once every three weeks, once every four weeks, etc.

General Synthesis of β-Hydroxy-γ-Aminophosphonates

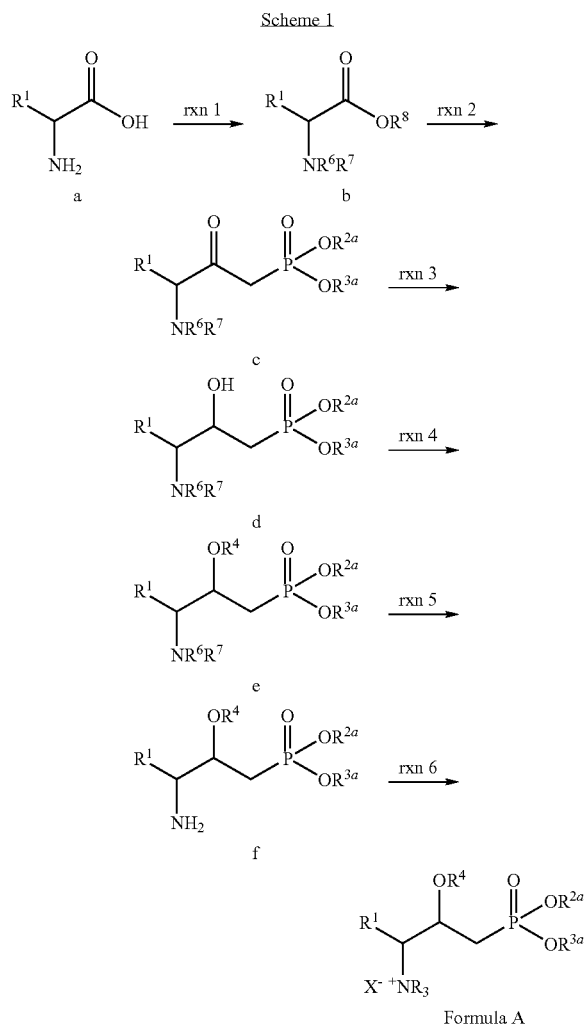

Scheme 1 depicts a general synthesis of β-hydroxy-γ-aminophosphonate and β-hydroxy-γ-aminophosphonate analogs of Formula A, wherein R is selected from the group consisting of hydrogen and lower alkyl, $R^1$ is selected from the group consisting of hydrogen, optionally substituted alkyl, aralkyl, optionally substituted cycloalkyl, optionally substituted alkenyl, optionally substituted alkynyl, optionally substituted aryl, optionally substituted heteroaryl and optionally substituted heterocyclo, $R^{2a}$ and $R^{3a}$ are independently selected from the group consisting of optionally substituted alkyl, aralkyl and optionally substituted aryl, $R^4$ is selected from the group consisting of hydrogen, optionally substituted alkyl and $COR^5$, $R^5$ is selected from the group consisting of optionally substituted alkyl, aralkyl, optionally substituted cycloalkyl, optionally substituted alkenyl, optionally substituted alkynyl, optionally substituted aryl, optionally substituted heteroaryl and optionally substituted heterocyclo, and $X^-$ is a pharmaceutically acceptable anion.

In reaction (i.e., rxn) 1, the amine functionality of a racemic amino acid a (e.g., D,L-leucine) is protected and the carboxylic acid is converted to an ester to give b, wherein $R^6$ is an amine protecting group and $R^7$ is selected from the group consisting of hydrogen and amine protecting group, or $R^6$ and $R^7$ taken together represent an amine protecting group, and $R^8$ is selected from the group consisting of optionally substituted alkyl, aralkyl, and optionally substituted aryl. Suitable amine protecting groups and synthetic methods used to introduce amine protecting groups are well known in the art of organic synthesis. See, for example, Greene and Wuts, "Protective Groups in Organic Synthesis," 3rd Ed., pp. 17-245 (J. Wiley & Sons, 1999). Likewise, synthetic methods used to esterify a carboxylic acid are well known in the art. The amine of a may be protected before esterification, after esterification or simultaneously with esterification. In an exemplary embodiment, the amino acid a is treated with benzyl bromide in the presence of potassium carbonate to give b, wherein $R^6$, $R^7$ and $R^8$ are each benzyl. In certain embodiments, the reaction is carried in a solvent system comprising a $C_1$-$C_4$ alcohol (e.g., methanol) and water or acetonitrile and water. In certain embodiments, the reaction is carried out at reflux temperature. In certain embodiments, b is used in the next synthetic step without purification.

In reaction 2, b is condensed with $Li^+(^-CH_2P(O)(OR^{2a})(OR^{3a})$ to give a β-keto-γ-aminophosphonate c. In certain embodiments, $R^{2a}$ and $R^{3a}$ are each lower alkyl (e.g., methyl) or aralkyl (e.g., benzyl). In certain embodiments, the condensation is carried out in tetrahydrofuran at temperature ranging from about −78° C. to about −20° C., e.g., about −50° C. The product c can be used in the next synthetic reaction without further purification.

In reaction 3, the oxo group, i.e., C=O, of a β-keto-γ-aminophosphonate c is reduced to give a β-hydroxy-γ-aminophosphonate d. In certain embodiments, the reducing agent is a borohydride reducing agent, e.g., sodium borohydride. In certain embodiments, the reaction is carried out in a solvent system comprising a $C_1$-$C_4$ alcohol (e.g., methanol) and tetrahydrofuran. In a further embodiment, the solvent system comprises about 5% to about 15% methanol in tetrahydrofuran (v/v), e.g., about 10% methanol and about 90% tetrahydrofuran (v/v). In certain embodiments, the reduction is carried out a temperature from about −30° C. to about −20° C., e.g., about −10° C. to about 5° C. In certain embodiments, a compound of Formula d is used in the next synthetic reaction without purification.

In reaction 4, the hydroxy group of β-hydroxy-γ-aminophosphonate d is alkylated or acylated to give e, wherein $R^4$ is optionally substituted alkyl or $COR^5$, respectively. The optionally substituted alkyl group can be introduced via reaction of d with $R^4L^2$ wherein $L^2$ is a leaving group, e.g., methyl triflate, i.e., $MeOSO_2CF_3$. In certain embodiments, the reaction is carried out in an inert organic solvent, e.g., tetrahydrofuran, dichloromethane, acetonitrile, dimethylformamide, etc. The $COR^5$ group can be introduced via reaction of d with $R^5COL^1$ wherein $L^1$ is a leaving group, e.g., acetyl chloride, i.e., MeCOCl. Alternatively, β-hydroxy-γ-aminophosphonate d can be used in the next synthetic step without further chemical modification, i.e., $R^4$ is hydrogen.

In reaction 5, the amine protecting group(s) of e is(are) removed, i.e., $R^6$ is an amine protecting group and $R^7$ is hydrogen, or $R^6$ and $R^7$ are both an amine protecting groups, or $R^6$ and $R^7$ taken together represent an amine protecting group, to give amine f. In certain embodiments, $R^6$ and $R^7$ are benzyl. In a further embodiment, the benzyl groups are removed, i.e., the amine is deprotected, under an atmosphere of hydrogen gas using palladium on carbon as the catalyst. In a further embodiment the deprotection is carried out in a solvent selected from the group consisting of $C_1$-$C_4$ alcohol (e.g., methanol) tetrahydrofuran, acetonitrile and dichloromethane. In a further embodiment, the deprotection is carried out a temperature from about 20° C. to about 50° C., e.g., about 37° C. to about 42° C. In certain embodiments, the reaction mixture is filtered through a pad of celite and the solvent(s) is removed by evaporation. In certain embodiments, amine f is used in the next step without additional purification.

In reaction 6, the amine f is alkylated with RX to give a quaternary ammonium compound of Formula A. In certain embodiments, R is lower alkyl and X is halo. In a further embodiment, the halo is iodide. In a further embodiment, RX is methyl iodide, i.e., the compound of Formula A is a trimethylammonium compound. In certain embodiments, the alkylation is carried out in the presence of a base, such as potassium carbonate. In certain embodiments, the alkylation is carried out in a solvent selected from the group consisting of $C_1$-$C_4$ alcohol (e.g., methanol), tetrahydrofuran, acetonitrile and dichloromethane. In certain embodiments, the alkylation is carried out a temperature from about 20° C. to about 50° C., e.g., about 37° C. to about 42° C. In certain embodiments, the reaction mixture is filtered and the solvent is removed by evaporation to give a compound of Formula A. In certain embodiments, a compound of Formula A is purified by crystallization. In certain embodiments, a compound of Formula A is dissolved in a solvent selected from the group consisting of $C_1$-$C_4$ alcohol (e.g., methanol), tetrahydrofuran, acetonitrile and dichloromethane to give a solution and a solvent, i.e., an anti-solvent, selected from the group consisting of acetone, methyl ethyl ketone and ethyl acetate is added to induce crystallization. In further embodiments, the anti-solvent is ethyl acetate. The quaternary ammonium compound can form a pharmaceutically acceptable salt with any suitable pharmaceutically acceptable anion, $X^-$, to provide a compound of Formula A.

Scheme 2

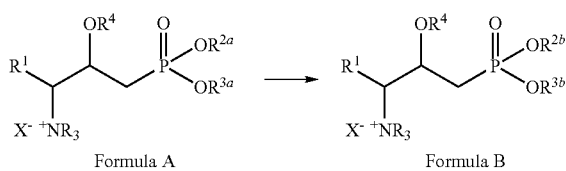

Formula A          Formula B

Scheme 2 depicts the synthesis of compounds of Formula B wherein R is selected from the group consisting of hydrogen and lower alkyl, $R^1$ is selected from the group consisting of hydrogen, optionally substituted alkyl, aralkyl, optionally substituted cycloalkyl, optionally substituted alkenyl, optionally substituted alkynyl, optionally substituted aryl, optionally substituted heteroaryl and optionally substituted heterocyclo, $R^{2b}$ and $R^{3b}$ are independently selected from the group consisting of hydrogen and monovalent pharmaceutically acceptable cation, or taken together $R^{2b}$ and $R^{3b}$ represent a divalent pharmaceutically acceptable cation, and $X^-$ is a pharmaceutically acceptable anion, or $X^-$ and $R^{2b}$ are absent and the compound of Formula B is a zwitterion, and $R^4$ is selected from the group consisting of hydrogen, optionally substituted alkyl and $COR^5$.

In Scheme 2, $R^{2a}$ and $R^{3a}$ are removed from a compound of Formula A to give a compound of Formula B. Compounds of Formula B wherein $R^{2b}$ and $R^{3b}$ are hydrogen may be prepared from phosphonate esters using known cleavage methods. For example, silyl halides are generally used to cleave various phosphonate esters and give the desired phosphonic acid upon mild hydrolysis of the resulting silyl phosphonate esters. When needed, acid scavengers (for example, HMDS) can be used for the acid sensitive compounds. Such silyl halides include TMSCl (*J. Org. Chem.* 28:2975 (1963)), TMSBr (*Tetrahedron Lett.* 155 (1977)) and TMSI (*J. Chem. Soc., Chem. Commu.* 870 (1978)). Alternatively, phosphonate esters can be cleaved under strong acid conditions (*Tetrahedron Lett.* 33:4137 (1992); *Synthesis-Stuttgart* 10:955 (1993)). Those phosphonate esters can also be cleaved via dichlorophosphonates prepared by treating the phosphonate esters with halogenating agents such as $PCl_5$, $SOCl_2$ and $BF_3$ (*J. Chem. Soc.* 238 (1961)) followed by aqueous hydrolysis to give the phosphonic acids. Aryl and benzyl phosphonate esters can be cleaved under hydro geno lysis conditions (*Synthesis* 412 (1982); *J. Med. Chem.* 28:1208 (1985)) or metal reduction conditions (*J. Chem. Soc.* 99:5118 (1977)). Electrochemical (*J. Org. Chem.* 44:4508 (1979)) and pyrolysis (*Synth. Commu.* 10:299 (1980)) conditions have also been used to cleave various phosphonate esters.

Thus, in one embodiment, $R^{2a}$ and $R^{3a}$ are benzyl. In a further embodiment, the benzyl groups are removed under an atmosphere of hydrogen gas and palladium on carbon is the catalyst. In certain embodiments the benzyl groups are removed in a solvent selected from the group consisting of $C_1$-$C_4$ alcohol (e.g., methanol), tetrahydrofuran, acetonitrile and dichloromethane. In certain embodiments, the benzyl groups are removed at temperature from about 20° C. to about 50° C., e.g., about 37° C. to about 42° C. In certain embodiments, the reaction mixture is filtered through a pad of celite and the solvent(s) are removed by evaporation to give a compound of Formula B wherein $R^{2b}$ and $R^{3b}$ are hydrogen.

In additional embodiments, $R^{2a}$ and $R^{3a}$ of a compound of Formula III, or a stereoisomer or mixture of stereoisomers thereof, are methyl. In certain embodiments, the methyl groups are removed using bromo trimethylsilane. In one embodiment the methyl groups are removed in a solvent selected from the group consisting of tetrahydrofuran and dichloromethane. In additional embodiments, the methyl groups are removed at temperature from about 20° C. to about 50° C., e.g., from about 37° C. to about 42° C. In additional embodiments, the solvents are removed by evaporation. In additional embodiments, the reaction mixture is dissolved in water. In additional embodiments, the reaction mixture is filtered and the solvent(s) are removed by evaporation to give a compound of Formula B, or a stereoisomer or mixture of stereoisomers thereof, wherein $R^{2b}$ and $R^{3b}$ are hydrogen.

In certain embodiments, a compound of Formula B is purified by crystallization. In certain embodiments, a compound of Formula A is dissolved in a solvent selected from the group consisting of $C_1$-$C_4$ alcohol (e.g., methanol), tetrahydrofuran, and acetonitrile to give a solution and a solvent, i.e., an anti-solvent, selected from the group consisting of acetone, methyl ethyl ketone and ethyl acetate is added to induce crystallization. In further embodiments, the anti-solvent is ethyl acetate. The quaternary ammonium compound can form a pharmaceutically acceptable salt with any suitable pharmaceutically acceptable anion, $X^-$, to provide a compound of Formula B.

Scheme 3

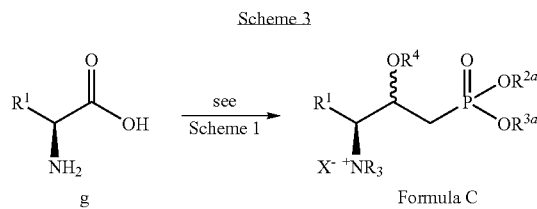

In Scheme 3, a compound of Formula C is prepared as described above in Scheme 1, starting from an amino acid g, i.e., a L-amino acid, e.g., L-leucine.

Scheme 4

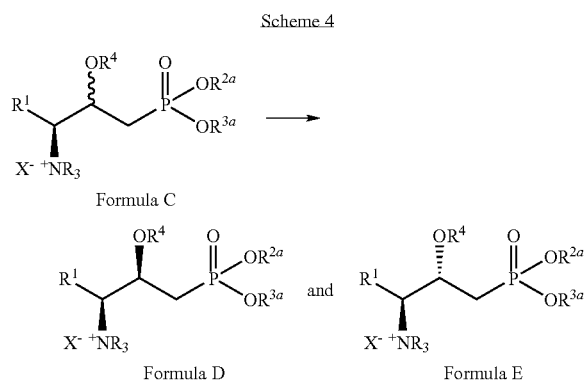

In Scheme 4, the diastereomers of a compound of Formula C are separated into compounds of Formula D, i.e., the 2R, 3S-isomer, and Formula E, i.e., the 2S, 3S-isomer. In certain embodiments, the diastereomers of a compound of Formula C are separated by crystallization. In certain embodiments, the crystallization comprises: (a) dissolving a compound of Formula C in a solvent or solvent system, i.e., a mixture of solvents, e.g., methanol/water, ethanol/water, tetrahydrofuran/water, acetonitrile/water, etc., to give a solution; (b) allowing precipitation to occur; and (c) separating crystalline product from said solution. In certain embodiments, the solution is a homogeneous solution. In certain embodiments, the solvent or solvent system is selected from the group consisting of dichloromethane, methanol, methanol/water, ethanol, ethanol/water, isopropanol, isopropanol/water, tetrahydrofuran, tetrahydrofuran/water, acetonitrile and acetonitrile/water. In certain embodiments, precipitation of the desired product, i.e., a compound of Formulae D or E, is induced by adding an anti-solvent. In further embodiments, the anti solvent is selected from the group consisting of hexane, ethyl acetate, acetone, methyl ethyl ketone and methyl t-butyl ether, particularly ethyl acetate.

In additional embodiments, precipitation of the product during crystallization is induced by cooling the solution. In a further embodiment, the solution is cooled to about 10° C., to about 5° C. or to about 0° C.

In additional embodiments, the solution is heated before the addition of the anti-solvent, during the addition of the anti-solvent or after the addition of the anti-solvent.

In certain embodiments, the crystalline product is isolated by filtration.

Scheme 5

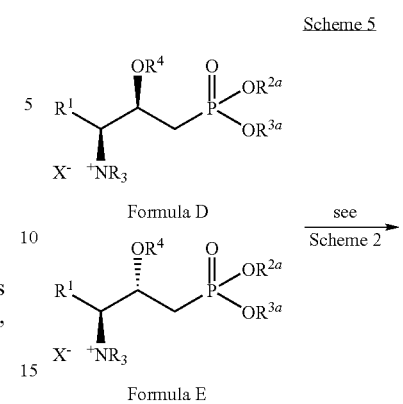

In Scheme 5, a compound of Formula F is prepared as described above in Scheme 2, starting from a compound of Formula D. In a similar fashion, a compound of Formula G is prepared from a compound of Formula E.

Scheme 6

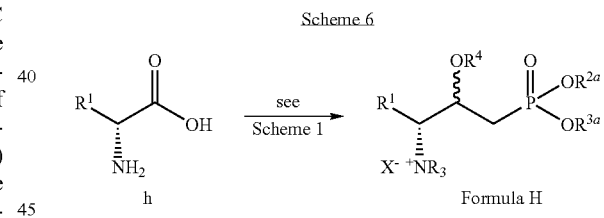

In Scheme 6, a compound of Formula H is prepared as described above in Scheme 1, starting from an amino acid h, i.e., a D-amino acid, e.g., D-leucine.

Scheme 7

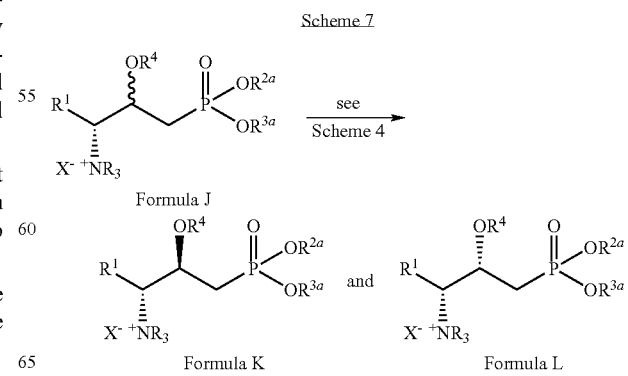

In Scheme 7, a compound of Formula K, i.e., the 2R, 3R-isomer, and Formula L, i.e., the 2S, 3R-isomer, are prepared as described above in Scheme 4, starting from a compound of Formula J.

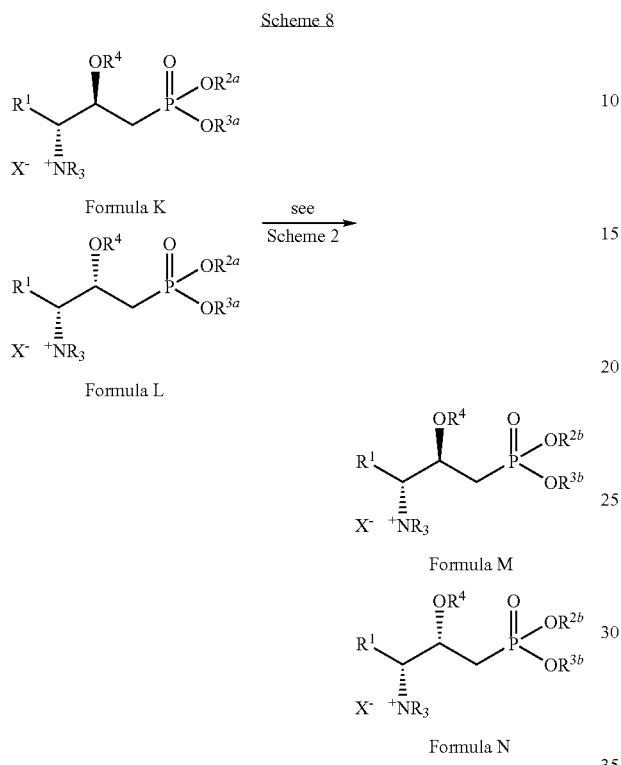

In Scheme 8, a compound of Formula M is prepared as described above in Scheme 2, starting from a compound of Formula K. In a similar fashion, a compound of Formula N is prepared from a compound of Formula L.

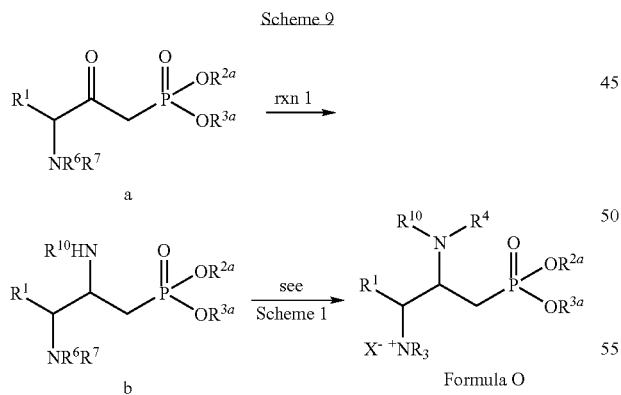

Scheme 9 depicts the synthesis of β-amino-γ-aminophosphonate and β-amino-γ-aminophosphonate analogs of Formula O. In reaction 1, the oxo group, i.e., C=O, of a β-keto-γ-aminophosphonate a is converted to β-amino-γ-aminophosphonate b via reductive amination. In one embodiment, a is reacted with $H_2NR^{10}$ in the presence of a reducing agent, such as, but not limited to, $NaCNBH_3$ or $NaBH(OAc)_3$, in an organic solvent such as, but not limited to, tetrahydrofuran. A compound of Formula O can be prepared from b using the methods described in Scheme 1 and routine amine protection/deprotection strategies well-known to one of ordinary skill in the art.

It will be readily apparent to one of ordinary skill in the relevant arts that other suitable modifications and adaptations to the methods and applications described herein may be made without departing from the scope of the invention or any embodiment thereof. It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the claims. Having now described the present invention in detail, the same will be more clearly understood by reference to the following examples, which are included herewith for purposes of illustration only and are not intended to be limiting of the invention.

EXAMPLE 1

Synthesis of (2R,3S)-(2-hydroxy-5-methyl-3-trimethylamonium-hexyl)-phosphonic acid dimethyl ester; iodide

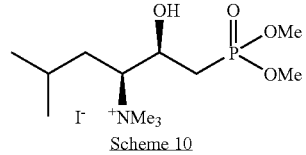

Scheme 10

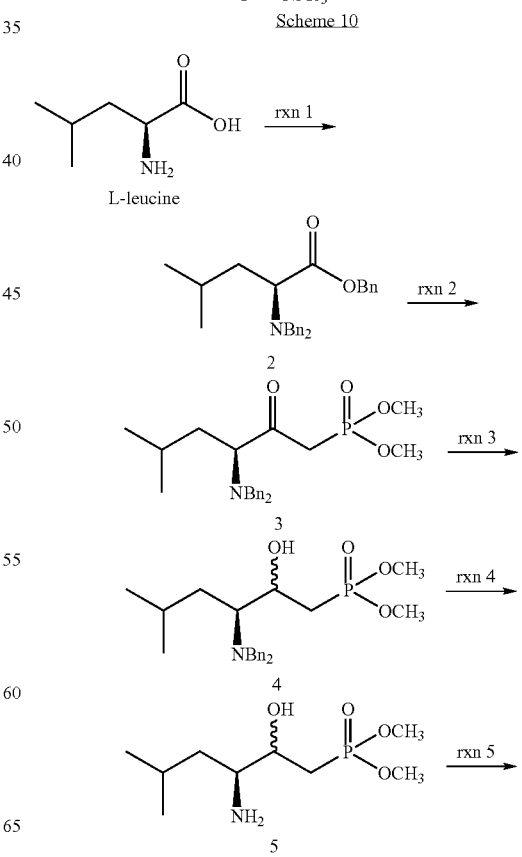

-continued

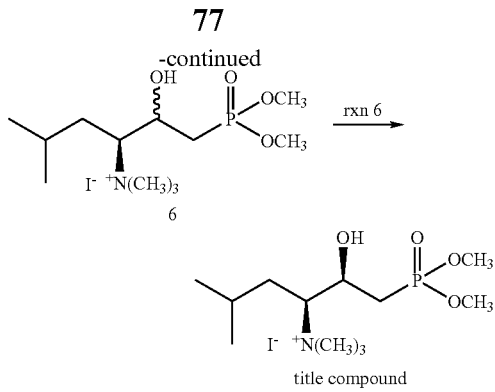

title compound

Scheme 10 depicts the synthesis of (2R,3S)-(2-hydroxy-5-methyl-3-trimethylamonium-hexyl)-phosphonic acid dimethyl ester; iodide.

Reaction 1: 2.5 g of L-leucine (19.05 mmol) was taken up in methanol (10 ml) and $K_2CO_3$ (32.40 mmol) was added. The mixture was stirred and benzyl bromide (62.89 mmol) was slowly added. The reaction mixture was heated under reflux for 24 h. The solvent was removed under reduced pressure. Ethyl acetate was added, the salts were removed by filtration and the filtrate was concentrated under reduced pressure to give compound 2. The residual oil was dissolved in anhydrous THF (12 ml) (solution A).

Reaction 2: A solution of dimethylmethylphosphonate (60.98 mmol) in anhydrous THF (12 ml) was cooled at −50° C. and a solution of n-BuLi in hexane (2.4 M, 67.08 mmol) was slowly added. The resulting solution was stirred at −50° C. for 1 h and added to solution A from reaction 1 above. The reaction mixture was stirred at −50° C. for 3 h before the addition of solution of HCl 5% (v/v). The reaction mixture was concentrated under reduced pressure. The residual oil was dissolved in ethyl acetate, and washed with 10 ml portions of water. The organic phase was dried over anhydrous $Na_2SO_4$ and filtered. The solvent was evaporated to give compound 3 as a crude oil.

Reaction 3: A mixture of the crude oil (3-dibenzylamino-5-methyl-2-oxohexyl)-phosphonic acid dimethyl ester, i.e., compound 3, obtained in reaction 2, was dissolved in about 10% methanol and about 90% THF (v/v) and cooled at −10° C. $NaBH_4$ (19.05 mmol) was added to the mixture in small portions with vigorous stirring. The mixture was stirred at temperature of −10 to 5° C. for 4 h and HCl 5% (v/v) was added. The reaction mixture was concentrated under reduced pressure. The residual oil was dissolved in ethyl acetate, and washed with 10 ml portions of water. The organic phase was dried over anhydrous $Na_2SO_4$ and filtered. The solvent was evaporated off to leave (3-dibenzylamino-2-hydroxy-5-methyl-hexyl)-phosphonic acid dimethyl ester, compound 4, as a crude oil. $^{31}P$ NMR (at 200 MHz, $CDCl_3$) indicated an 80:20 ratio of 2R,3S (δ 34.53) to 2S,3S (δ 35.15) isomers. (3-Dibenzylamino-2-hydroxy-5-methyl-hexyl)-phosphonic acid dimethyl ester can be isolated by chromatography or used in the next hydrogenolysis step directly without isolation.

Reaction 4: A diastereomeric mixture of the crude (3-dibenzylamino-2-hydroxy-5-methyl-hexyl)-phosphonic acid dimethyl ester, compound 4, obtained in reaction 3, was treated with palladium-carbon (2.0% wt) as the catalyst in methanol (40 mL). The mixture reaction was stirred for 12 h under a hydrogen gas atmosphere at 37-42° C., and after this period of time, the mixture was filtered through a pad of Celite, and the solvents were removed under reduced pressure to leave (3-amino-2-hydroxy-5-methyl-hexyl)-phosphonic acid dimethyl ester, compound 5, as a crude oil.

Reaction 5: A mixture of the crude (3-amino-2-hydroxy-5-methyl-hexyl)-phosphonic acid dimethyl ester, i.e., compound 5, obtained in reaction 4 was dissolved in methanol (30 mL) and $K_2CO_3$ (33.38 mmol) and $CH_3I$ (66.67 mmol) were added. The reaction mixture was stirred for 12 h at 34-37° C., and after this period of time was filtered and the solvent was removed under reduced pressure off to leave (3-trimethylamonium-2-hydroxy-5-methyl-hexyl)-phosphonic acid dimethyl ester; iodide, compound 6, as a crude oil. The diastereomeric mixture was analyzed by $^{31}P$ NMR (at 200 MHz, $CDCl_3$), to give compound of Formula 2R,3S (δ 31.35) and 2S,3S (δ 30.91) in the ratio 76:24, respectively.

Reaction 6: The (3-trimethylamonium-2-hydroxy-5-methyl-hexyl)-phosphonic acid dimethyl ester; iodide, i.e., compound 6, from reaction 5 was dissolved in methanol. Crystallization was induced by the addition of ethyl acetate. The product that crystallized was filtered and dried under reduced pressure to give 2.1 g (26.93%) of the title compound.

$^1H$ NMR (400 MHz, $CDCl_3$) δ 1.06 (d, J=6.8 Hz, 3H, $(CH_3)_2CH$), 1.08 (d, J=6.4 Hz, 3H, $(CH_3)_2CH$), 1.50 (dd, J=13.6, 9.2 Hz, 1H, $CH_2CH$), 1.73 (m, 1H, $CH(CH_3)_2$) 1.89 (ddd, J=13.6, 8.8, 4.2 Hz, 1H, $CH_2CH$), 2.49 (ddd, J=18.6, 15.6, 8.6 Hz, 1H, $CH_2P$), 2.63 (ddd, J=19.2, 15.6, 4.8 Hz, 1H, $CH_2P$), 3.45 (s, 9H, $(CH_3)_3N$), 3.78 (d, J=10.8 Hz, 3H, $(CH_3))_2P$), 3.80 (d, J=10.8 Hz, 3H, $(CH_3O)_2P$), 3.99 (d, J=8.8 Hz, 1H, CHN), 4.43 (m, 1H, CHOH).

$^{13}C$ NMR (100 MHz, $CDCl_3$) δ 21.95 ($(CH_3)_2CH$), 23.76 ($(CH_3)_2CH$), 26.78 ($CH(CH_3)_2$), 32.47 (d, J=135.1 Hz, $CH_2P$), 38.03 ($CH_2CH$), 53.35 ($(CH_3O)_2P$), 54.12 ($(CH_3)_3N$), 67.30 (CHN), 73.63 (CHOH). $^{31}P$ NMR (200 MHz, $CDCl_3$) δ 31.31.

EXAMPLE 2

Synthesis of (2R,3S)-(2-hydroxy-5-methyl-3-trimethylamonium-hexyl)-phosphonic acid; iodide

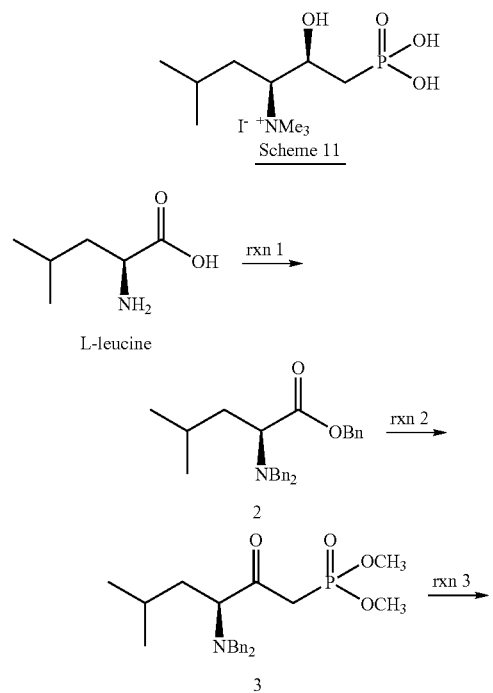

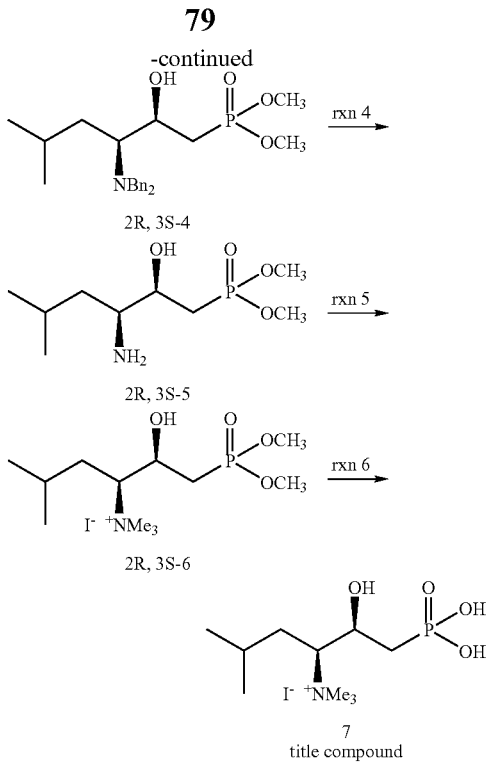

7
title compound

Scheme 11 depicts the synthesis of (2R,3S)-(2-hydroxy-5-methyl-3-trimethylamonium-hexyl)-phosphonic acid; iodide.

Reaction 1: 10 g of L-leucine (76.23 mmol) was taken up in methanol (40 ml) and $K_2CO_3$ (129.60 mmol) was added. The mixture was stirred and benzyl bromide (251.56 mmol) was slowly added. The reaction mixture was heated under reflux for 24 h. The solvent was removed under reduced pressure. Ethyl acetate was added, the salts were removed by filtration and the filtrate was concentrated under reduced pressure to give compound 2. The residual oil was dissolved in anhydrous THF (45 ml) (solution A).

Reaction 2: A solution of dimethylmethylphosphonate (243.92 mmol) in anhydrous THF (45 ml) was cooled at −50° C. and a solution of n-BuLi in hexane (2.4 M, 268.32 mmol) was slowly added. The resulting solution was stirred at −50° C. for 1.5 h and added to solution A from reaction 1 above. The reaction mixture was stirred at −50° C. for 3 h before the addition of solution of HCl 5% (v/v). The reaction mixture was concentrated under reduced pressure. The residual oil was dissolved in ethyl acetate, and washed with 30 ml portions of water. The organic phase was dried over anhydrous $Na_2SO_4$ and filtered. The solvent was evaporated to give compound 3 as a crude oil.

Reaction 3: A mixture of the crude oil (3-dibenzylamino-5-methyl-2-oxohexyl)-phosphonic acid dimethyl ester, i.e., compound 3, obtained in reaction 2, was dissolved in about 10% methanol and about 90% THF (v/v) and cooled at −10° C. $NaBH_4$ (68.58 mmol) was added to the mixture in small portions with vigorous stirring. The mixture was stirred at temperature of −10 to 5° C. for 4 h and HCl 5% (v/v) was added. The reaction mixture was concentrated under reduced pressure. The residual oil was dissolved in ethyl acetate, and washed with 30 ml portions of water. The organic phase was dried over anhydrous $Na_2SO_4$ and filtered. The solvent was evaporated off to leave (3-dibenzylamino-2-hydroxy-5-methyl-hexyl)-phosphonic acid dimethyl ester as a crude oil. $^{31}P$ NMR (at 200 MHz, $CDCl_3$) indicated an 80:20 ratio of 2R,3S (δ 34.53) to 2S,3S (δ 35.15) isomers. The diastereomeric mixture was purified by flash chromatography on silica gel using hexane/ethyl acetate as the eluent to afford compound 2R,3S-4 (20.753 g; 64.9% yield; $^{31}P$ NMR at 200 MHz, $CDCl_3$; δ 34.61).

Reaction 4: 10.365 g of (2R,3S)-3-dibenzylamino-2-hydroxy-5-methyl-hexyl)-phosphonic acid dimethyl ester, compound 2R,3S-4, obtained in reaction 3, was treated with palladium-carbon (2.0% wt) as the catalyst in methanol (40 mL). The mixture reaction was stirred for 12 h under a hydrogen gas atmosphere at 37-42° C., and after this period of time, the mixture was filtered through a pad of Celite, and the solvents were removed under reduced pressure to leave (2R,3S)-3-amino-2-hydroxy-5-methyl-hexyl)-phosphonic acid dimethyl ester, compound 2R,3S-5, as a crude oil.

Reaction 5: The crude (2R,3S)-3-amino-2-hydroxy-5-methyl-hexyl)-phosphonic acid dimethyl ester, i.e., compound 2R,3S-5, obtained in reaction 4 was dissolved in methanol (30 mL) and $K_2CO_3$ (43.26 mmol) and $CH_3I$ (86.52 mmol) were added. The reaction mixture was stirred for 12 h at 32-35° C., and after this period of time was filtered and the solvent was removed under reduced pressure off to leave (2R,3S)-(3-trimethylamonium-2-hydroxy-5-methyl-hexyl)-phosphonic acid dimethyl ester; iodide, compound 2R,3S-6, as a crude oil. $^{31}P$ NMR (at 200 MHz, $CDCl_3$) indicated that the product had 2R,3S stereochemistry (δ 31.23).

Reaction 6: The crude (2R,3S)-3-trimethylamonium-2-hydroxy-5-methyl-hexyl)-phosphonic acid dimethyl ester; iodide, i.e., compound 2R,3S-6, obtained in reaction 5 was treated with bromotrimethylsilane (54.39 mmol) in dichloromethane under nitrogen atmosphere. The mixture reaction was stirred for 4 h at 37-42° C., and after this period of time the volatile materials were evaporated under reduced pressure, water was then added. After 2 h the solvent were remover under reduced pressure off to leave (2R,3S)-3-trimethylamonium-2-hydroxy-5-methyl-hexyl)-phosphonic acid; iodide, compound 7. Compound 7 was dissolved in methanol and crystallization was induced by the addition of ethyl acetate. The product that crystallized was filtered and dried under reduced pressure to give 5.8 g (61.63%) of the title compound. $^1H$ NMR (200 MHz, $CD_3OD$) δ 1.04 (d, J=6.6 Hz, 6H, $(CH_3)_2CH$), 1.73 (m, 3H, $CH_2CH, CH(CH_3)_2$), 2.29 (m, 2H, $CH_2P$), 3.28 (s, 9H, $(CH_3)_3N$), 3.57 (d, J=8.2 Hz, 1H, CHN), 4.33 (m, 1H, CHOH). $^{13}C$ NMR (50 MHz, $CD_3OD$) δ 21.64 $((CH_3)_2CH)$, 23.92 $((CH_3)_2CH)$, 27.43 (CH $(CH_3)_2$), 36.48 (d, J=134.1 Hz, $CH_2P$), 38.52 ($CH_2CH$), 53.98 $((CH_3)_3N)$, 68.89 (CHN), 73.48 (d, J=11.0 Hz, CHOH).
$^{31}P$ NMR (81 MHz, $CD_3OD_3$) δ 24.898.

EXAMPLE 3

Induction of Changes of Utilization of Glucose in Hepatic Cells

WRL-68 cells were thawed and maintained in culture with Minimal Essential Medium (Gibco BRL) containing 4 mM Glutamine, 1% non essential aminoacids (Gibco BRL), 10% Fetal Calf Serum (FCS), and 100 μg/ml of ampicillin. WRL-68 cells were seeded at $2×10^6$ cells/$cm^2$ in complete media in 75 $cm^2$ cell culture flasks, cells were maintained for 24 hours at 37° C. under an atmosphere of 5% CO2. The medium was changed after 24 hr. Cells were passaged by trypsinization using a 0.025% trypsin solution containing 0.01% N,N,-diethyldithiocarbamic acid sodium salt (EDTA). In order to evaluate the effect of analog of carnitine on utilization of glucose levels a model of hyperglycemia in vitro (Nakajina et al., *J. Biol. Chem.* 275:20880-20886 (2000)) was developed. Two days after plating, the medium was changed to F-12K containing 7 mM D-glucose and 10% fetal bovine serum, and the culture was continued for 2 more days. The cells were then cultured in serum-free F-12K medium containing 30 mM D-glucose for 24 h. Cells were treated with the diastereomeric mixture of compound 7 at concentrations of 0.01, 0.1, 1,10, 100 µM, and 1 mM and 2 mM during 24 hours. Samples of conditioned media and cell lysates were kept to minus 8° C. Glucose and glycogen levels were measured by using a Glucose PAP-SL Kit (Tech, USA) and glycogen assay kit (Biovision Research Products, California, USA).

Figure 2:
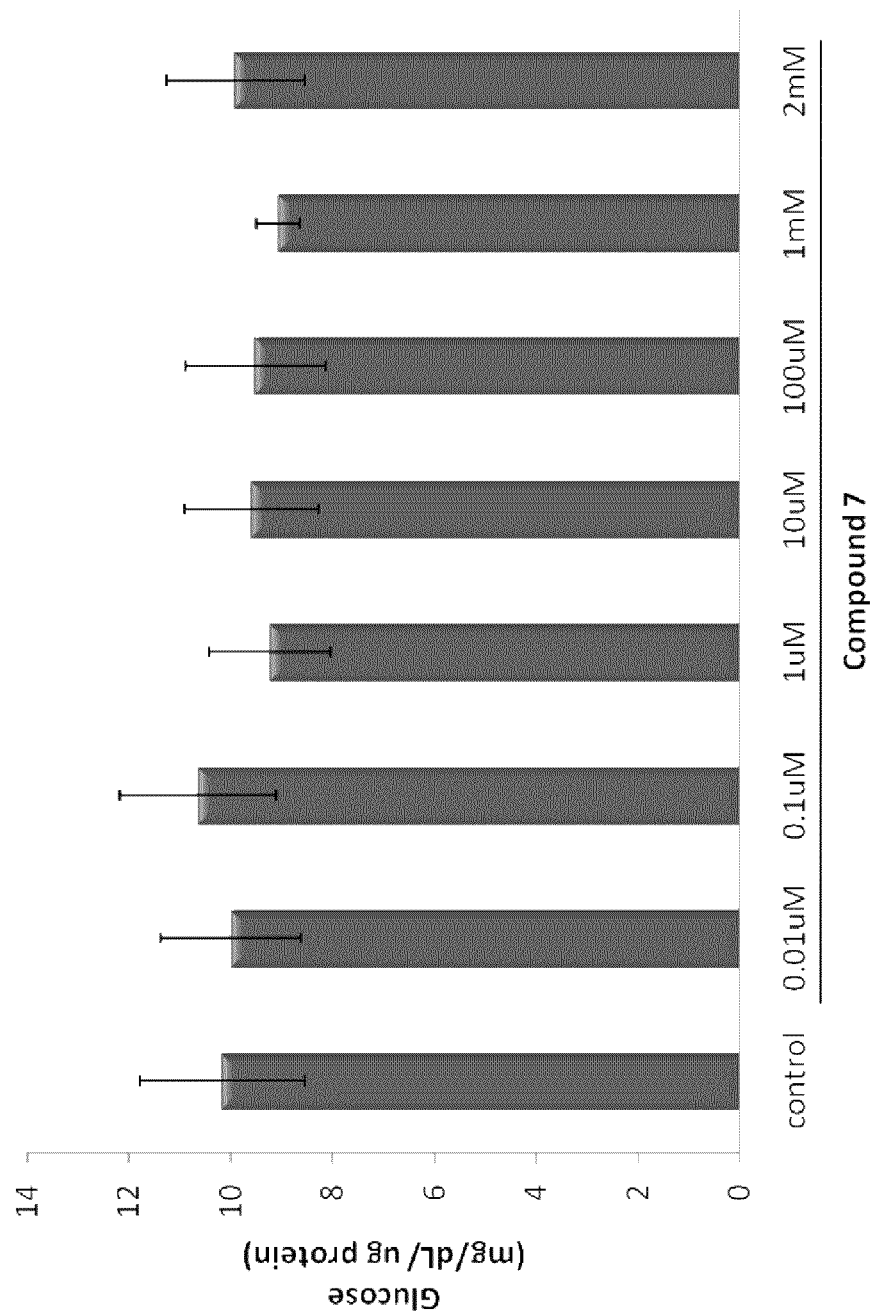
FIG. 2 is a bar graph showing intracellular glucose levels in hepatic cells treated with different concentrations of the diastereomeric mixture of compound 7.
Figure 3:
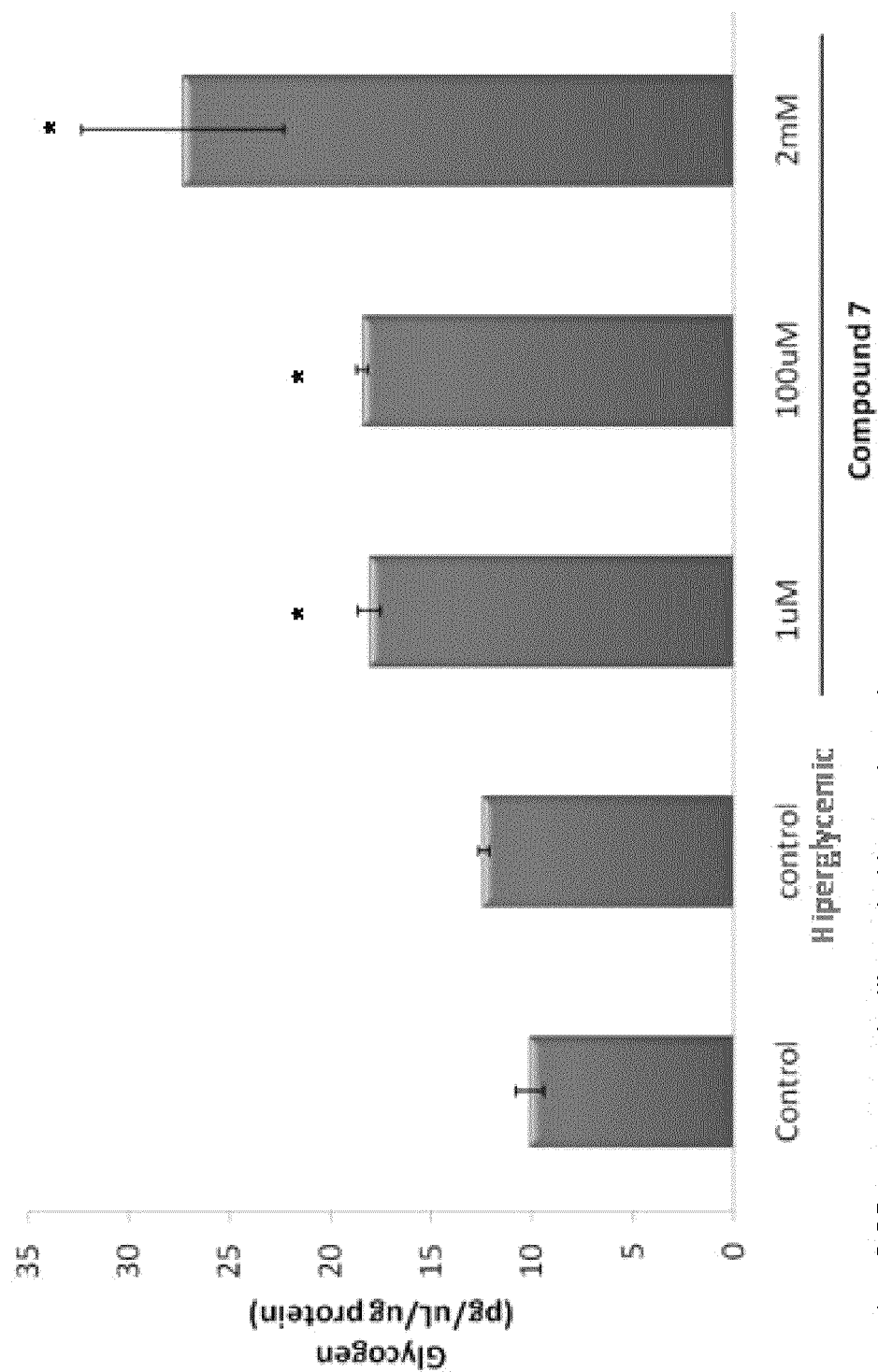
FIG. 3 is a bar graph showing intracellular glycogen levels in hepatic cells treated with different concentrations of the diastereomeric mixture of compound 7.

The diastereomeric mixture of compound 7 in concentrations of 1, 10 and 100 µM reduced the extracellular glucose levels in 16%, 18% and 23%, respectively; while a reduction of 30 and 32% was observed with concentrations of 1 and 2 mM (FIG. 1). No changes in cellular glucose were observed with any concentration (FIG. 2). An increase in cellular glycogen levels were observed with diastereomeric mixture of compound 7 at a concentration of 2 mM (FIG. 3).

EXAMPLE 4

Safety of Analog of Carnitine in Human Cells and Evaluation of Teratogenicity Two cell lines were used for this study: 293Q cells derived from normal epithelial cells of human fetal kidney (CRL-1573 ATCC) and WRL-68 cells derived from epithelial cells of human liver (CRL-48 ATCC). Cell lines were cultured in minimal essential medium (MEM, GIBCO BRL Inc., Grand Island, N.Y.), supplemented with nonessential amino acids (GIBCO BRL Inc., Grand Island, N.Y.), 10% fetal calf serum (GIBCO BRL Inc., Grand Island, N.Y.), 1-glutamine (2 mol/L), and antibiotics. Cells were plated in 100-mm culture dishes ($10^6$ cells/dish), and maintained at 37° C. under an atmosphere of 5% $CO_2$ in humidified air. Subcultures were obtained by trypsinization (0.025% trypsin solution containing 0.01% N,N-diethyldithiocarbamic acid sodium salt, EDTA). For cytological investigation, $10^5$ cells per mL of MEM medium were used. Cells were treated with the following concentrations of the diastereomeric mixture of compound 7: 0.01, 0.1, 1, 10, and 100 µM, and 1 and 2 mM. After incubation of the cells with the extract, they were collected for further cytological investigations.

Figure 4:
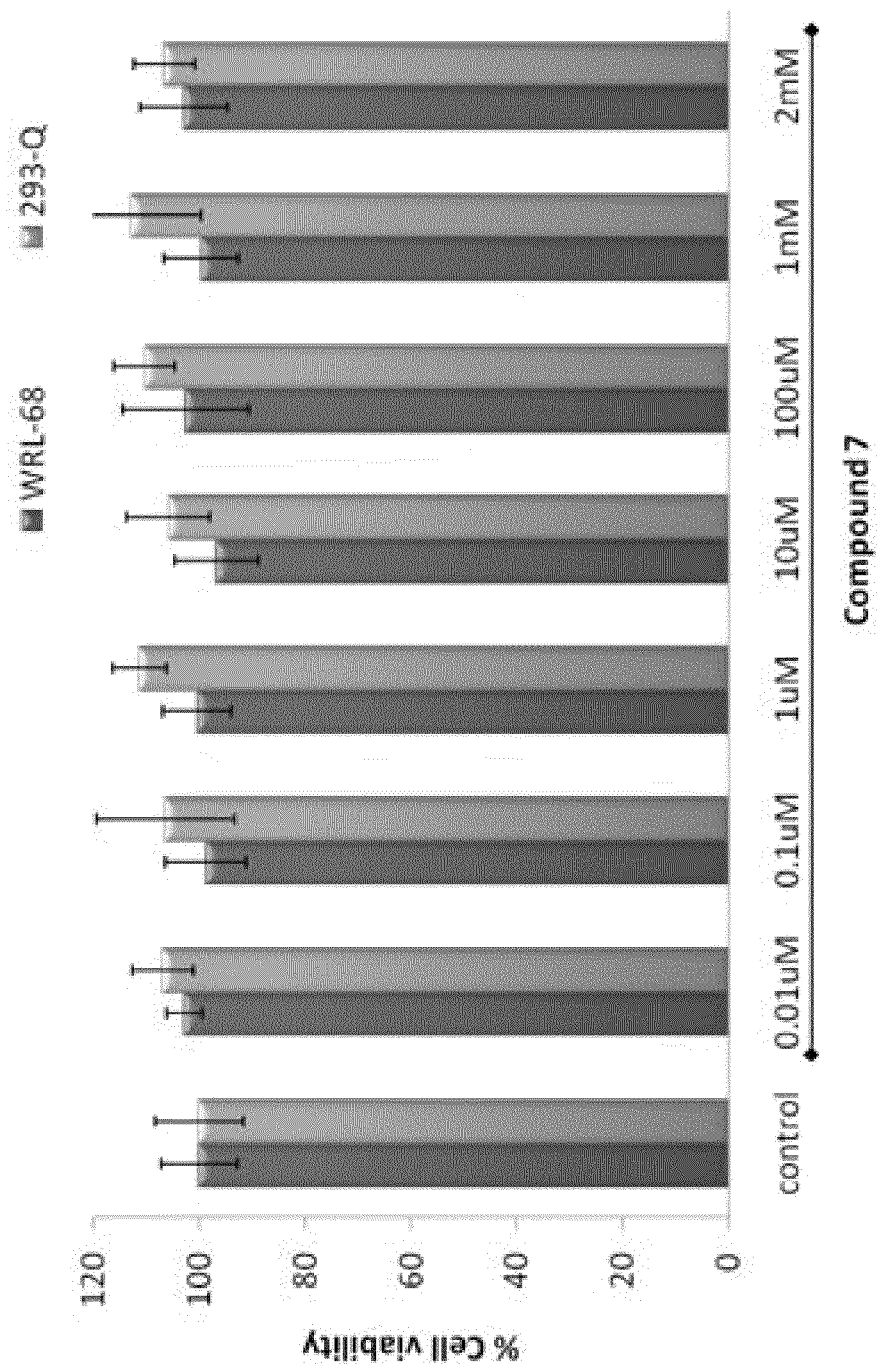
FIG. 4 is a bar graph showing the effect of the diastereomeric mixture of compound 7 on cell viability of renal and hepatic cells.
Figure 5:
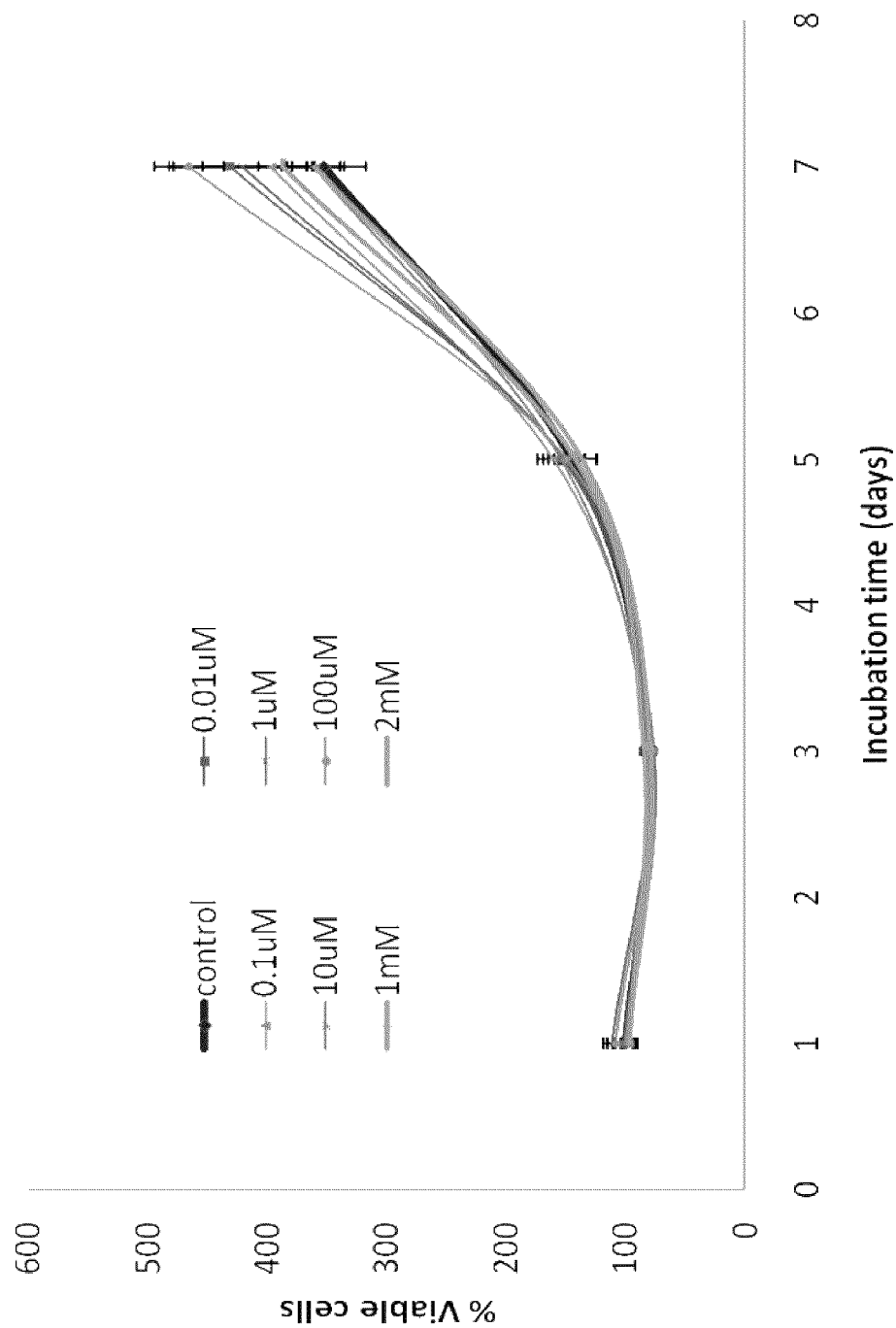
FIG. 5 is a line graph showing the effect of the diastereomeric mixture of compound 7 on cell proliferation of renal cells.
Figure 6:
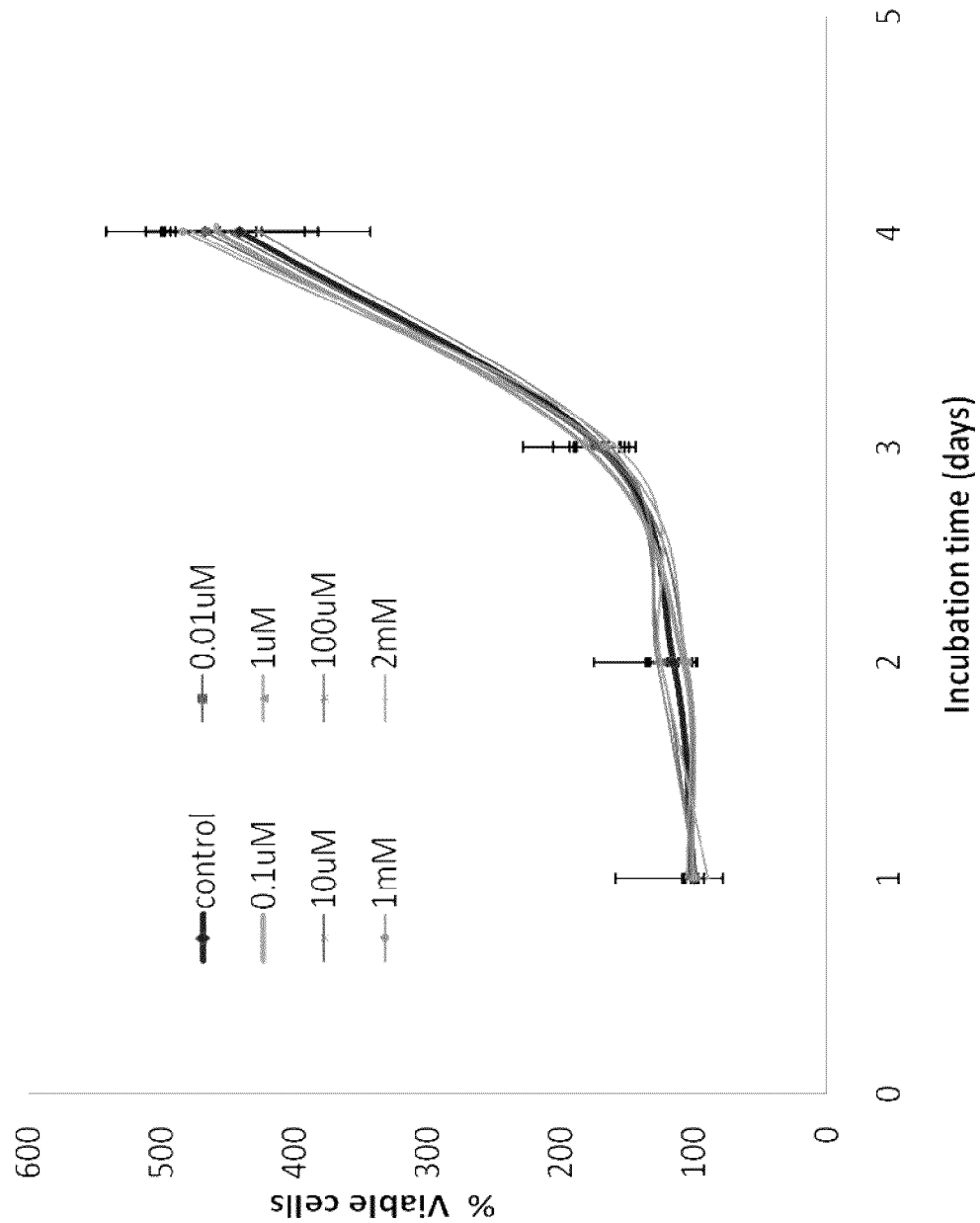
FIG. 6 is a line graph showing the effect of the diastereomeric mixture of compound 7 on cell proliferation of hepatic cells.

Cells were incubated in 96-well plates. After 24 h, the medium was removed; the cells were washed twice with PBS and then incubated with analog. After 24 h, both cells and conditioned media were collected and processed. Cell viability was measured by a 3-(4,5-dimethylthiazol-2-yl)-2,5-diphenyltetrazolium bromide (MTT) assay (Wang et al., *Journal Ocular. Pharm. Ther.* 12: 35-43 (1996)). Briefly, 20 µL MTT (5 g/L) was added to each well and incubated with the culture for an additional 4 h at 37° C., 5% $CO_2$ and then culture media was discarded followed by addition of 200 µL DMSO with 25 µL Sørensen's glycine buffer (glycine 0.1 M, NaCl 0.1 M, pH 10.5) to each well. When the blue crystals were dissolved, the optical density was determined on a microplate reader at 450 nm. In order to evaluate the effect of the diastereomeric mixture of compound 7 on cell proliferation the MTT was also used. To this end cells were collected everyday during four days for hepatic cells and seven days for renal cells. Cells exposed to the diastereomeric mixture of compound 7 did not show citotoxicity or effects on cell proliferation (FIGS. 4, 5 and 6).

EXAMPLE 5

Teratogenicity Assay

A teratogenicity assay was carried out as described by Jelinek et al., *Func. Devel. Morph.* 4:317-23 (1994). Fertile White Leghorn chicken eggs were obtained from A.L.P.E. S.A. (Puebla, Mexico) and were stored at 6° C. Sixty fertilized eggs were weighed, sterilized, and divided into six groups. First group served as a non-treated control. The next three were exposed to the diastereomeric mixture of compound 7 (1, 10, and 100 µM). The last group received caffeine (10 mg/mL) and as positive control. Test solutions (1 mL) were added to the air sac under sterile conditions. Each solution was injected after drilling into the shell at the blunt end of the egg; after injection, the holes were immediately sealed with melted paraffin wax. The eggs were then transferred and maintained in a forced draft incubator at 37.5° C. with a relative humidity of 55% until the desired stage of development was reached.

Figure 7:
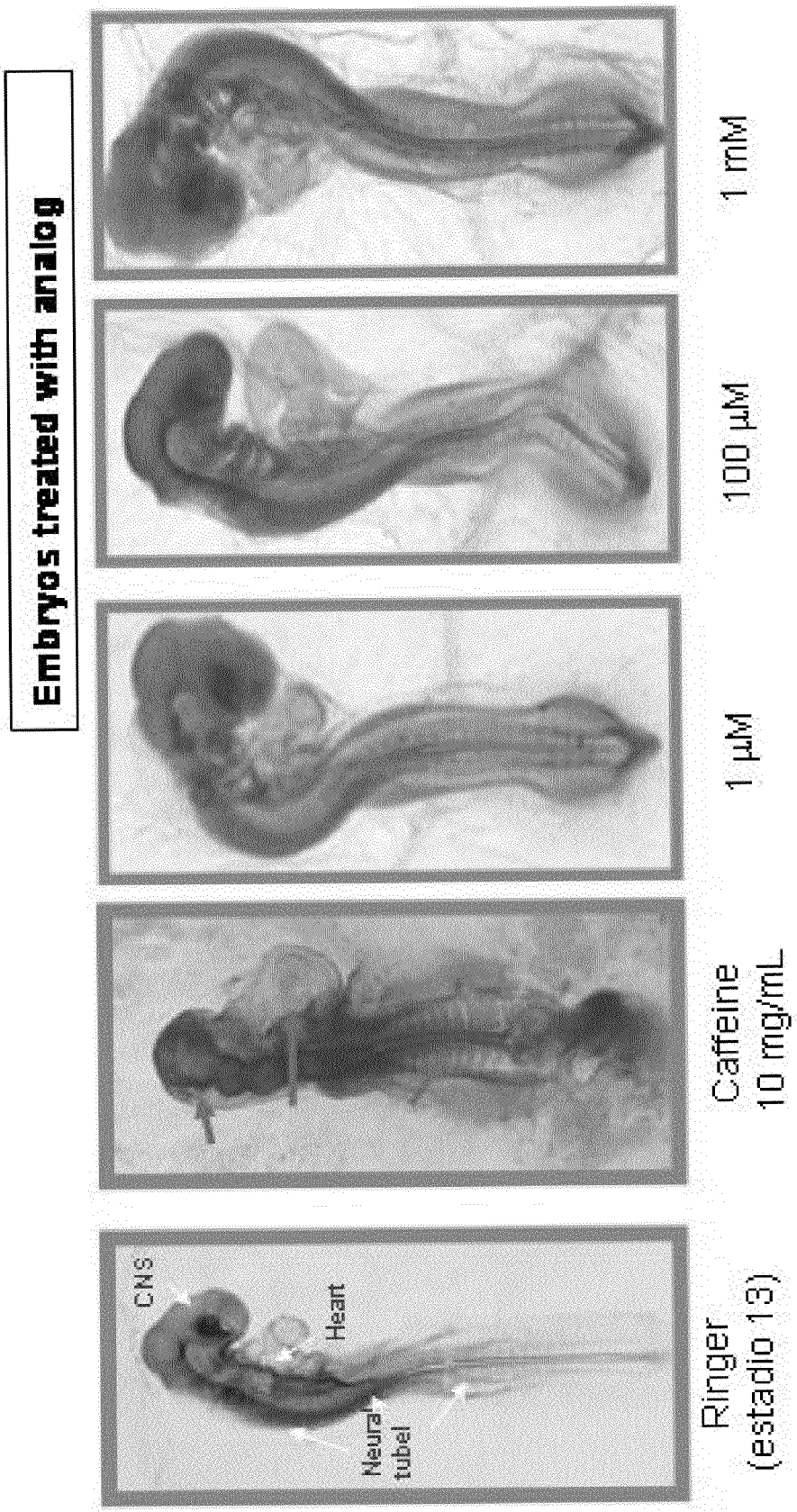
FIG. 7 is a series of five illustrations that show the morphological appearance of chick embryos treated with different concentrations of the diastereomeric mixture of compound 7.

To determine the concentration dependency of the diastereomeric mixture of compound 7, a histological analysis was carried out. Embryos in each group were fixed in buffered formal saline (pH 7.4), dehydrated, and embedded in paraffin blocks. Paraffin tissue sections of 6 µm were stained with acetocarmine for routine histological examination. The embryo was examined and staged according to morphological criteria previously outlined by Hamburger et al. (Hamburger et al., *J. Morph.* 88:49-921951 (1951). Embryonic stages at the time of the diastereomeric mixture of compound 7 application varied from 14-16, which correspond approximately to developed somites numbered 22-28. No alterations in embryos treated with the diastereomeric mixture of compound 7 were found (FIG. 7 and Table 1).

TABLE 1

Teratogenic evaluation of diastereometic mixturecompound 7 Embryonic region affected

| 48 h of exposition | Axial skeleton | CNS | Vasculature | Heart | Somites | Deaths |
|---|---|---|---|---|---|---|
| Ringer[1] | 0/10 | 0/10 | 0/10 | 0/10 | 0/10 | 0/10 |
| Cpd 7 1 µM | 0/10 | 0/10 | 0/10 | 0/10 | 0/10 | 0/10 |
| Cpd 7 100 µM | 0/10 | 0/10 | 0/10 | 0/10 | 0/10 | 0/10 |
| Cpd 7 1 mM | 0/10 | 0/10 | 0/10 | 0/10 | 0/10 | 0/10 |
| Caffeine[2] | 10/10 | 8/10 | 6/10 | 8/10 | 8/10 | 2/10 |

[1]Negative control;
[2]Positive control;
The fractions represent the number of abnormal embryos and the total examined for each developmental region of the embro.

The present invention has been described with reference to certain embodiments thereof. However, the scope of the invention is not limited to the embodiments described or exemplified. Workers of ordinary skill in the relevant arts will readily appreciate that other embodiments and examples can be practiced without departing from the scope of the present invention. All such variations are considered to be part of, and therefore encompassed by, the present invention.

All publications, patents and patent applications mentioned or referenced in this specification are herein incorporated by reference to the same extent as if each individual publication, patent or patent application was specifically and individually indicated to be incorporated by reference

What is claimed is:

1. A compound of Formula I

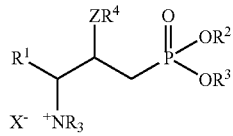

wherein:

R is lower alkyl;

$R^1$ is selected from the group consisting of n-propyl, isopropyl, n-butyl, isobutyl, sec-butyl, tert-butyl, aralkyl, optionally substituted cycloalkyl, optionally substituted alkenyl, optionally substituted alkynyl, optionally substituted aryl, optionally substituted heteroaryl, and optionally substituted heterocyclo;

$R^2$ and $R^3$ are independently selected from the group consisting of hydrogen, optionally substituted alkyl, aralkyl, optionally substituted aryl, and monovalent pharmaceutically acceptable cation, or taken together $R^2$ and $R^3$ represent a divalent pharmaceutically acceptable cation;

$R^4$ is selected from the group consisting of hydrogen, optionally substituted alkyl, optionally substituted cycloalkyl, optionally substituted alkenyl, optionally substituted alkynyl, and $COR^5$;

$R^5$ is selected from the group consisting of optionally substituted alkyl, aralkyl, optionally substituted cycloalkyl, optionally substituted alkenyl, optionally substituted alkynyl, optionally substituted aryl, optionally substituted heteroaryl, and optionally substituted heterocyclo;

$X^-$ is a pharmaceutically acceptable anion, or $X^-$ and $R^2$ are absent and the compound of Formula I is a zwitterion;

Z is selected from the group consisting of O and $NR^{10}$; and $R^{10}$ is selected from the group consisting of hydrogen, optionally substituted alkyl, aralkyl, optionally substituted cycloalkyl, optionally substituted alkenyl, optionally substituted alkynyl, optionally substituted aryl, optionally substituted heteroaryl, and optionally substituted heterocyclo;

or a pharmaceutically acceptable hydrate, crystalline form or amorphous form thereof, or a stereoisomer or mixture of stereoisomers thereof.

2. The compound of claim 1, wherein R is methyl.
3. The compound of claim 1, wherein $R^1$ is isobutyl.
4. The compound of claim 1, wherein Z is O.
5. The compound of claim 4, wherein $R^4$ is hydrogen.
6. The compound of claim 1, wherein $R^2$ and $R^3$ are hydrogen.
7. The compound of claim 1, wherein $X^-$ is selected from the group consisting of hydroxide, chloride, bromide, iodide, sulphate, nitrate, phosphate, formate, acetate, maleate, fumarate, citrate, oxalate, succinate, tartrate, malate, mandelate, lactate, gluconate, trifluoroacetate, methanesulphonate, besylate and p-toluenesulphonate.
8. The compound of claim 2, wherein $R^1$ is selected from the group consisting of n-propyl, isopropyl, n-butyl, isobutyl, sec-butyl, tert-butyl, benzyl, and phenyl, $R^2$ and $R^3$ are independently selected from the group consisting hydrogen, methyl, ethyl, n-propyl, isopropyl, n-butyl, isobutyl, sec-butyl, tert-butyl, isopenyl, benzyl, and phenyl, and $R^4$ and $R^{10}$ are hydrogen.
9. The compound of claim 1, wherein said compound of Formula I is in the 2R, 3S-isomeric form.

10. The compound of claim 1, wherein said compound is:

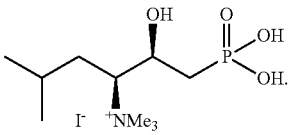

11. A process for preparing a compound of Formula III:

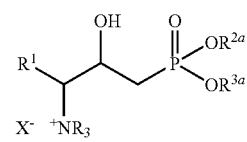

wherein:

R is lower alkyl;

$R^1$ is selected from the group consisting of n-propyl, isopropyl, n-butyl, isobutyl, sec-butyl, tert-butyl, aralkyl, optionally substituted cycloalkyl, optionally substituted alkenyl, optionally substituted alkynyl, optionally substituted aryl, optionally substituted heteroaryl and optionally substituted heterocyclo;

$R^{2a}$ and $R^{3a}$ are idependently selected from the group consisting of optionally substituted alkyl, aralkyl and optionally substituted aryl; and $X^-$ is a pharmaceutically acceptable anion;

said method comprising:

(a) reacting a compound of Formula IV:

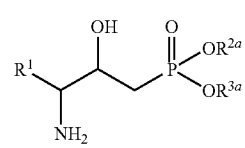

with RX, to give said compound of Formula III, and (b) isolating said compound of Formula III.

12. The process of claim 11, wherein said compound of Formula III is the 3S-isomer and said compound of Formula IV is the 3S-isomer.

13. The process of claim 12 further comprising:

(c) isolating the 2S,3S-isomer substantially free from the 2R,3S-isomer, or (d) isolating the 2R,3S-isomer substantially free from the 2S,3S-isomer.

14. The process of claim 13 further comprising:

(e) removing $R^{2a}$ and $R^{3a}$ from said 2S,3S-isomer, to give a compound of Formula 2S,3S-X:

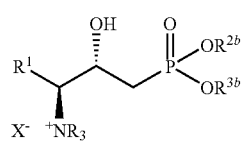

or, (f) removing $R^{2a}$ and $R^{3a}$ from said 2R,3S-isomer, to give a compound of Formula 2R,3S-X:

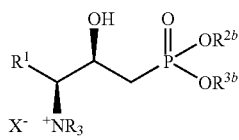

wherein $R^{2b}$ and $R^{3b}$ are selected from the group consisting of hydrogen and monovalent pharmaceutically acceptable cation, or taken together $R^{2b}$ and $R^{3b}$ represent a divalent pharmaceutically acceptable cation, or $X^-$ and $R^{2b}$ are absent.

15. The process of claim 11, wherein said process comprises removing $R^6$, or $R^6$ and $R^7$, from a compound of Formula V:

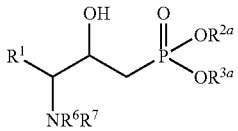

wherein:
$R^6$ is an amine protecting group; and
$R^7$ is selected from the group consisting of hydrogen and amine protecting group, or $R^6$ and $R^7$ taken together represent an amine protecting group, to give said compound of Formula IV.

16. The process of claim 15, wherein said process comprises reduction of a compound of Formula VI:

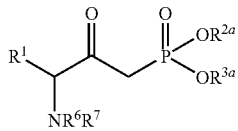

to give said compound of Formula V.

17. The process of claim 16, wherein said process comprises condensing a compound of Formula VII:

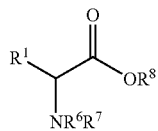

with a compound of Formula VIII:

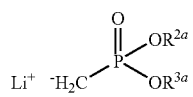

to give said compound of Formula VI, wherein:
$R^8$ is selected from the group consisting of optionally substituted alkyl, aralkyl, and optionally substituted aryl.

18. The process of claim 17, wherein said process comprises condensing a compound of Formula IX:

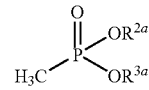

with $LiR^9$, to give said compound of Formula VIII, wherein $R^9$ is selected from the group consisting of lower alkyl and aryl.

19. The process of claim 17, wherein said process comprises:
(a) protecting the —$NH_2$ group of Formula XI; and
(b) esterifying the carboxylic acid of an amino acid of Formula XI:

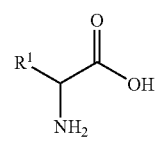

to give said compound of Formula VII.

20. The process of claim 11, wherein said compound of Formula III is obtained via a one pot process from a compound of Formula XI:

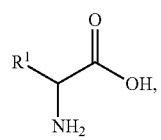

the process comprising:
1) obtaining a compound of Formula VII:

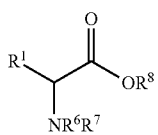

from said compound of Formula XI,
wherein:
$R^6$ is an amine protecting group; and
$R^7$ is selected from the group consisting of hydrogen and amine protecting group, or $R^6$ and $R^7$ taken together represent an amine protecting group: and
$R^8$ is selected from the group consisting of optionally substituted alkyl, aralkyl, and optionally substituted aryl;

2) obtaining a compound of Formula VI:

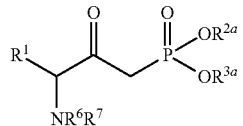

VI from said compound of Formula VII:

3) obtaining a compound of Formula V:

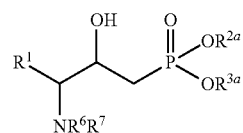

V from said compound of Formula VI;

4) obtaining a compound of Formula IV

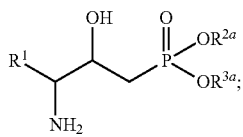

IV from said compound of Formula V; and 5) obtaining said compound of Formula III from said compound of Formula IV.

21. A pharmaceutical composition comprising the compound of claim 1 and a pharmaceutically acceptable carrier.

* * * * *